(12) United States Patent
Liew et al.

(10) Patent No.: US 12,234,492 B2
(45) Date of Patent: Feb. 25, 2025

(54) MICROORGANISM FOR FERMENTATIVE PRODUCTION OF 2-PHENYLETHANOL FROM GASEOUS SUBSTRATES

(71) Applicant: LanzaTech, Inc., Skokie, IL (US)

(72) Inventors: Fungmin Liew, Skokie, IL (US); Michael Koepke, Skokie, IL (US); Shilpa Nagaraju, Skokie, IL (US); Audrey Harris, Skokie, IL (US)

(73) Assignee: LanzaTech, Inc., Skokie, IL (US)

( * ) Notice: Subject to any disclaimer, the term of this patent is extended or adjusted under 35 U.S.C. 154(b) by 200 days.

(21) Appl. No.: 17/150,900

(22) Filed: Jan. 15, 2021

(65) Prior Publication Data

US 2021/0292732 A1    Sep. 23, 2021

Related U.S. Application Data

(60) Provisional application No. 62/991,428, filed on Mar. 18, 2020.

(51) Int. Cl.
| | | |
|---|---|---|
| *C12N 9/88* | (2006.01) | |
| *C12N 9/02* | (2006.01) | |
| *C12N 9/04* | (2006.01) | |
| *C12N 9/06* | (2006.01) | |
| *C12N 9/10* | (2006.01) | |
| *C12N 9/12* | (2006.01) | |
| *C12N 9/90* | (2006.01) | |
| *C12P 7/22* | (2006.01) | |

(52) U.S. Cl.
CPC ............ *C12N 9/88* (2013.01); *C12N 9/0006* (2013.01); *C12N 9/0008* (2013.01); *C12N 9/0016* (2013.01); *C12N 9/1085* (2013.01); *C12N 9/1092* (2013.01); *C12N 9/1205* (2013.01); *C12N 9/1294* (2013.01); *C12N 9/90* (2013.01); *C12P 7/22* (2013.01); *C12Y 101/01025* (2013.01); *C12Y 102/07005* (2013.01); *C12Y 205/01019* (2013.01); *C12Y 207/01071* (2013.01); *C12Y 207/09001* (2013.01); *C12Y 401/01043* (2013.01); *C12Y 402/0101* (2013.01); *C12Y 402/01051* (2013.01); *C12Y 402/03004* (2013.01); *C12Y 402/03005* (2013.01); *C12Y 504/99005* (2013.01)

(58) Field of Classification Search
None
See application file for complete search history.

(56) References Cited

U.S. PATENT DOCUMENTS

| | | | |
|---|---|---|---|
| 4,753,883 A | 6/1988 | Backman et al. | |
| 7,314,974 B2 * | 1/2008 | Cao | C07K 14/195 800/290 |
| 7,704,723 B2 | 4/2010 | Huhnke | |
| 7,972,824 B2 | 7/2011 | Simpson | |
| 8,222,013 B2 | 7/2012 | Simpson | |
| 8,293,509 B2 | 10/2012 | Simpson | |
| 8,298,798 B2 * | 10/2012 | Liao | C12P 7/16 435/193 |
| 8,318,473 B2 * | 11/2012 | Yoshikuni | C12N 15/70 435/146 |
| 8,658,408 B2 | 2/2014 | Simpson | |
| 8,709,811 B2 * | 4/2014 | Klee | C12N 9/88 435/468 |
| 8,900,836 B2 | 12/2014 | Simpson | |
| 8,975,049 B2 * | 3/2015 | Liao | C12P 7/16 435/157 |
| 9,068,202 B2 | 6/2015 | Tran | |
| 9,284,564 B2 | 3/2016 | Mueller | |
| 9,347,076 B2 | 5/2016 | Liew | |
| 9,359,611 B2 | 6/2016 | Koepke | |
| 9,410,130 B2 | 8/2016 | Koepke | |
| 9,738,875 B2 | 8/2017 | Koepke | |
| 9,890,384 B2 | 2/2018 | Mueller | |
| 9,994,878 B2 | 6/2018 | Koepke | |
| 10,174,303 B2 | 1/2019 | Behrendorff | |
| 10,494,600 B2 | 12/2019 | Heijstra | |
| 10,590,406 B2 | 3/2020 | Koepke | |
| 10,696,975 B2 * | 6/2020 | Coffin | C12N 15/8271 |
| 10,815,508 B2 * | 10/2020 | Skerra | C12P 7/42 |
| 10,913,958 B2 | 2/2021 | Koepke | |
| 2009/0081746 A1 | 3/2009 | Liao | |
| 2012/0045807 A1 | 2/2012 | Simpson | |
| 2013/0157322 A1 | 6/2013 | Simpson | |
| 2014/0377857 A1 | 12/2014 | Liao et al. | |
| 2019/0185888 A1 | 6/2019 | Koepke | |
| 2021/0292732 A1 * | 9/2021 | Liew | C12N 9/88 |

FOREIGN PATENT DOCUMENTS

| | | |
|---|---|---|
| CN | 106566794 A | 4/2017 |
| WO | 2011037598 A1 | 3/2011 |
| WO | 2012115527 | 8/2012 |
| WO | 2018217168 | 11/2018 |
| WO | 2019126400 A1 | 6/2019 |

OTHER PUBLICATIONS

Makino et al. (Applied and Environmental Microbiology, 2005, pp. 4713-4720).*
Abrini, Arch Microbiol, 161: 345-351, 1994.
Al-Hinai, Appl Environ Microbiol, 78: 8112-8121, 2012.
Argyros, Appl Environ Microbiol, 77: 8288-8294, 2011.
Corre et al., Res Microbiol. 1990;141(4):483-97.
De La Plaza et al., FEMS Microbiol Lett. 2004; 238(2):367-74.
Drake, Acetogenic Prokaryotes, In: The Prokaryotes, 3rd edition, p. 354, New York, NY, 2006.
Giersberg et al., J Ind Microbiol Biotechnol. Sep. 2012;39(9):1385-96.
Guo et al., Microbiologyopen. Aug. 2017;6(4).
Heap, J Microbiol Methods, 78: 79-85, 2009.

(Continued)

*Primary Examiner* — Hope A Robinson

(57) ABSTRACT

Disclosed herein are improved methods for production of 2-phenylethanol by microbial fermentation of substrates comprising carbon monoxide and/or carbon dioxide and further disclosed are genetically modified microorganisms for use in such methods that alleviate dependence on natural and petrochemical processes.

13 Claims, 21 Drawing Sheets

Specification includes a Sequence Listing.

(56) References Cited

OTHER PUBLICATIONS

Heap, Nucl Acids Res, 40: e59, 2012.
Hirano et al., Appl Microbiol Biotechnol. 2007;76(2):357-63.
Hu et al., J Basic Microbiol. 2003;43(5):399-406.
Itoh et al., Appl Environ Microbiol. Oct. 1997;63(10):3783-8.
Kneen et al., FEBS J. 2011;278:1842-53.
Köpke, Curr Opin Biotechnol, 22: 320-325, 2011.
Kubota et al., Appl Microbiol Biotechnol. 2013;97:8139-49.
Kuehne, Strain Eng: Methods and Protocols, 389-407, 2011.
Larroy et al., Chem Biol Interact. Feb. 1, 2003;143-144:229-38.
Liew, Frontiers Microbiol, 7: 694, 2016.
Nagaraju, Biotechnol Biofuels, 9: 219, 2016.
Perez, Biotechnol Bioeng, 110:1066-1077, 2012.
Ragsdale, Biochim Biophys Acta, 1784: 1873-1898, 2008.
Schuchmann, Nat Rev Microbiol, 12: 809-821, 2014.
Spaepen et al., J Bacteriol. 2007;189:7626 LP-7633.
Sun et al., Appl Environ Microbiol. 2013; 79(13):4024-30.
Tanner, Int J System Bacteriol, 43: 232-236, 1993.
Tieman et al., Phytochemistry. 2007;68(21):2660-9.
Ueki, mBio, 5: e01636-01614, 2014.
Zhang, Journal Microbiol Methods, 108: 49-60, 2015.
International Search Report and Written Opinion issued in corresponding International Application No. PCT/US2021/013723, dated May 12, 2021, 12 pages.
Kong, S. et al. "De novo biosynthesis of 2-phenylethanol in engineered Pichia pastoris," Enzyme and Microbial Technology 133 (2020) 109459, 4 pages.
Liu, C. et al. "Genome mining of 2-phenylethanol biosynthetic genes from *Enterobacter* sp. CGMCC 5087 and heterologous overproduction in *Escherichia coli*," Biotechnol Biofuels (2018) 11:305, 15 pages.
Extended European Search Report issued in corresponding EP Application No. 21772079.6, dated Apr. 15, 2024, 9 pages.
Werner et al., "Fast track assembly of Multigene constructs using Golden Gate cloning and the MoClo system", Bioengineered, vol. 3, No. 1, pp. 38-43, Jan. 1, 2012.

\* cited by examiner

| PAR variant | Species | AA Length | Cofactor | Reference |
|---|---|---|---|---|
| adh6 | Saccharomyces cerevisiae | 360 | NADPH | Chemico-Biological Interactions 143-144 (2003): 229-238 |
| lePAR | Solanum lycopersicum | 328 | NADPH | Phytochemistry 68 (2007) 2660 - 2779 |
| ecPAR | Escherichia coli | 339 | ? | MicrobiologyOpen (2017) 6: e486 |
| blPAR | Brevibacterium linens | 363 | NADH | Journal of Bioscience and Bioengineering 100 (2005): 318 - 322 |
| rrPAR | Rhodococcus ruber | 346 | NADH | Journal of Industrial Microbiology and Biotechnology 39 (2012): 1385 - 1396 |
| rsPAR | Rhodococcus sp. ST-10 | 348 | NADH | Applied and Environmental Microbiology 63 (1997): 3783 - 3788 |

Figure 4A

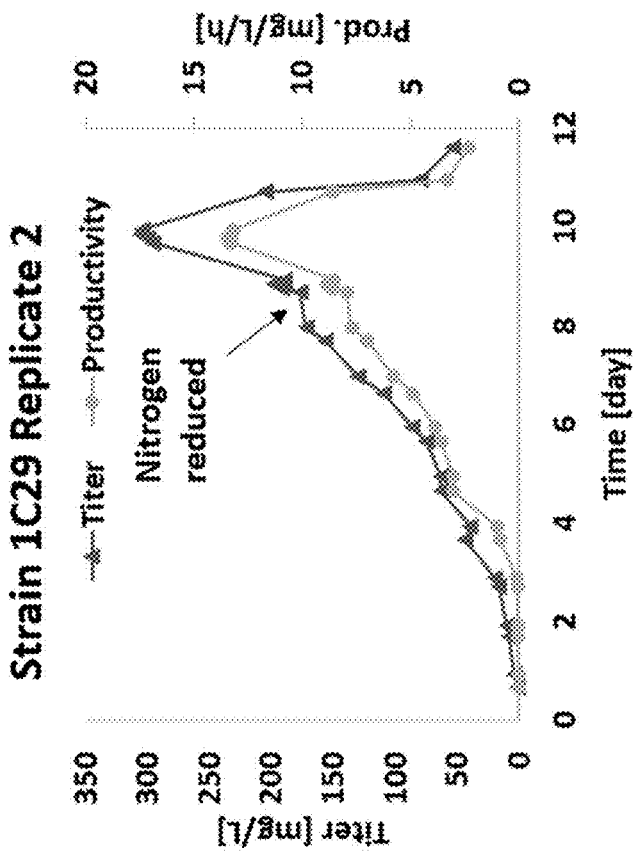
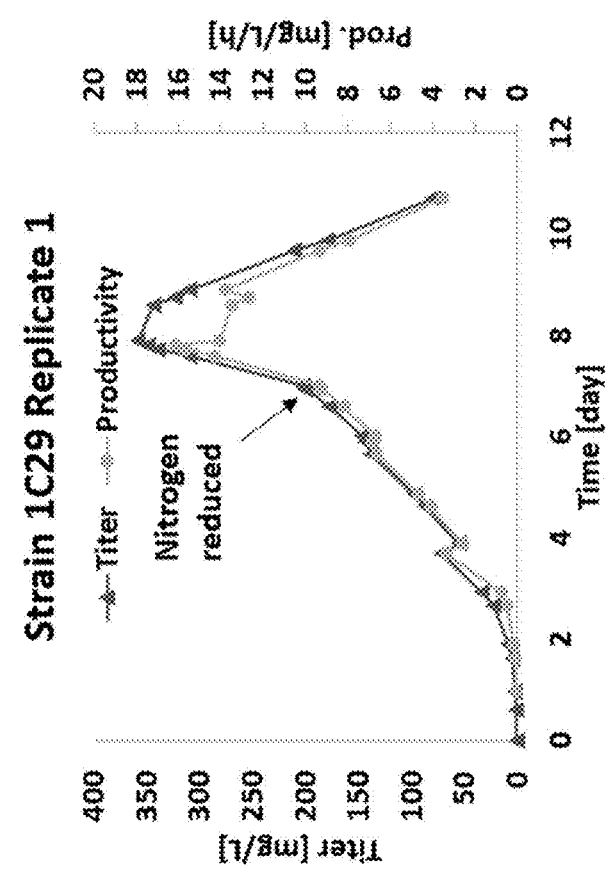
Figure 10B
Figure 10A

MICROORGANISM FOR FERMENTATIVE PRODUCTION OF 2-PHENYLETHANOL FROM GASEOUS SUBSTRATES

CROSS REFERENCE TO RELATED APPLICATIONS

This application claims the benefit of U.S. Provisional Patent Application No. 62/991,428 filed Mar. 18, 2020, the entirety of which is incorporated herein by reference.

GOVERNMENT RIGHTS

This invention was made with government support under Cooperative Agreement DE-EE0007728 awarded by the United States Department of Energy. The government has certain rights in the invention.

FIELD OF THE DISCLOSURE

This application relates to methods for production of 2-phenylethanol by microbial fermentation of substrates comprising carbon dioxide ($CO_2$), carbon monoxide (CO), and/or hydrogen ($H_2$) and genetically modified microorganisms for use in such methods.

BACKGROUND

Mitigation of impending climate change requires drastic reductions in emissions of greenhouse gases (GHGs), such as those generated through the burning of fossil fuels like coal and oil. Although sustainable sources of chemicals and transportation fuels are currently insufficient to significantly displace our dependence on fossil carbon, gas fermentation has recently emerged as an alternative platform for the biological fixation of such gases such as $CO_2$, CO, and/or $H_2$ into sustainable fuels and chemicals. In particular, gas fermentation technology can utilize a wide range of feedstocks including gasified organic matter (e.g., municipal solid waste or agricultural waste) or industrial waste gases (e.g., from steel mills or oil refineries) to produce ethanol, jet fuel, and a variety of other products. Gas fermentation alone could displace 30% of crude oil use and reduce global $CO_2$ emissions by 10%, but, as with any disruptive technology, many technical challenges must be overcome before this potential is fully achieved.

2-phenylethanol (2-PE) is a commodity chemical with a market of 6010 mt/yr in food, fragrance and flavor industries for its "rose-like" aroma and 900 mt/yr in chemical industries as an ester intermediate and, theoretically, in styrene production. Currently, 2-PE is procured from natural sources for its application in the food, fragrance, and flavor industries, or it is synthesized by chemical means for other applications. There is thus a need for improved methods of 2-PE production that alleviate dependence on natural and petrochemical processes.

SUMMARY

In one aspect, the disclosure provides a microorganism capable of producing 2-phenylethanol, wherein the microorganism comprises a heterologous enzyme that converts phenylpyruvate to phenylacetaldehyde and a heterologous enzyme that converts phenylacetaldehyde to 2-phenylethanol.

In some embodiments, the heterologous enzyme that converts phenylpyruvate to phenylacetaldehyde is decarboxylase and the heterologous enzyme that converts phenylacetaldehyde to 2-phenylethanol is phenylacetaldehyde reductase. In particular, the decarboxylase may be a phenylpyruvate-specific decarboxylase.

In some embodiments, the microorganism is a C1-fixing microorganism, a Wood-Ljungdahl microorganism, and/or a bacterium. In some embodiments, the microorganism is a member of the genus *Acetobacterium, Alkalibaculum, Blautia, Butyribacterium, Clostridium, Eubacterium, Moorella, Oxobacter, Sporomusa*, or *Thermoanaerobacter*.

In some embodiments, the microorganism is natively capable of producing phenylpyruvate. In some embodiments, the microorganism comprises a Wood-Ljungdahl pathway that converts CO, $CO_2$, and/or $H_2$ to acetyl-CoA.

In some embodiments, the microorganism comprises one or more of: a native enzyme that converts acetyl-CoA to pyruvate; a native enzyme that converts pyruvate to phosphoenolpyruvate; a native enzyme that converts phosphoenolpyruvate and erythrose-4-phosphate to 2-dehydro-3-deoxy-D-arabino-heptonate 7-phosphate; a native enzyme that converts 2-dehydro-3-deoxy-D-arabino-heptonate 7-phosphate to 3-dehydroquinate; a native enzyme that converts 3-dehydroquinate to 3-dehydroshikimate; a native enzyme that converts 3-dehydroshikimate to shikimate; a native enzyme that converts shikimate to shikimate 3-phosphate; a native enzyme that converts shikimate 3-phosphate to 5-O-(1-carboxyvinyl)-shikimate 3-phosphate; a native enzyme that converts 5-O-(1-carboxyvinyl)-shikimate 3-phosphate to chorismate; or a native enzyme that converts chorismate to phenylpyruvate.

In some embodiments, the native enzyme that converts acetyl-CoA to pyruvate is pyruvate:ferredoxin oxidoreductase (PFOR; E.C. 1.2.7.1); the native enzyme that converts pyruvate to phosphoenolpyruvate is pyruvate phosphate dikinase (PPDK; E.C.2.7.9.1); the native enzyme that converts phosphoenolpyruvate and erythrose-4-phosphate to 2-dehydro-3-deoxy-D-arabino-heptonate 7-phosphate is 2-dehydro-3-deoxy-D-arabino-heptonate 7-phosphate synthase (DAHPS or DAHP synthase; E.C.2.5.1.54); the native enzyme that converts 2-dehydro-3-deoxy-D-arabino-heptonate 7-phosphate to 3-dehydroquinate is 3-dehydroquinate synthase (DHQS; E.C. 4.2.3.4); the native enzyme that converts 3-dehydroquinate to 3-dehydroshikimate is 3-dehydroquinate dehydratase (DHQ; E.C. 4.2.1.10); the native enzyme that converts 3-dehydroshikimate to shikimate is shikimate dehydrogenase (SDH; E.C. 1.1.1.25); the native enzyme that converts shikimate to shikimate 3-phosphate is shikimate kinase (SK; E.C. 2.7.1.71); the native enzyme that converts shikimate 3-phosphate to 5-O-(1-carboxyvinyl)-shikimate 3-phosphate is 5-enolpyruvylshikimate 3-phosphate synthase (EPSPS or EPSP synthase; E.C. 2.5.1.19); the native enzyme that converts 5-O-(1-carboxyvinyl)-shikimate 3-phosphate to chorismate is chorismate synthase (CS; E.C. 4.2.3.5); or the native enzyme that converts chorismate to phenylpyruvate is bi-functional chorismate mutase (E.C. 5.4.99.5)/prephenate dehydratase (E.C.4.2.1.51).

In some embodiments, the microorganism further comprises one or more of: a heterologous enzyme that converts phosphoenolpyruvate and erythrose-4-phosphate to 2-dehydro-3-deoxy-D-arabino-heptonate 7-phosphate; a heterologous enzyme that converts 3-dehydroshikimate to shikimate; or a heterologous enzyme that converts chorismate to phenylpyruvate.

In some embodiments, the heterologous enzyme that converts phosphoenolpyruvate and erythrose-4-phosphate to 2-dehydro-3-deoxy-D-arabino-heptonate 7-phosphate is 2-dehydro-3-deoxy-D-arabino-heptonate 7-phosphate synthase; the heterologous enzyme that converts 3-dehydroshikimate to shikimate is shikimate dehydrogenase; or the heterologous enzyme that converts chorismate to phenylpyruvate is bi-functional chorismate mutase/prephenate dehydratase.

In some embodiments, the microorganism comprises:
(1) ecAroE, kivD, 1ePAR, pheA2, and aroG;
(2) ecAroE, abPPDC, ecPAR, pheA1, and aroG;
(3) cgAroE, abPPDC, 1ePAR, pheA2, and aroG;
(4) ecAroE, abPPDC, 1ePAR, pheA2, and aroG;
(5) cgAroE, kivD, rrPAR, pheA2, and aroG;
(6) ecAroE, abPPDC, 1ePAR, pheA2, and aroG;
(7) pheA1, aroG, abPPDC, and ecPAR;
(8) egAroE, abPPDC, 1ePAR, pheA1, and aroG;
(9) ecAroE, abPPDC, ecPAR, pheA2, and aroG;
(10) cgAroE, aro10, ecPAR, pheA2, and aroG;
(11) cgAroE, abPPDC, 1ePAR, pheA1, and aroG;
(12) cgAroE, aro10, 1ePAR, pheA2, and aroG;
(13) ecAroE, abPPDC, 1ePAR, pheA1, and aroG;
(14) ecAroE, aro10, ecPAR, pheA2, and aroG;
(15) ecAroE, aro10, 1ePAR, pheA2, and aroG;
(16) cgAroE, abPPDC, 1ePAR, pheA1, and aroG;
(17) cgAroE, aro10, rsPAR, pheA2, and aroG;
(18) cgAroE, abPPDC, b1PAR, pheA2, and aroG;
(19) ecAroE, kivD, b1PAR, pheA2, and aroG;
(20) cgAroE, aro10, b1PAR, pheA2, and aroG;
(21) ecAroE, abPPDC, b1PAR, pheA2, and aroG;
(22) ecAroE, abPPDC, adh6, pheA1, and aroG;
(23) cgAroE, abPPDC, adh6, pheA2, and aroG;
(24) cgAroE, abPPDC, ecPAR, pheA2, and aroG;
(25) ecAroE, aro10, rsPAR, pheA2, and aroG;
(26) ecAroE, aro10, adh6, pheA2, and aroG; or
(27) ecAroE, abPPDC, ecPAR, pheA2, and aroG.

In some embodiments, the microorganism comprises the heterologous genes and promoters of combinatorial strain 2C03, 1C10, 2C54, 2C09, 2C47, 2C55, 2C53, H57, 1C47, 2C10, 2A18, 1054, 2C01, 1C31, 2B17, 2C52, 1C09, H18, H58, 2C27, 2D22, 2D07, 2D24, 2D03, 1C29, 2B26, 2C38, 2A27, 2C12, or 2B27.

In some embodiments, the microorganism ferments a gaseous substrate comprising CO, $CO_2$, and/or $H_2$ to produce 2-phenylethanol. In some embodiments, the gaseous substrate comprises syngas or industrial waste gas.

In some embodiments, the microorganism does not produce any other C3+ alcohols. In some embodiments, the microorganism does not produce any other C3, C4, C5, C6, C7, C8, C9, or C10 alcohols.

In another aspect, the disclosure provides a method of producing 2-phenylethanol comprising culturing the microorganism in the presence of a gaseous substrate. In some embodiments, the gaseous substrate comprises a C1-carbon source comprising CO, $CO_2$, and/or $H_2$. In some embodiments, the gaseous substrate comprises syngas or industrial waste gas.

Specific embodiments of the disclosure will become evident from the following more detailed description of certain embodiments and the claims.

BRIEF DESCRIPTIONS OF THE DRAWINGS

FIG. 1 shows the metabolic pathway leading to the biosynthesis of 2-phenylethanol by *Clostridium autoethanogenum* from gas fermentation. Enzymatic steps that require heterologous expression are the decarboxylase and phenylacetaldehyde reductase (PAR) steps. The dashed arrow depicts the multi-enzymatic core metabolic pathway in *C. autoethanogenum*. Carbon and hydrogen are assimilated to acetyl-CoA by the Wood-Ljungdahl pathway which is then converted to pyruvate by a pyruvate:ferredoxin oxidoreductase. Aromatic amino acid biosynthesis starts with phosphoenolpyruvate and erythrose-4-phosphate, which are biosynthesized from pyruvate by essential metabolic pathways like gluconeogenesis and pentose phosphate pathway. 2-phenylpyruvate can be derived from the shikimate pathway and by aminotransferase reactions between phenylalanine and keto acids. Enzymes that were heterologously expressed or overexpressed in the Examples disclosed herein are marked with a tick mark. NAD(P)H comprises NADPH and NADH.

FIGS. 2A-2B show autotrophic growth of *Clostridium autoethanogenum* in the presence of different amounts of 2-PE in Schott bottles. FIG. 2A: Growth profile; FIG. 2B: 2-PE concentration measured by GC-FID. Unc=Unchallenged; N=2; Error bar=S.D.

FIG. 3A shows the growth profile and FIG. 3B the end-point alcohol production titer during autotrophic growth using 150 kPa of synthetic gas blend (50% CO, 10% $H_2$, 30% $CO_2$ and 10% $N_2$) in Schott bottles between the three decarboxylase strains: abPPDC, aro10 and control kivD_la. N=3; Error bar=S.D.

FIGS. 4A-4C show overexpression of phenylacetaldehyde reductase (PAR) in *Clostridium autoethanogenum* for 2-PE production. FIG. 4A: The species origin, amino acid length, cofactor specificity, and reference of employed PAR. FIG. 4B: Phylogenetic tree of PAR variants using amino acid sequence. The scale bar corresponds to 0.2 change per amino acid. FIG. 4C: Normalized 2-PE production by strains with different PAR variants in 12-well plates after 7 days of incubation in the presence of 200 kPa synthetic gas blend (50% CO, 10% $H_2$, 30% $CO_2$ and 10% $N_2$); N=3-5; Error bar=S.D.

Figure 7A:
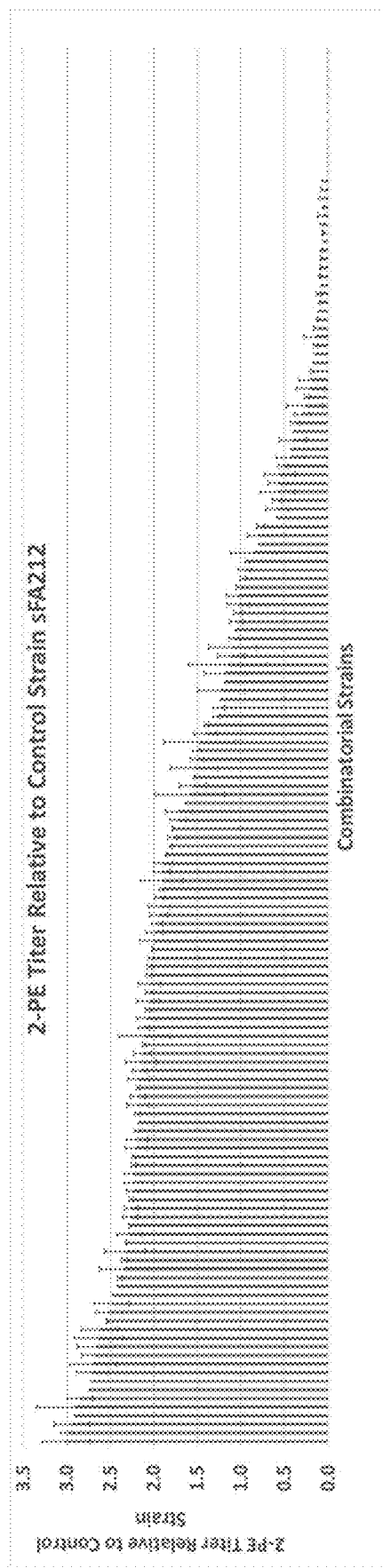
Figure 7B:
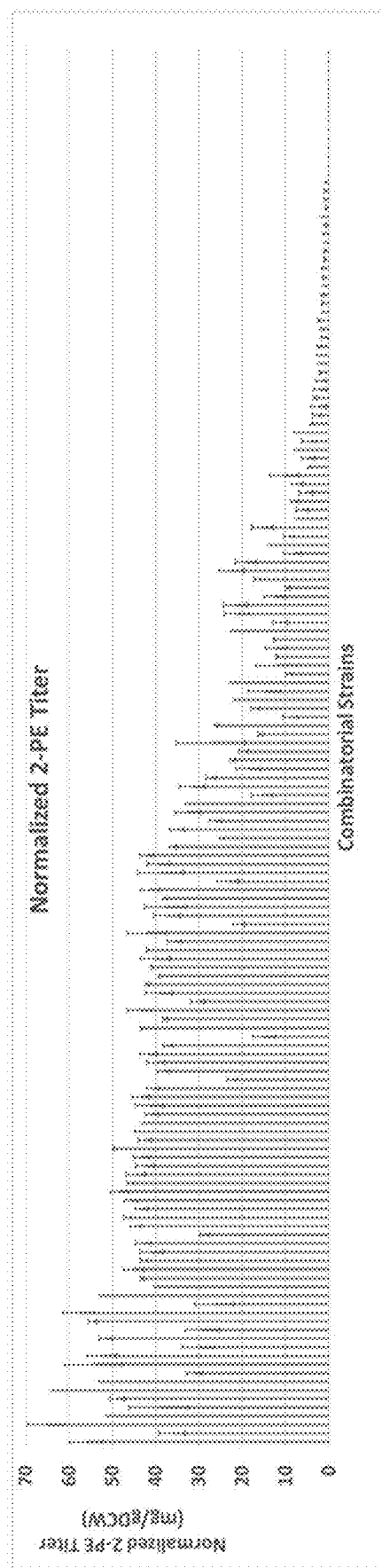
Figure 7C:
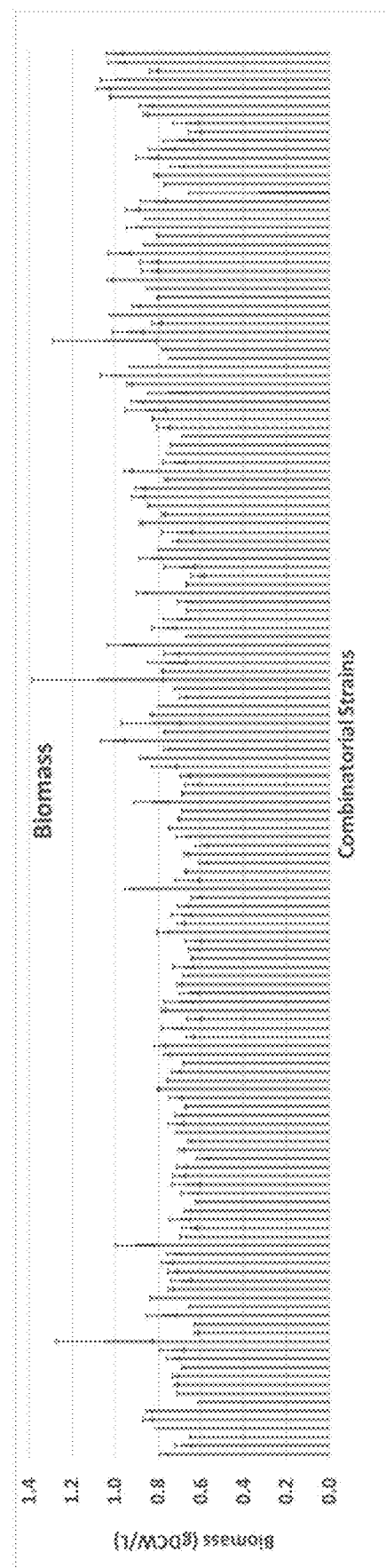

FIGS. 7A-C show characterization of 162 2-PE combinatorial strains in 12-well plates with 200 kPa synthetic gas blend (50% CO, 10% $H_2$, 30% $CO_2$, and 10% $N_2$). FIG. 7A: 2-PE titer relative to control strain sFA212; FIG. 7B: 2-PE titer normalized by biomass concentration; FIG. 7C: Biomass concentration; Incubation duration=8-10 days; N=2; Error bar=S.D.

Figure 8B:
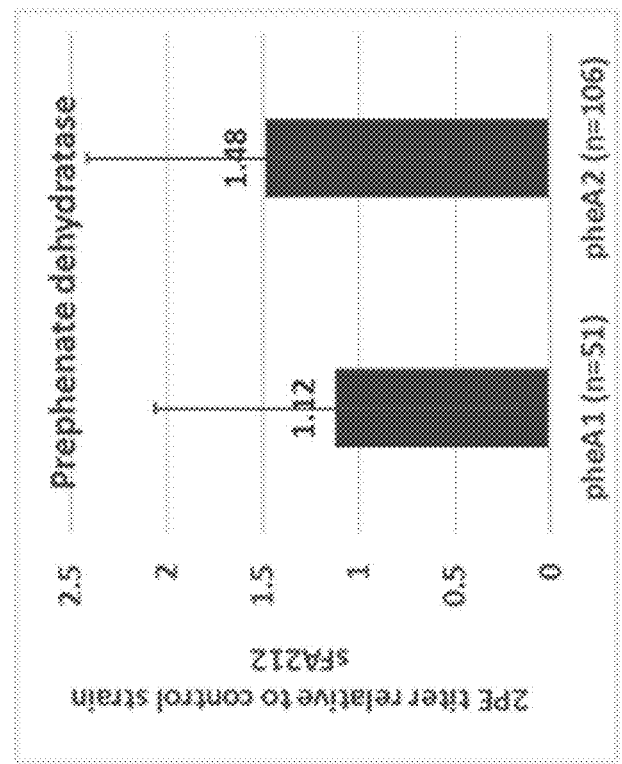
Figure 8A:
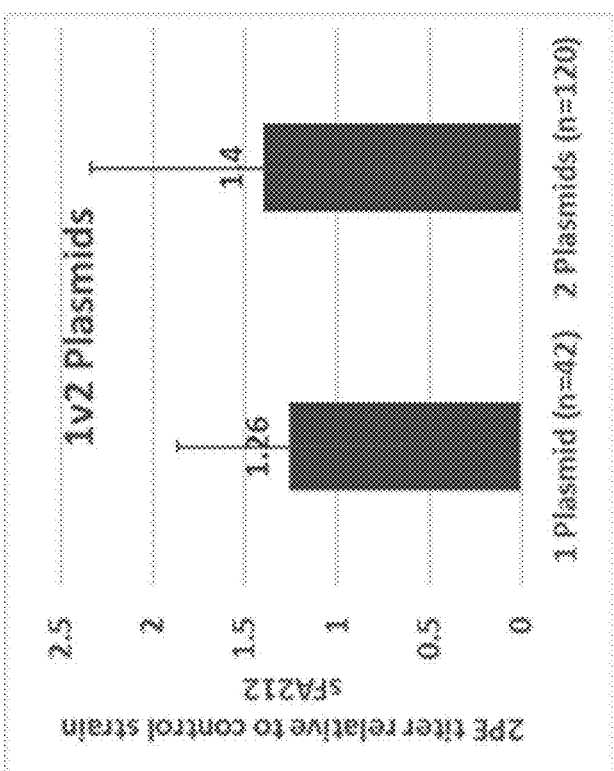
Figure 8D:
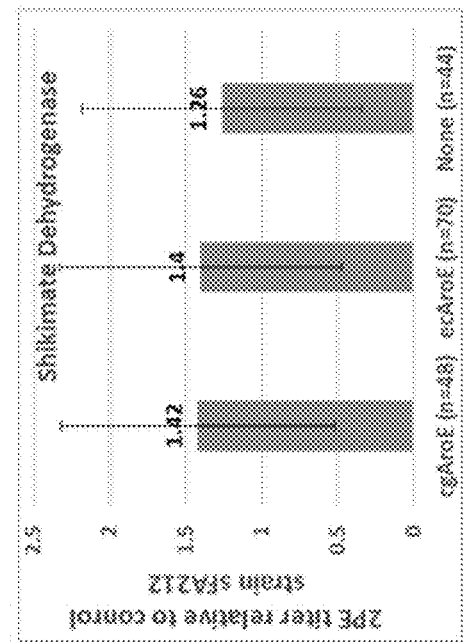
Figure 8C:
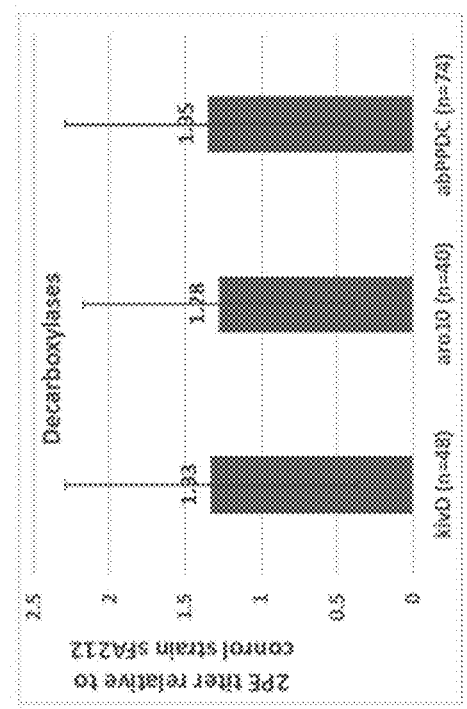
Figure 8E:
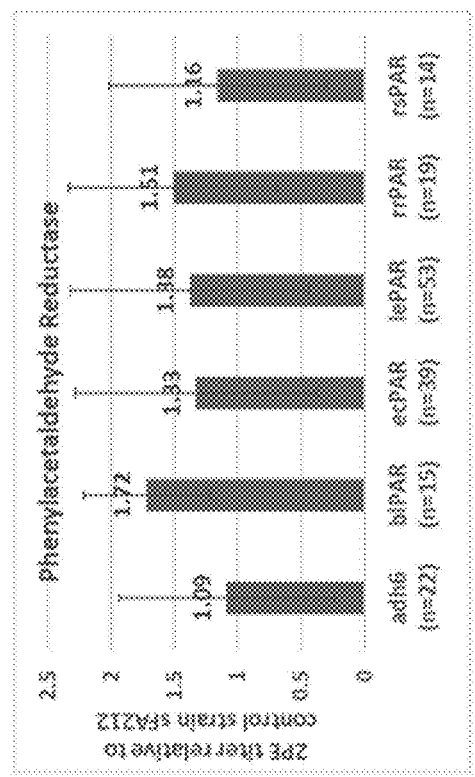

FIGS. 8A-E show comparisons of end-point 2-PE titers in combinatorial strains according to: number of plasmids (FIG. 8A); bi-functional chorismate mutase/prephenate dehydratase variants (FIG. 8B); decarboxylase variants (FIG. 8C); shikimate dehydrogenase variants (FIG. 8D); and phenylacetaldehyde reductase variants (FIG. 8E). Incubation duration=8-10 days; Error bar=S.D.

Figure 9A:
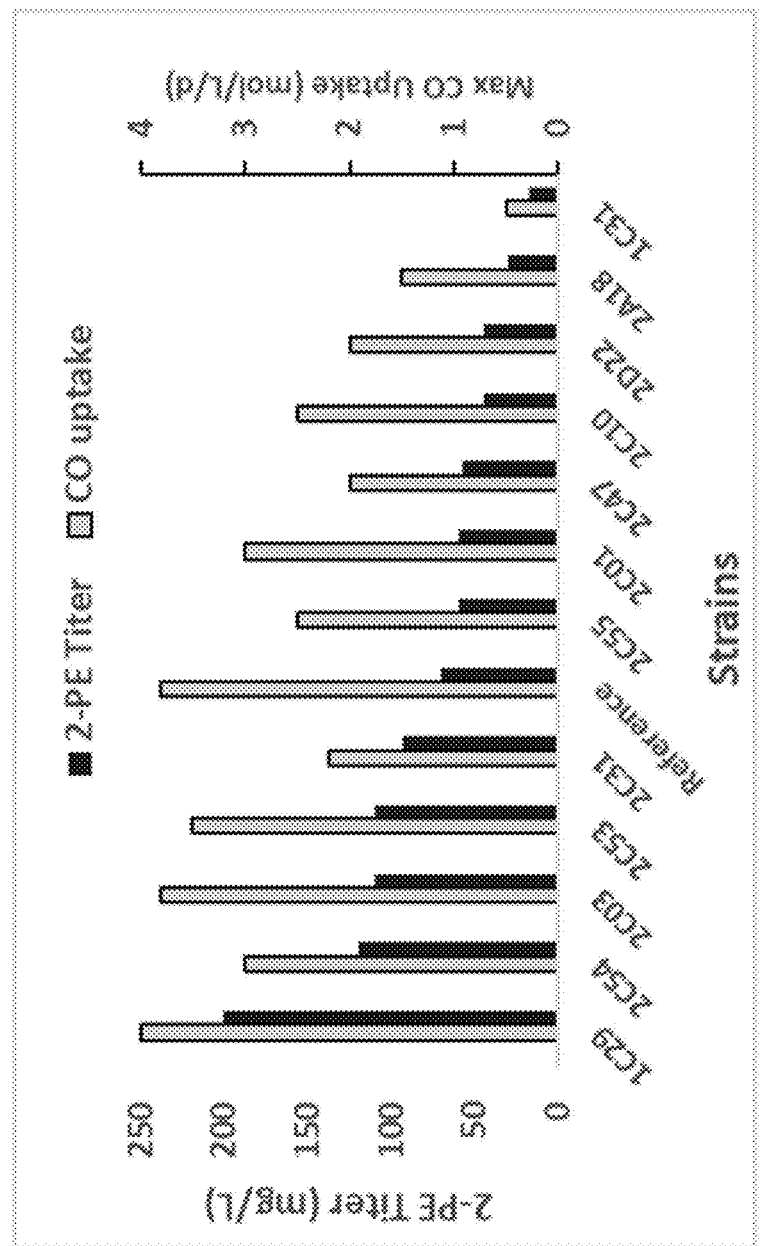
Figure 9B:
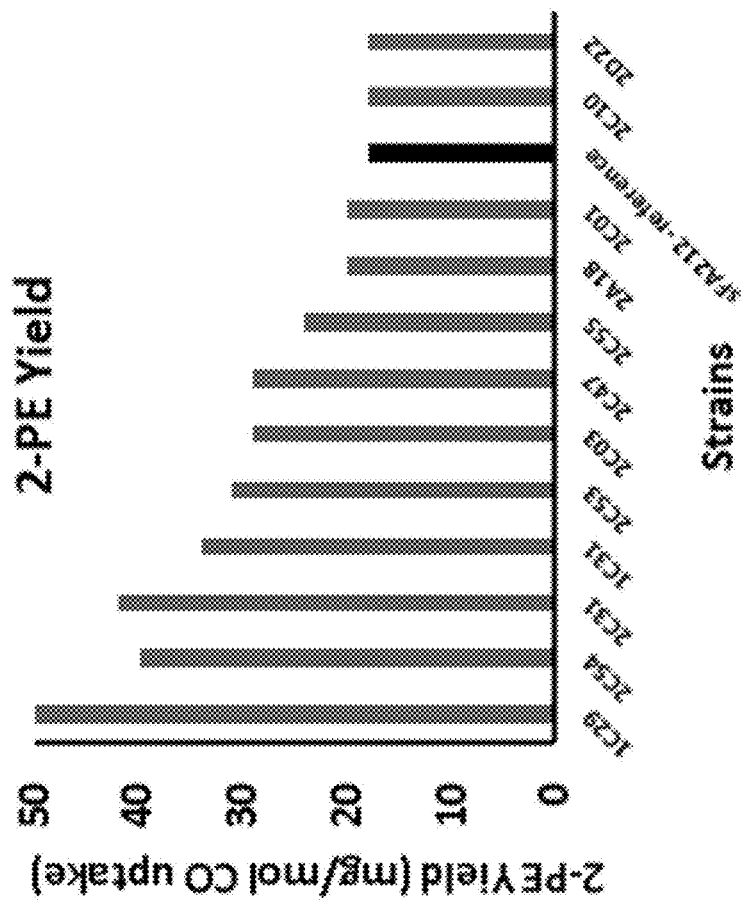

FIGS. 9A-B show characterization of 12 combinatorial strains in continuous CSTR fermentation using a synthetic gas blend (40% CO, 20% $H_2$, 20% $CO_2$, and 20% $N_2$). 2.9-fold increase in 2-PE titer relative to reference strain sFA212 was observed in strain 1C29. 10 strains achieved higher 2-PE yield when compared to the reference strain.

FIGS. 10A-B show 2-PE production of combinatorial strain 1C29 in two continuous CSTR runs with nitrogen limitation.

Figure 11A:
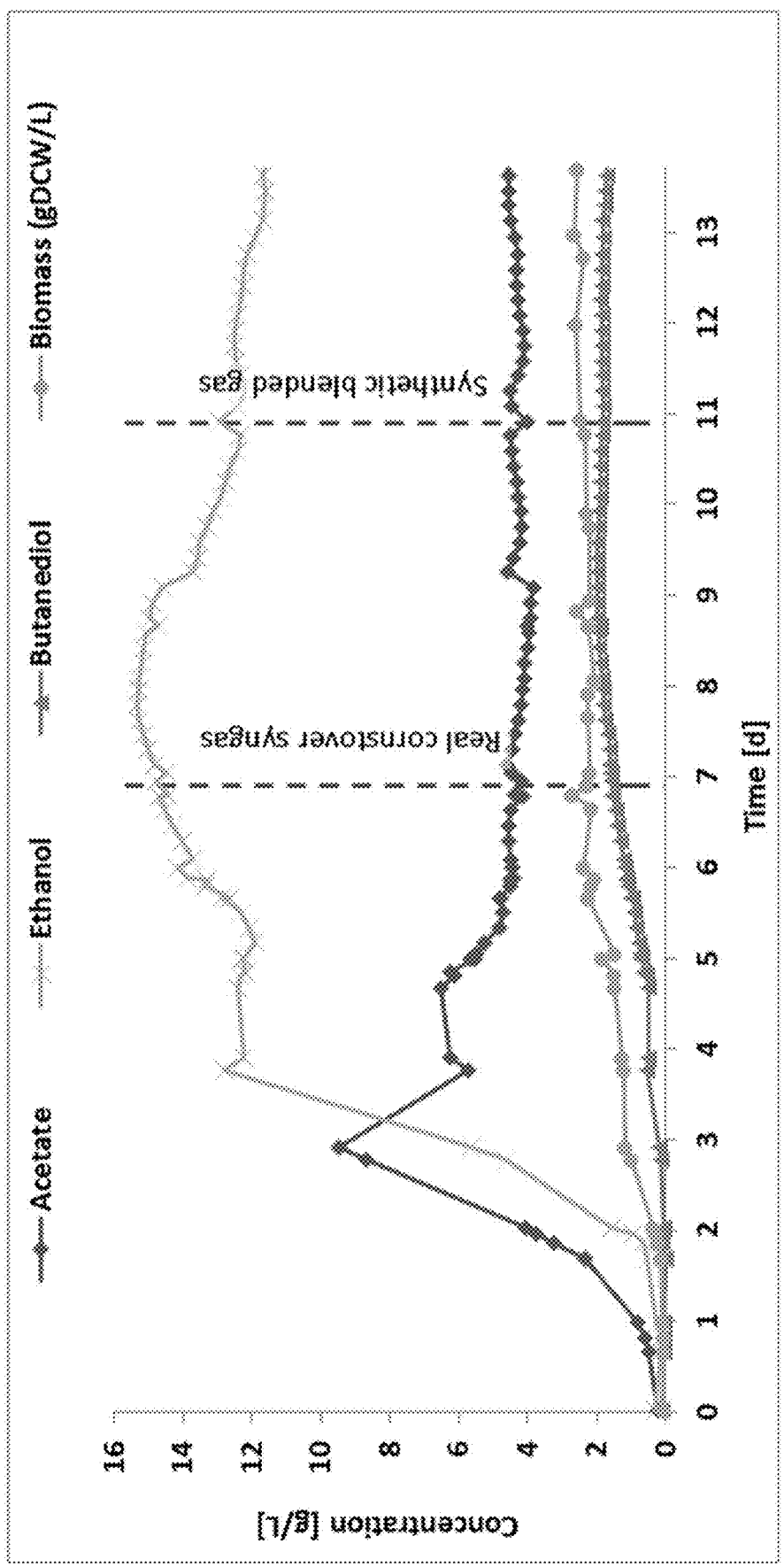
Figure 11B:
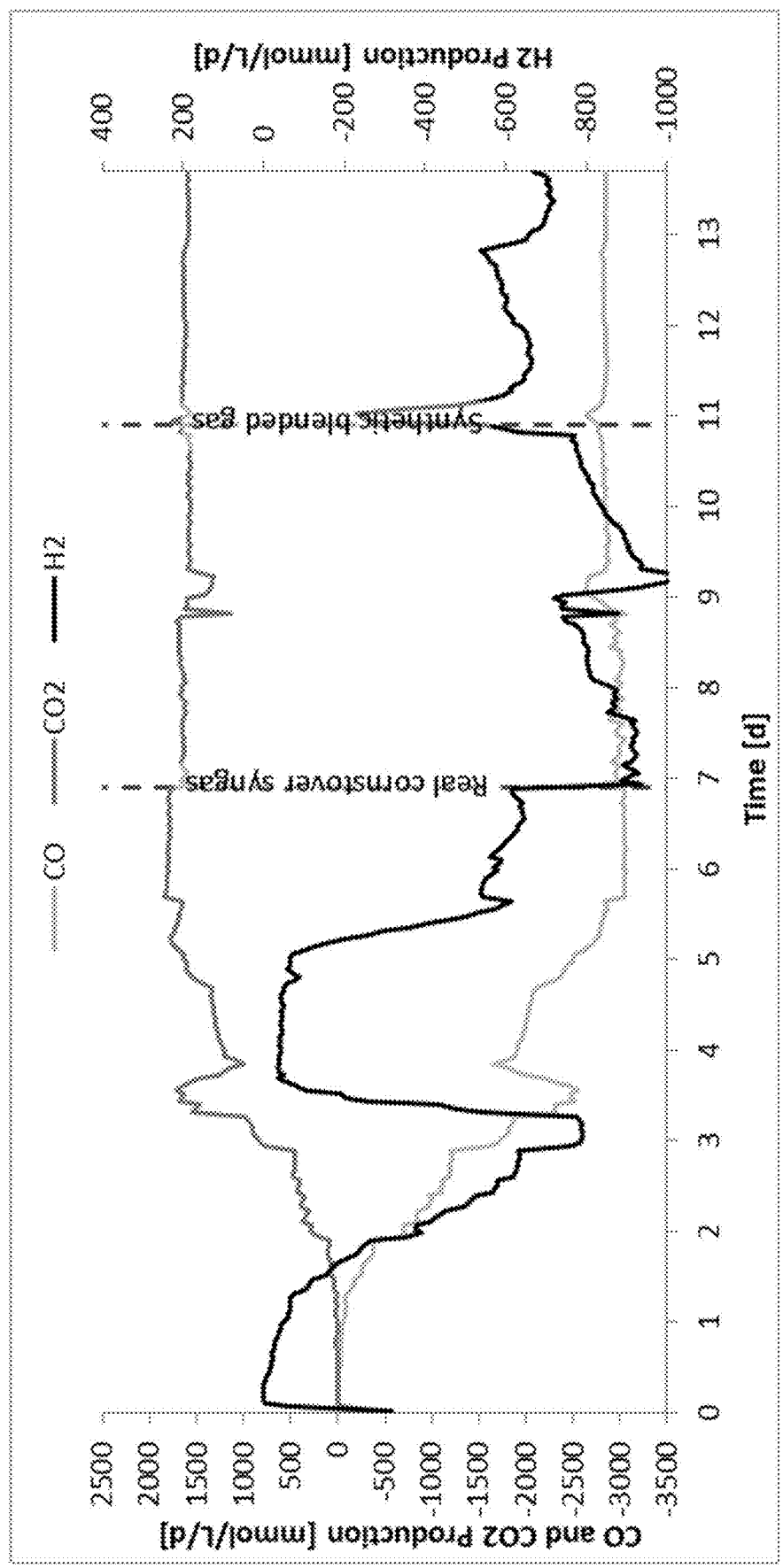
Figure 11C:
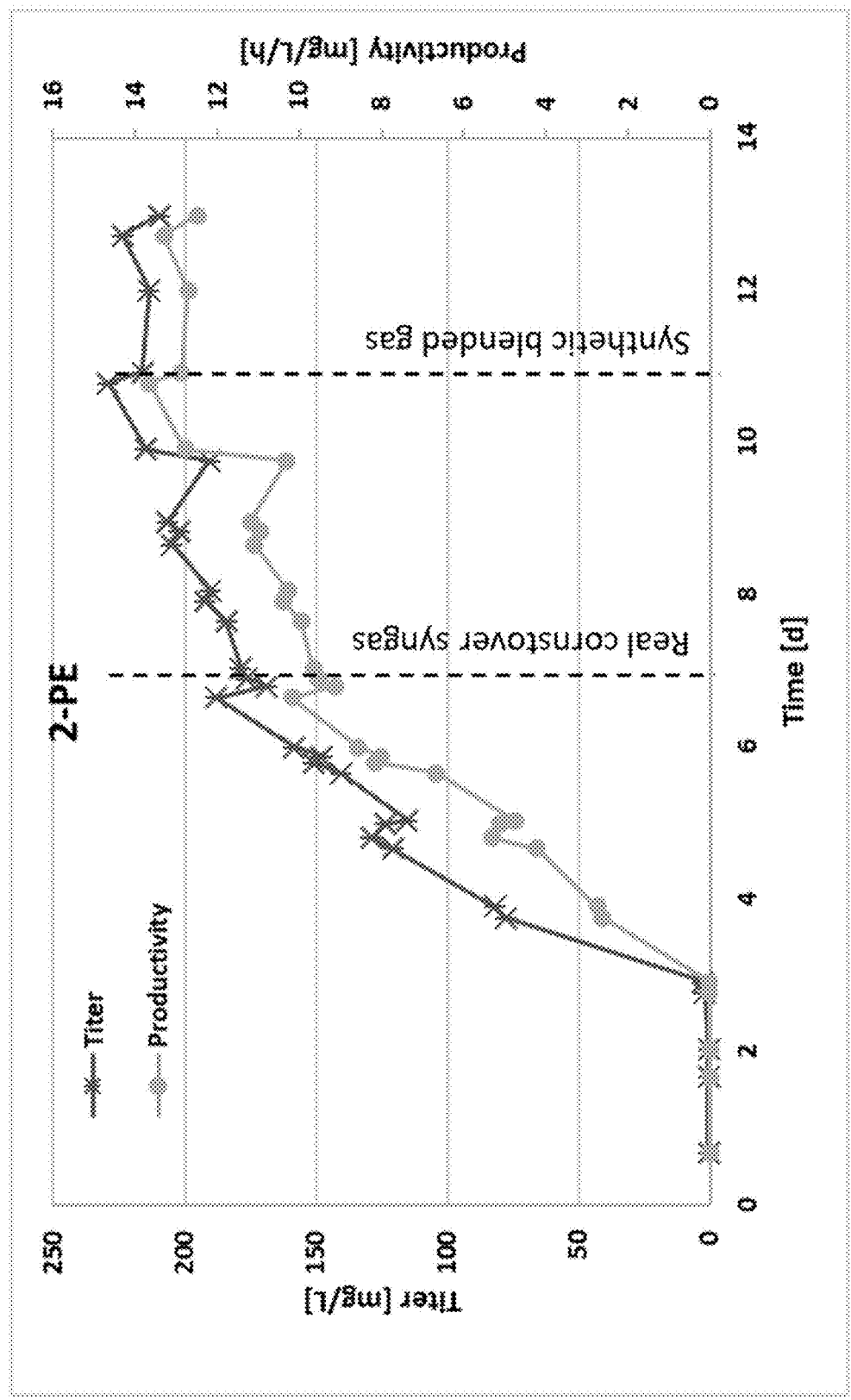

FIGS. 11A-C show results of testing the effect of pretreated corn stover-derived syngas (23.3% $H_2$, 38.7% CO, 19.6% $CO_2$, and 18.4% $N_2$) in continuous CSTR fermentation using strain sFA212. FIG. 11A: metabolite profile analyzed by HPLC; FIG. 11B: gas profile analyzed by GC-TCD (negative=uptake); FIG. 11C: 2-PE profile by analyzed GC-FID. Real syngas was used between day 6.9 and 10.9 (total of 4 days).

DETAILED DESCRIPTION

Disclosed herein are methods and compositions for de novo biosynthesis of 2-phenylethanol (2-PE) from syngas, which have potential to alleviate dependence on natural and petrochemical processes to manufacture 2-PE.

Definitions

Unless otherwise defined, the following terms as used throughout this specification are defined as follows:

The term "fermentation" should be interpreted as a metabolic process that produces chemical changes in a substrate. For example, a fermentation process receives one or more substrates and produces one or more products through utilization of one or more microorganisms. The term "fermentation," "gas fermentation" and the like should be interpreted as the process which receives one or more substrate, such as syngas produced by gasification and produces one or more product through the utilization of one or more C1-fixing microorganism. Preferably the fermentation process includes the use of one or more bioreactor. The fermentation process may be described as either "batch" or "continuous". "Batch fermentation" is used to describe a fermentation process where the bioreactor is filled with raw material, e.g. the carbon source, along with microorganisms, where the products remain in the bioreactor until fermentation is completed. In a "batch" process, after fermentation is completed, the products are extracted, and the bioreactor is cleaned before the next "batch" is started. "Continuous fermentation" is used to describe a fermentation process where the fermentation process is extended for longer periods of time, and product and/or metabolite is extracted during fermentation. Preferably the fermentation process is continuous.

The term "non-naturally occurring" when used in reference to a microorganism is intended to mean that the microorganism has at least one genetic modification not found in a naturally occurring strain of the referenced species, including wild-type strains of the referenced species. Non-naturally occurring microorganisms are typically developed in a laboratory or research facility.

The terms "genetic modification," "genetic alteration," or "genetic engineering" broadly refer to manipulation of the genome or nucleic acids of a microorganism by the hand of man. Likewise, the terms "genetically modified," "genetically altered," or "genetically engineered" refers to a microorganism containing such a genetic modification, genetic alteration, or genetic engineering. These terms may be used to differentiate a lab-generated microorganism from a naturally occurring microorganism. Methods of genetic modification of include, for example, heterologous gene expression, gene or promoter insertion or deletion, nucleic acid mutation, altered gene expression or inactivation, enzyme engineering, directed evolution, knowledge-based design, random mutagenesis methods, gene shuffling, and codon optimization.

Metabolic engineering of microorganisms, such as *Clostridia*, can tremendously expand their ability to produce many important fuel and chemical molecules other than native metabolites, such as ethanol. In recent years several different methods for genome engineering for *Clostridia* have been developed including intron-based methods (ClosTron) (Kuehne, *Strain Eng: Methods and Protocols*, 389-407, 2011), allelic exchange methods (ACE) (Heap, *Nucl Acids Res*, 40: e59, 2012; Ng, *PLoS One*, 8: e56051, 2013), Triple Cross (Liew, *Frontiers Microbiol*, 7: 694, 2016), methods mediated through I-SceI (Zhang, *Journal Microbiol Methods*, 108: 49-60, 2015), MazF (Al-Hinai, *Appl Environ Microbiol*, 78: 8112-8121, 2012), or others (Argyros, *Appl Environ Microbiol*, 77: 8288-8294, 2011), Cre-Lox (Ueki, mBio, 5: e01636-01614, 2014), and CRISPR/Cas9 (Nagaraju, Biotechnol Biofuels, 9: 219, 2016). However, it remains extremely challenging to iteratively introduce more than a few genetic changes, due to slow and laborious cycling times and limitations on the transferability of these genetic techniques across species. Furthermore, we do not yet sufficiently understand C1 metabolism in *Clostridia* to reliably predict modifications that will maximize C1 uptake, conversion, and carbon/energy/redox flows towards product synthesis. Accordingly, introduction of target pathways in *Clostridia* remains a tedious and time-consuming process.

"Recombinant" indicates that a nucleic acid, protein, or microorganism is the product of genetic modification, engineering, or recombination. Generally, the term "recombinant" refers to a nucleic acid, protein, or microorganism that contains or is encoded by genetic material derived from multiple sources, such as two or more different strains or species of microorganisms.

"Wild type" refers to the typical form of an organism, strain, gene, or characteristic as it occurs in nature, as distinguished from mutant or variant forms.

"Endogenous" or "native" refers to a nucleic acid or protein that is present or expressed in the wild-type or parental microorganism from which the microorganism of the disclosure is derived. For example, an endogenous gene is a gene that is natively present in the wild-type or parental microorganism from which the microorganism of the disclosure is derived. In one embodiment, the expression of an endogenous gene may be controlled by an exogenous regulatory element, such as an exogenous promoter.

"Exogenous" refers to a nucleic acid or protein that originates outside the microorganism of the disclosure. For example, an exogenous gene or enzyme may be artificially or recombinantly created and introduced to or expressed in the microorganism of the disclosure. An exogenous gene or enzyme may also be isolated from a heterologous microorganism and introduced to or expressed in the microorganism of the disclosure. Exogenous nucleic acids may be adapted to integrate into the genome of the microorganism of the disclosure or to remain in an extra-chromosomal state in the microorganism of the disclosure, for example, in a plasmid.

"Heterologous" refers to a nucleic acid or protein that is not present in the wild-type or parental microorganism from which the microorganism of the disclosure is derived. For example, a heterologous gene or enzyme may be derived from a different strain or species and introduced to or expressed in the microorganism of the disclosure. The heterologous gene or enzyme may be introduced to or expressed in the microorganism of the disclosure in the form in which it occurs in the different strain or species. Alternatively, the heterologous gene or enzyme may be modified in some way, e.g., by codon-optimizing it for expression in the microorganism of the disclosure or by engineering it to alter function, such as to reverse the direction of enzyme activity or to alter substrate specificity.

The terms "polynucleotide," "nucleotide," "nucleotide sequence," "nucleic acid," and "oligonucleotide" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides or nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene products."

The terms "polypeptide", "peptide," and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein, the term "amino acid" includes natural and/or unnatural or synthetic amino acids, including glycine and both the D or L optical isomers, and amino acid analogs and peptidomimetics.

"Enzyme activity," or simply "activity," refers broadly to enzymatic activity, including, but not limited, to the activity of an enzyme, the amount of an enzyme, or the availability of an enzyme to catalyze a reaction. Accordingly, "increasing" enzyme activity includes increasing the activity of an enzyme, increasing the amount of an enzyme, or increasing the availability of an enzyme to catalyze a reaction. Similarly, "decreasing" enzyme activity includes decreasing the activity of an enzyme, decreasing the amount of an enzyme, or decreasing the availability of an enzyme to catalyze a reaction.

"Codon optimization" refers to the mutation of a nucleic acid, such as a gene, for optimized or improved translation of the nucleic acid in a particular strain or species. Codon optimization may result in faster translation rates or higher translation accuracy.

"Overexpressed" refers to an increase in expression of a nucleic acid or protein in the microorganism of the disclosure compared to the wild-type or parental microorganism from which the microorganism of the disclosure is derived. Overexpression may be achieved by any means known in the art, including modifying gene copy number, gene transcription rate, gene translation rate, or enzyme degradation rate.

The term "variants" includes nucleic acids and proteins whose sequence varies from the sequence of a reference nucleic acid and protein, such as a sequence of a reference nucleic acid and protein disclosed in the prior art or exemplified herein. The methods and compositions of the disclosure may be practiced using variant nucleic acids or proteins that perform substantially the same function as the reference nucleic acid or protein. For example, a variant protein may perform substantially the same function or catalyze substantially the same reaction as a reference protein. A variant gene may encode the same or substantially the same protein as a reference gene. A variant promoter may have substantially the same ability to promote the expression of one or more genes as a reference promoter.

Such nucleic acids or proteins may be referred to herein as "functionally equivalent variants" or "functional homologues." By way of example, functionally equivalent variants of a nucleic acid may include allelic variants, fragments of a gene, mutated genes, polymorphisms, and the like. Homologous genes from other microorganisms are also examples of functionally equivalent variants. These include homologous genes in species such as *Clostridium acetobutylicum, Clostridium beijerinckii*, or *Clostridium ljungdahlii*, the details of which are publicly available on websites such as Genbank or NCBI. Functionally equivalent variants also include nucleic acids whose sequence varies as a result of codon optimization for a particular microorganism. A functionally equivalent variant of a nucleic acid will preferably have at least approximately 70%, approximately 80%, approximately 85%, approximately 90%, approximately 95%, approximately 98%, or greater nucleic acid sequence identity (percent homology) with the referenced nucleic acid. A functionally equivalent variant (i.e., a functional homologue) of a protein will preferably have at least approximately 70%, approximately 80%, approximately 85%, approximately 90%, approximately 95%, approximately 98%, or greater amino acid identity (percent homology) with the referenced protein. The functional equivalence of a variant nucleic acid or protein may be evaluated using any method known in the art.

Nucleic acid or amino acid sequence identity requires identical amino acid sequences between two aligned sequences. Thus, a candidate sequence sharing 80% nucleic acid or amino acid identity with a reference sequence requires that, following alignment, 80% of the nucleic acids or amino acids in the candidate sequence are identical to the corresponding nucleic acids or amino acids in the reference sequence. Identity according to the present invention is determined by aid of computer analysis, such as, without limitations, the ClustalW computer alignment program (Higgins et al., Nucleic Acids Res. 22:4673-4680), and the default parameters suggested therein. Using, for example, the ClustalW software with its default settings, the mature (bioactive) part of a query and a reference polypeptide are aligned. The number of fully conserved residues are counted and divided by the length of the reference polypeptide.

Nucleic acids may be delivered to a microorganism of the disclosure using any method known in the art. For example, nucleic acids may be delivered as naked nucleic acids or may be formulated with one or more agents, such as liposomes. The nucleic acids may be DNA, RNA, cDNA, or combinations thereof, as is appropriate. Restriction inhibitors may be used in certain embodiments. Additional vectors may include plasmids, viruses, bacteriophages, cosmids, and artificial chromosomes. In a preferred embodiment, nucleic acids are delivered to the microorganism of the disclosure using a plasmid. By way of example, transformation (including transduction or transfection) may be achieved by electroporation, ultrasonication, polyethylene glycol-mediated transformation, chemical or natural competence, protoplast transformation, prophage induction, or conjugation. In certain embodiments having active restriction enzyme systems, it may be necessary to methylate a nucleic acid before introduction of the nucleic acid into a microorganism.

Furthermore, nucleic acids may be designed to comprise a regulatory element, such as a promoter, to increase or otherwise control expression of a particular nucleic acid. The promoter may be a constitutive promoter or an inducible promoter. Ideally, the promoter is a Wood-Ljungdahl pathway promoter, a ferredoxin promoter, a pyruvate:ferredoxin oxidoreductase promoter, an Rnf complex operon promoter, an ATP synthase operon promoter, or a phosphotransacetylase/acetate kinase operon promoter.

A "microorganism" is a microscopic organism, especially a bacterium, archaeon, virus, or fungus. The microorganism of the disclosure is typically a bacterium. As used herein, recitation of "microorganism" should be taken to encompass "bacterium."

A "parental microorganism" is a microorganism used to generate a microorganism of the disclosure. The parental microorganism may be a naturally occurring microorganism (i.e., a wild-type microorganism) or a microorganism that has been previously modified (i.e., a mutant or recombinant microorganism). The microorganism of the disclosure may be modified to express or overexpress one or more enzymes that were not expressed or overexpressed in the parental microorganism. Similarly, the microorganism of the disclosure may be modified to contain one or more genes that were not contained by the parental microorganism. The microorganism of the disclosure may also be modified to not express or to express lower amounts of one or more enzymes that were expressed in the parental microorganism. In one embodiment, the parental microorganism is *Clostridium autoethanogenum*, *Clostridium ljungdahlii*, or *Clostridium ragsdalei*. In a preferred embodiment, the parental microorganism is *Clostridium autoethanogenum* LZ1561, which was deposited with Deutsche Sammlung von Mikroorganismen and Zellkulturen GmbH (DSMZ) located at Inhoffenstraße 7B, D-38124 Braunschweig, Germany on Jun. 7, 2010 under the terms of the Budapest Treaty and accorded accession number DSM23693. This strain is described in International Patent Application No. PCT/NZ2011/000144, which published as WO 2012/015317.

The term "derived from" indicates that a nucleic acid, protein, or microorganism is modified or adapted from a different (e.g., a parental or wild-type) nucleic acid, protein, or microorganism, so as to produce a new nucleic acid, protein, or microorganism. Such modifications or adaptations typically include insertion, deletion, mutation, or substitution of nucleic acids or genes. Generally, the microorganism of the disclosure is derived from a parental microorganism. In one embodiment, the microorganism of the disclosure is derived from *Clostridium autoethanogenum*, *Clostridium ljungdahlii*, or *Clostridium ragsdalei*. In a preferred embodiment, the microorganism of the disclosure is derived from *Clostridium autoethanogenum* LZ1561, which is deposited under DSMZ accession number DSM23693.

The microorganism of the disclosure may be further classified based on functional characteristics. For example, the microorganism of the disclosure may be or may be derived from a C1-fixing microorganism, an anaerobe, an acetogen, an ethanologen, a carboxydotroph, and/or a methanotroph. Table 1 provides a representative list of microorganisms and identifies their functional characteristics.

TABLE 1

|  | Wood-Ljungdahl | C1-fixing | Anaerobe | Acetogen | Ethanologen | Autotroph | Carboxydotroph |
|---|---|---|---|---|---|---|---|
| *Acetobacterium woodii* | + | + | + | + | +/− [1] | + | − |
| *Alkalibaculum bacchii* | + | + | + | + | + | + | + |
| *Blautia producta* | + | + | + | + | − | + | + |
| *Butyribacterium methylotrophicum* | + | + | + | + | + | + | + |
| *Clostridium aceticum* | + | + | + | + | − | + | + |
| *Clostridium autoethanogenum* | + | + | + | + | + | + | + |
| *Clostridium carboxidivorans* | + | + | + | + | + | + | + |
| *Clostridium coskatii* | + | + | + | + | + | + | + |
| *Clostridium drakei* | + | + | + | + | − | + | + |
| *Clostridium formicoaceticum* | + | + | + | + | − | + | + |
| *Clostridium ljungdahlii* | + | + | + | + | + | + | + |
| *Clostridium magnum* | + | + | + | + | − | + | +/− [2] |
| *Clostridium ragsdalei* | + | + | + | + | + | + | + |
| *Clostridium scatologenes* | + | + | + | + | − | + | + |
| *Eubacterium limosum* | + | + | + | + | − | + | + |
| *Moorella thermautotrophica* | + | + | + | + | + | + | + |
| *Moorella thermoacetica* (formerly *Clostridium thermoaceticum*) | + | + | + | + | − [3] | + | + |
| *Oxobacter pfennigii* | + | + | + | + | − | + | + |
| *Sporomusa ovata* | + | + | + | + | − | + | +/− [4] |
| *Sporomusa silvacetica* | + | + | + | + | − | + | +/− [5] |
| *Sporomusa sphaeroides* | + | + | + | + | − | + | +/− [6] |
| *Thermoanaerobacter kivui* | + | + | + | + | − | + | − |

[1] *Acetobacterium woodii* can produce ethanol from fructose, but not from gas.
[2] It has not been investigated whether *Clostridium magnum* can grow on CO.
[3] One strain of *Moorella thermoacetica*, *Moorella* sp. HUC22-1, has been reported to produce ethanol from gas.
[4] It has not been investigated whether *Sporomusa ovata* can grow on CO.
[5] It has not been investigated whether *Sporomusa silvacetica* can grow on CO.
[6] It has not been investigated whether *Sporomusa sphaeroides* can grow on CO.

"Wood-Ljungdahl" refers to the Wood-Ljungdahl pathway of carbon fixation as described, e.g., by Ragsdale, *Biochim Biophys Acta*, 1784: 1873-1898, 2008. "Wood-Ljungdahl microorganisms" refers, predictably, to microorganisms containing the Wood-Ljungdahl pathway. Generally, the microorganism of the disclosure contains a native Wood-Ljungdahl pathway. Herein, a Wood-Ljungdahl pathway may be a native, unmodified Wood-Ljungdahl pathway or it may be a Wood-Ljungdahl pathway with some degree of genetic modification (e.g., overexpression, heterologous expression, knockout, etc.) so long as it still functions to convert CO, $CO_2$, and/or $H_2$ to acetyl-CoA.

"C1" refers to a one-carbon molecule, for example, CO, $CO_2$, $CH_4$, or $CH_3OH$. "C1-oxygenate" refers to a one-carbon molecule that also comprises at least one oxygen atom, for example, CO, $CO_2$, or $CH_3OH$. "C1-carbon source" refers a one carbon-molecule that serves as a partial or sole carbon source for the microorganism of the disclosure. For example, a C1-carbon source may comprise one or more of CO, $CO_2$, $CH_4$, $CH_3OH$, or $CH_2O_2$. Preferably, the C1-carbon source comprises one or both of CO and $CO_2$. A "C1-fixing microorganism" is a microorganism that has the ability to produce one or more products from a C1 carbon source. Typically, the microorganism of the disclosure is a C1-fixing bacterium. In a preferred embodiment, the microorganism of the disclosure is derived from a C1-fixing microorganism identified in Table 1.

An "anaerobe" is a microorganism that does not require oxygen for growth. An anaerobe may react negatively or even die if oxygen is present above a certain threshold. However, some anaerobes are capable of tolerating low levels of oxygen (e.g., 0.000001-5% oxygen). Typically, the microorganism of the disclosure is an anaerobe. In some embodiments, the microorganism of the disclosure is derived from an anaerobe identified in Table 1.

"Acetogens" are obligately anaerobic bacteria that use the Wood-Ljungdahl pathway as their main mechanism for energy conservation and for synthesis of acetyl-CoA and acetyl-CoA-derived products, such as acetate (Ragsdale, *Biochim Biophys Acta*, 1784: 1873-1898, 2008). In particular, acetogens use the Wood-Ljungdahl pathway as a (1) mechanism for the reductive synthesis of acetyl-CoA from $CO_2$, (2) terminal electron-accepting, energy conserving process, (3) mechanism for the fixation (assimilation) of $CO_2$ in the synthesis of cell carbon (Drake, Acetogenic Prokaryotes, In: The Prokaryotes, 3rd edition, p. 354, New York, N.Y., 2006). All naturally occurring acetogens are C1-fixing, anaerobic, autotrophic, and non-methanotrophic. Typically, the microorganism of the disclosure is an acetogen. In a preferred embodiment, the microorganism of the disclosure is derived from an acetogen identified in Table 1.

An "ethanologen" is a microorganism that produces or is capable of producing ethanol. Typically, the microorganism of the disclosure is an ethanologen. In a preferred embodiment, the microorganism of the disclosure is derived from an ethanologen identified in Table 1.

An "autotroph" is a microorganism capable of growing in the absence of organic carbon. Instead, autotrophs use inorganic carbon sources, such as CO and/or $CO_2$. Typically, the microorganism of the disclosure is an autotroph. In a preferred embodiment, the microorganism of the disclosure is derived from an autotroph identified in Table 1.

A "carboxydotroph" is a microorganism capable of utilizing CO as a sole source of carbon and energy. Typically, the microorganism of the disclosure is a carboxydotroph. In a preferred embodiment, the microorganism of the disclosure is derived from a carboxydotroph identified in Table 1.

A "methanotroph" is a microorganism capable of utilizing methane as a sole source of carbon and energy. In certain embodiments, the microorganism of the disclosure is a methanotroph or is derived from a methanotroph. In other embodiments, the microorganism of the disclosure is not a methanotroph or is not derived from a methanotroph.

More broadly, the microorganism of the disclosure may be derived from any genus or species identified in Table 1. For example, the microorganism may be a member of a genus selected from the group consisting of *Acetobacterium, Alkalibaculum, Blautia, Butyribacterium, Clostridium, Eubacterium, Moorella, Oxobacter, Sporomusa*, and *Thermoanaerobacter*. In particular, the microorganism may be derived from a parental bacterium selected from the group consisting of *Acetobacterium woodii, Alkalibaculum bacchii, Blautia producta, Butyribacterium methylotrophicum, Clostridium aceticum, Clostridium autoethanogenum, Clostridium carboxidivorans, Clostridium coskatii, Clostridium drakei, Clostridium formicoaceticum, Clostridium ljungdahlii, Clostridium magnum, Clostridium ragsdalei, Clostridium scatologenes, Eubacterium limosum, Moorella thermautotrophica, Moorella thermoacetica, Oxobacter pfennigii, Sporomusa ovata, Sporomusa silvacetica, Sporomusa sphaeroides*, and *Thermoanaerobacter kivui*.

These types of microorganisms are known to live in the thermodynamic limit of life (Schuchmann, *Nat Rev Microbiol*, 12: 809-821, 2014) so, prior to the present invention, it was unknown whether they would be capable of synthesizing a C8 aromatic alcohol at all, much less in a meaningful quantity, especially given the potential for 2-PE to have toxic effects on these microorganisms.

In a preferred embodiment, the microorganism of the disclosure is derived from the cluster of *Clostridia* comprising the species *Clostridium autoethanogenum, Clostridium ljungdahlii*, and *Clostridium ragsdalei*. These species were first reported and characterized by Abrini, *Arch Microbiol*, 161: 345-351, 1994 (*Clostridium autoethanogenum*), Tanner, *Int J System Bacteriol*, 43: 232-236, 1993 (*Clostridium ljungdahlii*), and Huhnke, WO 2008/028055 (*Clostridium ragsdalei*).

These three species have many similarities. In particular, these species are all C1 fixing, anaerobic, acetogenic, ethanologenic, and carboxydotrophic members of the genus *Clostridium*. These species have similar genotypes and phenotypes and modes of energy conservation and fermentative metabolism. Moreover, these species are clustered in clostridial rRNA homology group I with 16S rRNA DNA that is more than 99% identical, have a DNA G+C content of about 22-30 mol %, are Gram-positive, have similar morphology and size (logarithmic growing cells between 0.5-0.7×3-5 μm), are mesophilic (grow optimally at 30-37° C.), have similar pH ranges of about 4-7.5 (with an optimal pH of about 5.5-6), lack cytochromes, and conserve energy via an Rnf complex. Also, reduction of carboxylic acids into their corresponding alcohols has been shown in these species (Perez, *Biotechnol Bioeng*, 110:1066-1077, 2012). Importantly, these species also all show strong autotrophic growth on CO-containing gases, produce ethanol and acetate (or acetic acid) as main fermentation products, and produce small amounts of 2,3-butanediol and lactic acid under certain conditions.

However, these three species also have a number of differences. These species were isolated from different sources: *Clostridium autoethanogenum* from rabbit gut, *Clostridium ljungdahlii* from chicken yard waste, and *Clostridium ragsdalei* from freshwater sediment. These species differ in utilization of various sugars (e.g., rhamnose, arabinose), acids (e.g., gluconate, citrate), amino acids (e.g., arginine, histidine), and other substrates (e.g., betaine, butanol). Moreover, these species differ in auxotrophy to certain vitamins (e.g., thiamine, biotin). These species have differences in nucleic and amino acid sequences of Wood-Ljungdahl pathway genes and proteins, although the general organization and number of these genes and proteins has been found to be the same in all species (Kopke, *Curr Opin Biotechnol*, 22: 320-325, 2011).

Thus, in summary, many of the characteristics of *Clostridium autoethanogenum, Clostridium ljungdahlii*, or *Clostridium ragsdalei* are not specific to that species, but are rather general characteristics for this cluster of C1 fixing, anaerobic, acetogenic, ethanologenic, and carboxydotrophic members of the genus *Clostridium*. However, since these species are, in fact, distinct, the genetic modification or manipulation of one of these species may not have an identical effect in another of these species. For instance, differences in growth, performance, or product production may be observed.

"Substrate" refers to a carbon and/or energy source for the microorganism of the disclosure. Typically, the substrate is gaseous and comprises a C1-carbon source, for example, CO, $CO_2$, and/or $CH_4$. Preferably, the substrate comprises a C1-carbon source of CO or CO+$CO_2$. The substrate may further comprise other non-carbon components, such as $H_2$, $N_2$, or electrons.

The substrate generally comprises at least some amount of CO, such as about 1, 2, 5, 10, 20, 30, 40, 50, 60, 70, 80, 90, or 100 mol % CO. The substrate may comprise a range of CO, such as about 20-80, 30-70, or 40-60 mol % CO. Preferably, the substrate comprises about 40-70 mol % CO (e.g., steel mill or blast furnace gas), about 20-30 mol % CO (e.g., basic oxygen furnace gas), or about 15-45 mol % CO (e.g., syngas). In some embodiments, the substrate may comprise a relatively low amount of CO, such as about 1-10 or 1-20 mol % CO. The microorganism of the disclosure typically converts at least a portion of the CO in the substrate to a product. In some embodiments, the substrate comprises no or substantially no (<1 mol %) CO.

The substrate may comprise some amount of $H_2$. For example, the substrate may comprise about 1, 2, 5, 10, 15, 20, or 30 mol % $H_2$. In some embodiments, the substrate may comprise a relatively high amount of $H_2$, such as about 60, 70, 80, or 90 mol % $H_2$. In further embodiments, the substrate comprises no or substantially no (<1 mol %) $H_2$.

The substrate may comprise some amount of $CO_2$. For example, the substrate may comprise about 1-80 or 1-30 mol % $CO_2$. In some embodiments, the substrate may comprise less than about 20, 15, 10, or 5 mol % $CO_2$. In another embodiment, the substrate comprises no or substantially no (<1 mol %) $CO_2$.

Although the substrate is typically gaseous, the substrate may also be provided in alternative forms. For example, the substrate may be dissolved in a liquid saturated with a CO-containing gas using a microbubble dispersion generator. By way of further example, the substrate may be adsorbed onto a solid support.

The substrate and/or C1-carbon source may be a waste gas obtained as a byproduct of an industrial process or from some other source, such as from automobile exhaust fumes, electrolysis, pyrolysis, torrefaction, or gasification. For example, waste material may be recycled by pyrolysis, torrefaction, or gasification to generate the substrate and/or C1-carbon source. In certain embodiments, the industrial process is selected from the group consisting of ferrous metal products manufacturing, such as a steel mill manufacturing, non-ferrous products manufacturing, petroleum refining, coal gasification, electric power production, carbon black production, paper and pulp manufacturing, black liquor gasification, ammonia production, methanol production, and coke manufacturing. In these embodiments, the substrate and/or C1-carbon source may be captured from the industrial process before it is emitted into the atmosphere, using any convenient method.

The substrate and/or C1-carbon source may be syngas, such as syngas obtained by gasification of coal or refinery residues, gasification of biomass or lignocellulosic material, or reforming of natural gas. In another embodiment, the syngas may be obtained from the gasification of municipal solid waste or industrial solid waste.

The composition of the substrate may have a significant impact on the efficiency and/or cost of the reaction. For example, the presence of oxygen (02) may reduce the efficiency of an anaerobic fermentation process. Depending on the composition of the substrate, it may be desirable to treat, scrub, or filter the substrate to remove any undesired impurities, such as toxins, undesired components, or dust particles, and/or increase the concentration of desirable components.

In certain embodiments, the fermentation is performed in the absence of carbohydrate substrates, such as sugar, starch, lignin, cellulose, or hemicellulose.

The microorganism of the disclosure may be cultured with the gaseous substrate to produce one or more products. For instance, the microorganism of the disclosure may produce or may be engineered to produce ethanol (WO 2007/117157), acetate (WO 2007/117157), 1-butanol (WO 2008/115080, WO 2012/053905, and WO 2017/066498), butyrate (WO 2008/115080), 2,3-butanediol (WO 2009/151342 and WO 2016/094334), lactate (WO 2011/112103), butene (WO 2012/024522), butadiene (WO 2012/024522), methyl ethyl ketone (2-butanone) (WO 2012/024522 and WO 2013/185123), ethylene (WO 2012/026833), acetone (WO 2012/115527), isopropanol (WO 2012/115527), lipids (WO 2013/036147), 3-hydroxypropionate (3-HP) (WO 2013/180581), terpenes, including isoprene (WO 2013/180584), fatty acids (WO 2013/191567), 2-butanol (WO 2013/185123), 1,2-propanediol (WO 2014/036152), 1-propanol (WO 2017/066498), 1-hexanol (WO 2017/066498), 1-octanol (WO 2017/066498), chorismate-derived products (WO 2016/191625), 3-hydroxybutyrate (WO 2017/066498), 1,3-butanediol (WO 2017/066498), 2-hydroxyisobutyrate or 2-hydroxyisobutyric acid (WO 2017/066498), isobutylene (WO 2017/066498), adipic acid (WO 2017/066498), 1,3-hexanediol (WO 2017/066498), 3-methyl-2-butanol (WO 2017/066498), 2-buten-1-ol (WO 2017/066498), isovalerate (WO 2017/066498), isoamyl alcohol (WO 2017/066498), and/or monoethylene glycol (WO 2019/126400) in addition to 2-phenylethanol. In certain embodiments, microbial biomass itself may be considered a product. These products may be further converted to produce at least one component of diesel, jet fuel, and/or gasoline. In certain embodiments, 2-phenylethanol may be used as an ingredient in fragrances, essential oils, flavors, and soaps. Additionally, the microbial biomass may be further processed to produce a single cell protein (SCP).

A "native product" is a product produced by a genetically unmodified microorganism. For example, ethanol, acetate, and 2,3-butanediol are native products of *Clostridium autoethanogenum, Clostridium ljungdahlii*, and *Clostridium ragsdalei*. A "non-native product" is a product that is produced by a genetically modified microorganism but is not produced by a genetically unmodified microorganism from which the genetically modified microorganism is derived.

"Selectivity" refers to the ratio of the production of a target product to the production of all fermentation products produced by a microorganism. The microorganism of the disclosure may be engineered to produce products at a certain selectivity or at a minimum selectivity. In one embodiment, a target product account for at least about 5%, 10%, 15%, 20%, 30%, 50%, or 75% of all fermentation products produced by the microorganism of the disclosure. In one embodiment, the target product accounts for at least 10% of all fermentation products produced by the microorganism of the disclosure, such that the microorganism of the disclosure has a selectivity for the target product of at least 10%. In another embodiment, the target product accounts for at least 30% of all fermentation products produced by the microorganism of the disclosure, such that the microorganism of the disclosure has a selectivity for the target product of at least 30%.

"Increasing the efficiency," "increased efficiency," and the like include, but are not limited to, increasing growth rate, product production rate or volume, product volume per volume of substrate consumed, or product selectivity. Efficiency may be measured relative to the performance of parental microorganism from which the microorganism of the disclosure is derived.

Typically, the culture is performed in a bioreactor. The term "bioreactor" includes a culture/fermentation device consisting of one or more vessels, towers, or piping arrangements, such as a continuous stirred tank reactor (CSTR), immobilized cell reactor (ICR), trickle bed reactor (TBR), bubble column, gas lift fermenter, static mixer, or other vessel or other device suitable for gas-liquid contact. In some embodiments, the bioreactor may comprise a first growth reactor and a second culture/fermentation reactor. The substrate may be provided to one or both of these reactors. As used herein, the terms "culture" and "fermentation" are used interchangeably. These terms encompass both the growth phase and product biosynthesis phase of the culture/fermentation process.

The culture is generally maintained in an aqueous culture medium that contains nutrients, vitamins, and/or minerals sufficient to permit growth of the microorganism. Preferably the aqueous culture medium is an anaerobic microbial growth medium, such as a minimal anaerobic microbial growth medium. Suitable media are well known in the art.

The culture/fermentation should desirably be carried out under appropriate conditions for production of the target product. Typically, the culture/fermentation is performed under anaerobic conditions. Reaction conditions to consider include pressure (or partial pressure), temperature, gas flow rate, liquid flow rate, media pH, media redox potential, agitation rate (if using a continuous stirred tank reactor), inoculum level, maximum gas substrate concentrations to ensure that gas in the liquid phase does not become limiting, and maximum product concentrations to avoid product inhibition. In particular, the rate of introduction of the substrate may be controlled to ensure that the concentration of gas in the liquid phase does not become limiting, since products may be consumed by the culture under gas-limited conditions.

In certain embodiments, the fermentation is performed in the absence of light or in the presence of an amount of light insufficient to meet the energetic requirements of photosynthetic microorganisms. In certain embodiments, the microorganism of the disclosure is a non-photosynthetic microorganism.

In some embodiments, 2-phenylethanol may be separated or purified from a fermentation broth using any method or combination of methods known in the art, including, for example, fractional distillation, evaporation, pervaporation, gas stripping, phase separation, and extractive fermentation, including, for example, liquid-liquid extraction. In certain embodiments, 2-phenylethanol is recovered from the fermentation broth by continuously removing a portion of the broth from the bioreactor, separating microbial cells from the broth (conveniently by filtration), and recovering 2-phenylethanol from the broth. Generally, alcohols and/or acetone may be recovered, for example, by distillation. Separated microbial cells are preferably recycled back to the bioreactor. The cell-free permeate remaining after 2-phenylethanol has been removed is also preferably returned to the bioreactor. Additional nutrients may be added to the cell-free permeate to replenish the medium before it is returned to the bioreactor.

Embodiments

In one embodiment, the disclosure provides a microorganism capable of producing 2-phenylethanol, wherein the microorganism comprises a heterologous enzyme that converts phenylpyruvate to phenylacetaldehyde and a heterologous enzyme that converts phenylacetaldehyde to 2-phenylethanol.

In some embodiments, the heterologous enzyme that converts phenylpyruvate to phenylacetaldehyde is decarboxylase and the heterologous enzyme that converts phenylacetaldehyde to 2-phenylethanol is phenylacetaldehyde reductase. In particular, the decarboxylase may be a phenylpyruvate-specific decarboxylase. In some embodiments, the nucleic acid encoding a heterologous decarboxylase enzyme comprises aro10 (from *Saccharomyces cerevisiae*) or abPPDC (from *Azospirillum brasilense*). In some embodiments, the nucleic acid encoding a heterologous decarboxylase enzyme comprises: (i) SEQ ID NO: 1, 2, or 4; (ii) a nucleic acid with at least 90% identity to SEQ ID NO: 1, 2, or 4 that encodes a decarboxylase enzyme that is functionally homologous to the decarboxylase enzyme encoded by SEQ ID NO: 1, 2, or 4; or (iii) a nucleic acid that encodes a functionally homologous polypeptide with at least 90% identity to the decarboxylase enzyme encoded by SEQ ID NO: 1, 2, or 4.

In some embodiments, the nucleic acid encoding a heterologous decarboxylase enzyme comprises aro10, abPPDC, or SEQ ID NO: 1, 2, or 4, or a functional homologue thereof sharing, for example, at least 70%, or at least 75%, or at least 80%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% nucleic acid sequence identity therewith. In some embodiments, the nucleic acid encoding a heterologous decarboxylase enzyme encodes a functionally homologous polypeptide sharing, for example, at least 70%, or at least 75%, or at least 80%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% polypeptide sequence identity to the decarboxylase enzyme encoded by aro10, abPPDC, or SEQ ID NO: 1, 2, or 4.

In some embodiments, the nucleic acid encoding a heterologous PAR enzyme comprises blPAR, ecPAR, 1ePAR, rrPAR, rsPAR, or adh6 (source listed in FIG. 4A). In some embodiments, the nucleic acid encoding a heterologous PAR enzyme comprises: (i) SEQ ID NO: 3, 5, 6, 7, 8, or 9; (ii) a nucleic acid with at least 90% identity to SEQ ID NO: 3, 5, 6, 7, 8, or 9 that encodes a PAR enzyme that is functionally homologous to the PAR enzyme encoded by SEQ ID NO: 3, 5, 6, 7, 8, or 9; or (iii) a nucleic acid that encodes a functionally homologous polypeptide with at least 90% identity to a PAR enzyme encoded by SEQ ID NO: 3, 5, 6, 7, 8, or 9.

In some embodiments, the nucleic acid encoding a heterologous PAR enzyme comprises b1PAR, ecPAR, 1ePAR, rrPAR, rsPAR, adh6, or SEQ ID NO: 3, 5, 6, 7, 8, or 9, or a functional homologue thereof sharing, for example, at least 70%, or at least 75%, or at least 80%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% nucleic acid sequence identity therewith. In some embodiments, the nucleic acid encoding a heterologous PAR enzyme encodes a functionally homologous polypeptide sharing, for example, at least 70%, or at least 75%, or at least 80%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% polypeptide sequence identity to a PAR enzyme encoded by b1PAR, ecPAR, 1ePAR, rrPAR, rsPAR, adh6, or SEQ ID NO: 3, 5, 6, 7, 8, or 9.

In some embodiments, the microorganism of the disclosure further comprises one or more of: a heterologous enzyme that converts phosphoenolpyruvate and erythrose-4-phosphate to 2-dehydro-3-deoxy-D-arabino-heptonate 7-phosphate; a heterologous enzyme that converts 3-dehydroshikimate to shikimate; or a heterologous enzyme that converts chorismate to phenylpyruvate.

In some embodiments, the heterologous enzyme that converts phosphoenolpyruvate and erythrose-4-phosphate to 2-dehydro-3-deoxy-D-arabino-heptonate 7-phosphate is 2-dehydro-3-deoxy-D-arabino-heptonate 7-phosphate synthase; the heterologous enzyme that converts 3-dehydroshikimate to shikimate is shikimate dehydrogenase; or the heterologous enzyme that converts chorismate to phenylpyruvate is bi-functional chorismate mutase/prephenate dehydratase.

In some embodiments, the nucleic acid encoding a heterologous shikimate dehydrogenase enzyme comprises cgAroE (from *Corynebacterium glutamicum*) or ecAroE (from *Escherichia coli*). In some embodiments, the nucleic acid encoding a heterologous shikimate dehydrogenase enzyme comprises: (i) SEQ ID NO: 11 or 12; (ii) a nucleic acid with at least 90% identity to SEQ ID NO: 11 or 12 that encodes a shikimate dehydrogenase enzyme that is functionally homologous to the shikimate dehydrogenase enzyme encoded by SEQ ID NO: 11 or 12; or (iii) a nucleic acid that encodes a functionally homologous polypeptide with at least 90% identity to the shikimate dehydrogenase enzyme encoded by SEQ ID NO: 11 or 12.

In some embodiments, the nucleic acid encoding a heterologous shikimate dehydrogenase enzyme comprises cgAroE, ecAroE, or SEQ ID NO: 11 or 12, or a functional homologue thereof sharing, for example, at least 70%, or at least 75%, or at least 80%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% nucleic acid sequence identity therewith. In some embodiments, the nucleic acid encoding a heterologous shikimate dehydrogenase enzyme encodes a functionally homologous polypeptide sharing, for example, at least 70%, or at least 75%, or at least 80%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% polypeptide sequence identity to a shikimate dehydrogenase enzyme encoded by cgAroE, ecAroE, or SEQ ID NO: 11 or 12.

In some embodiments, the nucleic acid encoding a heterologous DAHP synthase enzyme comprises aroG. In some embodiments, the nucleic acid encoding a heterologous DAHP synthase enzyme comprises: (i) SEQ ID NO: 10; (ii) a nucleic acid with at least 90% identity to SEQ ID NO: 10 that encodes a DAHP synthase enzyme that is functionally homologous to the DAHP synthase enzyme encoded by SEQ ID NO: 10; or (iii) a nucleic acid that encodes a functionally homologous polypeptide with at least 90% identity to the DAHP synthase enzyme encoded by SEQ ID NO: 10.

In some embodiments, the nucleic acid encoding a heterologous DAHP synthase enzyme comprises aroG or SEQ ID NO: 10, or a functional homologue thereof sharing, for example, at least 70%, or at least 75%, or at least 80%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% nucleic acid sequence identity therewith. In some embodiments, the nucleic acid encoding a heterologous DAHP synthase enzyme encodes a functionally homologous polypeptide sharing, for example, at least 70%, or at least 75%, or at least 80%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% polypeptide sequence identity to a DAHP synthase enzyme encoded by aroG or SEQ ID NO: 10.

In some embodiments, the nucleic acid encoding a heterologous bi-functional chorismate mutase/prephenate dehydratase enzyme comprises pheA1 or pheA2. In some embodiments, the nucleic acid encoding a heterologous bi-functional chorismate mutase/prephenate dehydratase enzyme comprises: (i) SEQ ID NO: 13 or 14; (ii) a nucleic acid with at least 90% identity to SEQ ID NO: 13 or 14, which encodes a bi-functional chorismate mutase/prephenate dehydratase enzyme that is functionally homologous to the bi-functional chorismate mutase/prephenate dehydratase enzyme encoded by SEQ ID NO: 13 or 14; or (iii) a nucleic acid that encodes a functionally homologous polypeptide with at least 90% identity to the bi-functional chorismate mutase/prephenate dehydratase enzyme encoded by SEQ ID NO: 13 or 14.

In some embodiments, the nucleic acid encoding a heterologous bi-functional chorismate mutase/prephenate dehydratase enzyme comprises pheA1, pheA2, or SEQ ID NO: 13 or 14, or a functional homologue thereof sharing, for example, at least 70%, or at least 75%, or at least 80%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% nucleic acid sequence identity therewith. In some embodiments, the nucleic acid encoding a heterologous bi-functional chorismate mutase/prephenate dehydratase enzyme encodes a functionally homologous polypeptide sharing, for example, at least 70%, or at least 75%, or at least 80%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% polypeptide sequence identity to a bi-functional chorismate mutase/prephenate dehydratase enzyme encoded by pheA1, pheA2, or SEQ ID NO: 13 or 14.

In some embodiments, the microorganism comprises a set of heterologous enzymes selected from among the following options:
(1) ecAroE, kivD, 1ePAR, pheA2, and aroG;
(2) ecAroE, abPPDC, ecPAR, pheA1, and aroG;
(3) cgAroE, abPPDC, 1ePAR, pheA2, and aroG;
(4) ecAroE, abPPDC, 1ePAR, pheA2, and aroG;
(5) cgAroE, kivD, rrPAR, pheA2, and aroG;
(6) ecAroE, abPPDC, 1ePAR, pheA2, and aroG;
(7) pheA1, aroG, abPPDC, and ecPAR;
(8) egAroE, abPPDC, 1ePAR, pheA1, and aroG;
(9) ecAroE, abPPDC, ecPAR, pheA2, and aroG;
(10) cgAroE, aro10, ecPAR, pheA2, and aroG;
(11) cgAroE, abPPDC, 1ePAR, pheA1, and aroG;
(12) cgAroE, aro10, 1ePAR, pheA2, and aroG;
(13) ecAroE, abPPDC, 1ePAR, pheA1, and aroG;
(14) ecAroE, aro10, ecPAR, pheA2, and aroG;
(15) ecAroE, aro10, 1ePAR, pheA2, and aroG;
(16) cgAroE, abPPDC, 1ePAR, pheA1, and aroG;
(17) cgAroE, aro10, rsPAR, pheA2, and aroG;
(18) cgAroE, abPPDC, b1PAR, pheA2, and aroG;
(19) ecAroE, kivD, b1PAR, pheA2, and aroG;
(20) cgAroE, aro10, b1PAR, pheA2, and aroG;
(21) ecAroE, abPPDC, b1PAR, pheA2, and aroG;
(22) ecAroE, abPPDC, adh6, pheA1, and aroG;
(23) cgAroE, abPPDC, adh6, pheA2, and aroG;
(24) cgAroE, abPPDC, ecPAR, pheA2, and aroG;
(25) ecAroE, aro10, rsPAR, pheA2, and aroG;
(26) ecAroE, aro10, adh6, pheA2, and aroG; or
(27) ecAroE, abPPDC, ecPAR, pheA2, and aroG.

In some embodiments, the microorganism comprises a set of heterologous nucleic acids selected from among the following options:
(1) ecAroE, kivD, 1ePAR, pheA2, and aroG;
(2) ecAroE, abPPDC, ecPAR, pheA1, and aroG;
(3) cgAroE, abPPDC, 1ePAR, pheA2, and aroG;
(4) ecAroE, abPPDC, 1ePAR, pheA2, and aroG;
(5) cgAroE, kivD, rrPAR, pheA2, and aroG;
(6) ecAroE, abPPDC, 1ePAR, pheA2, and aroG;
(7) pheA1, aroG, abPPDC, and ecPAR;
(8) egAroE, abPPDC, 1ePAR, pheA1, and aroG;
(9) ecAroE, abPPDC, ecPAR, pheA2, and aroG;
(10) cgAroE, aro10, ecPAR, pheA2, and aroG;
(11) cgAroE, abPPDC, 1ePAR, pheA1, and aroG;
(12) cgAroE, aro10, 1ePAR, pheA2, and aroG;
(13) ecAroE, abPPDC, 1ePAR, pheA1, and aroG;
(14) ecAroE, aro10, ecPAR, pheA2, and aroG;
(15) ecAroE, aro10, 1ePAR, pheA2, and aroG;
(16) cgAroE, abPPDC, 1ePAR, pheA1, and aroG;
(17) cgAroE, aro10, rsPAR, pheA2, and aroG;
(18) cgAroE, abPPDC, b1PAR, pheA2, and aroG;
(19) ecAroE, kivD, b1PAR, pheA2, and aroG;
(20) cgAroE, aro10, b1PAR, pheA2, and aroG;
(21) ecAroE, abPPDC, b1PAR, pheA2, and aroG;
(22) ecAroE, abPPDC, adh6, pheA1, and aroG;
(23) cgAroE, abPPDC, adh6, pheA2, and aroG;
(24) cgAroE, abPPDC, ecPAR, pheA2, and aroG;
(25) ecAroE, aro10, rsPAR, pheA2, and aroG;
(26) ecAroE, aro10, adh6, pheA2, and aroG; or
(27) ecAroE, abPPDC, ecPAR, pheA2, and aroG.

In some embodiments, the microorganism comprises the heterologous genes and promoters of combinatorial strain 2C03, 1C10, 2C54, 2C09, 2C47, 2C55, 2C53, H57, 1C47, 2C10, 2A18, 1054, 2C01, 1C31, 2B17, 2C52, 1C09, H18, H58, 2C27, 2D22, 2D07, 2D24, 2D03, 1C29, 2B26, 2C38, 2A27, 2C12, or 2B27, as described in Table 3.

In another embodiment, the disclosure provides plasmids that can be used to transform bacteria to produce the 2-phenylethanol-producing bacteria of the disclosure. In some embodiments, the plasmids comprise (a) a nucleic acid encoding a heterologous decarboxylase enzyme; and (b) a nucleic acid encoding a heterologous phenylacetaldehyde reductase (PAR) enzyme. In some embodiments the plasmids comprise (a) a nucleic acid encoding a heterologous decarboxylase enzyme; (b) a nucleic acid encoding a heterologous phenylacetaldehyde reductase (PAR) enzyme; (c) a nucleic acid encoding a heterologous shikimate dehydrogenase enzyme; (d) a nucleic acid encoding a heterologous DAHP synthase enzyme; and (e) a nucleic acid encoding a heterologous bi-functional chorismate mutase/prephenate dehydratase enzyme. In some embodiments, the disclosure provides a two-plasmid system, the first plasmid comprising (a) a nucleic acid encoding a heterologous decarboxylase enzyme; (b) a nucleic acid encoding a heterologous phenylacetaldehyde reductase (PAR) enzyme; and (c) a nucleic acid encoding a heterologous shikimate dehydrogenase enzyme; and a second plasmid comprising (d) a nucleic acid encoding a heterologous DAHP synthase enzyme; and (e) a nucleic acid encoding a heterologous bi-functional chorismate mutase/prephenate dehydratase enzyme. When the plasmid or plasmids are transformed into the bacteria, desirably the bacteria express the enzymes. Alternatively, the enzymes can be expressed only when induced, if an inducible promoter is used for expression.

One embodiment is a microorganism capable of producing 2-phenylethanol, wherein the microorganism comprises: (a) a heterologous enzyme that converts phenylpyruvate to phenylacetaldehyde; and (b) a heterologous enzyme that converts phenylacetaldehyde to 2-phenylethanol.

The microorganism of an embodiment, wherein: (a) the heterologous enzyme that converts phenylpyruvate to phenylacetaldehyde is decarboxylase; and (b) the heterologous enzyme that converts phenylacetaldehyde to 2-phenylethanol is phenylacetaldehyde reductase.

The microorganism of an embodiment, wherein the decarboxylase is a phenylpyruvate-specific decarboxylase.

The microorganism of an embodiment, wherein the microorganism is a C1-fixing microorganism.

The microorganism of an embodiment, wherein the microorganism is a Wood-Ljungdahl microorganism.

The microorganism of an embodiment, wherein the microorganism is a bacterium.

The microorganism of an embodiment, wherein the microorganism is a member of a genus selected from the group consisting of *Acetobacterium, Alkalibaculum, Blautia, Butyribacterium, Clostridium, Eubacterium, Moorella, Oxobacter, Sporomusa,* and *Thermoanaerobacter*.

The microorganism of an embodiment, wherein the microorganism is natively capable of producing phenylpyruvate.

The microorganism of an embodiment, wherein the microorganism comprises a Wood-Ljungdahl pathway that converts CO, $CO_2$, and/or $H_2$ to acetyl-CoA.

The microorganism of an embodiment, wherein the microorganism comprises one or more of: (c) a native enzyme that converts acetyl-CoA to pyruvate; (d) a native enzyme that converts pyruvate to phosphoenolpyruvate; (e) a native enzyme that converts phosphoenolpyruvate and erythrose-4-phosphate to 2-dehydro-3-deoxy-D-arabino-heptonate 7-phosphate; (f) a native enzyme that converts 2-dehydro-3-deoxy-D-arabino-heptonate 7-phosphate to 3-dehydroquinate; (g) a native enzyme that converts 3-dehydroquinate to 3-dehydroshikimate; (h) a native enzyme that converts 3-dehydroshikimate to shikimate; (i) a native enzyme that converts shikimate to shikimate 3-phosphate; (j) a native enzyme that converts shikimate 3-phosphate to 5-O-(1-carboxyvinyl)-shikimate 3-phosphate; (k) a native enzyme that converts 5-O-(1-carboxyvinyl)-shikimate 3-phosphate to chorismate; or (1) a native enzyme that converts chorismate to phenylpyruvate.

The microorganism of an embodiment, wherein: (c) the native enzyme that converts acetyl-CoA to pyruvate is pyruvate:ferredoxin oxidoreductase; (d) the native enzyme that converts pyruvate to phosphoenolpyruvate is pyruvate phosphate dikinase; (e) the native enzyme that converts phosphoenolpyruvate and erythrose-4-phosphate to 2-dehydro-3-deoxy-D-arabino-heptonate 7-phosphate is 2-dehydro-3-deoxy-D-arabino-heptonate 7-phosphate synthase; (f) the native enzyme that converts 2-dehydro-3-deoxy-D-arabino-heptonate 7-phosphate to 3-dehydroquinate is 3-dehydroquinate synthase; (g) the native enzyme that converts 3-dehydroquinate to 3-dehydroshikimate is 3-dehydroquinate dehydratase; (h) the native enzyme that converts 3-dehydroshikimate to shikimate is shikimate dehydrogenase; (i) the native enzyme that converts shikimate to shikimate 3-phosphate is shikimate kinase; (j) the native enzyme that converts shikimate 3-phosphate to 5-O-(1-carboxyvinyl)-shikimate 3-phosphate is 5-enolpyruvylshikimate 3-phosphate synthase; (k) the native enzyme that converts 5-O-(1-carboxyvinyl)-shikimate 3-phosphate to chorismate is chorismate synthase; or (1) the native enzyme that converts chorismate to phenylpyruvate is bi-functional chorismate mutase/prephenate dehydratase.

The microorganism of an embodiment, wherein the microorganism further comprises one or more of: (e) a heterologous enzyme that converts phosphoenolpyruvate and erythrose-4-phosphate to 2-dehydro-3-deoxy-D-arabino-heptonate 7-phosphate; (h) a heterologous enzyme that converts 3-dehydroshikimate to shikimate; or (1) a heterologous enzyme that converts chorismate to phenylpyruvate.

The microorganism of an embodiment, wherein: (e) the heterologous enzyme that converts phosphoenolpyruvate and erythrose-4-phosphate to 2-dehydro-3-deoxy-D-arabino-heptonate 7-phosphate is 2-dehydro-3-deoxy-D-arabino-heptonate 7-phosphate synthase; (h) the heterologous enzyme that converts 3-dehydroshikimate to shikimate is shikimate dehydrogenase; or (1) the heterologous enzyme that converts chorismate to phenylpyruvate is bi-functional chorismate mutase/prephenate dehydratase.

The microorganism of any one of the embodiments, wherein the microorganism comprises:
(1) ecAroE, kivD, 1ePAR, pheA2, and aroG;
(2) ecAroE, abPPDC, ecPAR, pheA1, and aroG;
(3) cgAroE, abPPDC, 1ePAR, pheA2, and aroG;
(4) ecAroE, abPPDC, 1ePAR, pheA2, and aroG;
(5) cgAroE, kivD, rrPAR, pheA2, and aroG;
(6) ecAroE, abPPDC, 1ePAR, pheA2, and aroG;
(7) pheA1, aroG, abPPDC, and ecPAR;
(8) egAroE, abPPDC, 1ePAR, pheA1, and aroG;
(9) ecAroE, abPPDC, ecPAR, pheA2, and aroG;
(10) cgAroE, aro10, ecPAR, pheA2, and aroG;
(11) cgAroE, abPPDC, 1ePAR, pheA1, and aroG;
(12) cgAroE, aro10, 1ePAR, pheA2, and aroG;
(13) ecAroE, abPPDC, 1ePAR, pheA1, and aroG;
(14) ecAroE, aro10, ecPAR, pheA2, and aroG;
(15) ecAroE, aro10, 1ePAR, pheA2, and aroG;
(16) cgAroE, abPPDC, 1ePAR, pheA1, and aroG;
(17) cgAroE, aro10, rsPAR, pheA2, and aroG;
(18) cgAroE, abPPDC, b1PAR, pheA2, and aroG;
(19) ecAroE, kivD, b1PAR, pheA2, and aroG;
(20) cgAroE, aro10, b1PAR, pheA2, and aroG;
(21) ecAroE, abPPDC, b1PAR, pheA2, and aroG;
(22) ecAroE, abPPDC, adh6, pheA1, and aroG;
(23) cgAroE, abPPDC, adh6, pheA2, and aroG;
(24) cgAroE, abPPDC, ecPAR, pheA2, and aroG;
(25) ecAroE, aro10, rsPAR, pheA2, and aroG;
(26) ecAroE, aro10, adh6, pheA2, and aroG; or
(27) ecAroE, abPPDC, ecPAR, pheA2, and aroG.

The microorganism of any one of the embodiments, wherein the microorganism comprises the heterologous genes and promoters of combinatorial strain 2C03, 1C10, 2C54, 2C09, 2C47, 2C55, 2C53, H57, 1C47, 2C10, 2A18, 1O54, 2C01, 1C31, 2B17, 2C52, 1C09, H18, H58, 2C27, 2D22, 2D07, 2D24, 2D03, 1C29, 2B26, 2C38, 2A27, 2C12, or 2B27.

The microorganism of any one of the embodiments, wherein the microorganism ferments a gaseous substrate comprising CO, $CO_2$, and/or $H_2$ to produce 2-phenylethanol.

The microorganism of an embodiment, wherein the gaseous substrate comprises syngas or industrial waste gas.

The microorganism of an embodiment, wherein the microorganism does not produce any other C3+ alcohols.

The microorganism of an embodiment, wherein the microorganism does not produce any other C3, C4, C5, C6, C7, C8, C9, or C10 alcohols.

One embodiment is a method of producing 2-phenylethanol comprising culturing the microorganism of any one of the embodiments in the presence of a gaseous substrate.

The method of an embodiment, wherein the gaseous substrate comprises a C1-carbon source comprising CO, $CO_2$, and/or $H_2$.

The method of any one of the embodiments, wherein the gaseous substrate comprises syngas or industrial waste gas.

EXAMPLES

The following examples further illustrate the methods and compositions of the disclosure but should not be construed to limit its scope in any way.

Figure 1:

In this work, targeted metabolic engineering of the decarboxylase and phenylacetaldehyde reductase (PAR) was carried out in C1-fixing bacteria to improve 2-PE selectivity and production. To further improve the flux towards 2-PE biosynthesis, three heterologous genes from the shikimate pathway were additionally included in a combinatorial manner. The 2-PE biosynthesis pathway and the genes that were heterologously expressed in the following Examples are highlighted in FIG. 1.

Example 1. 2-PE Tolerance of *C. autoethanogenum* in Schott Bottles

2-PE has been reported to exert a growth inhibitory effect on Gram-positive microorganisms such as *Staphylococcus*

Figure 2A:
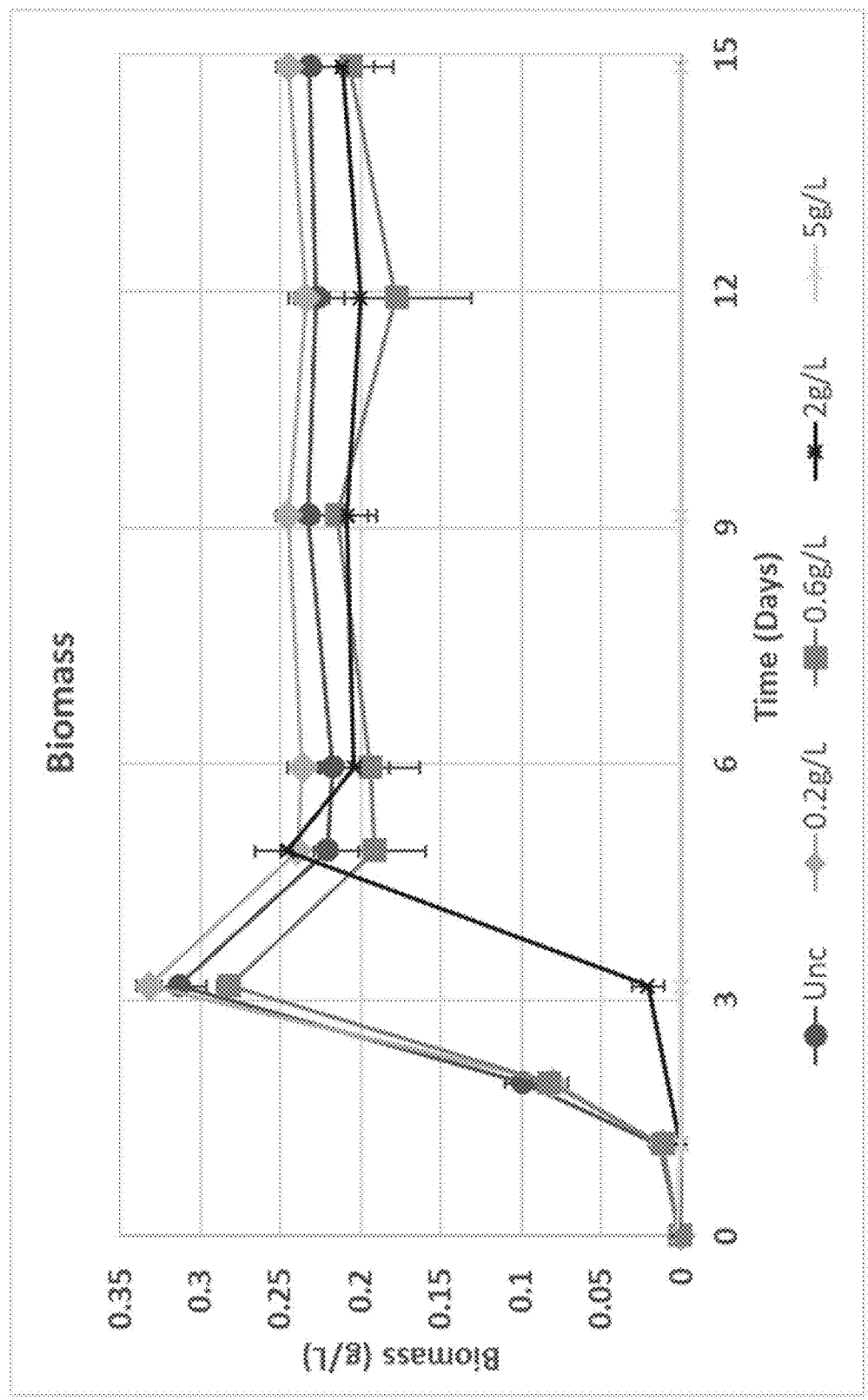
Figure 2B:
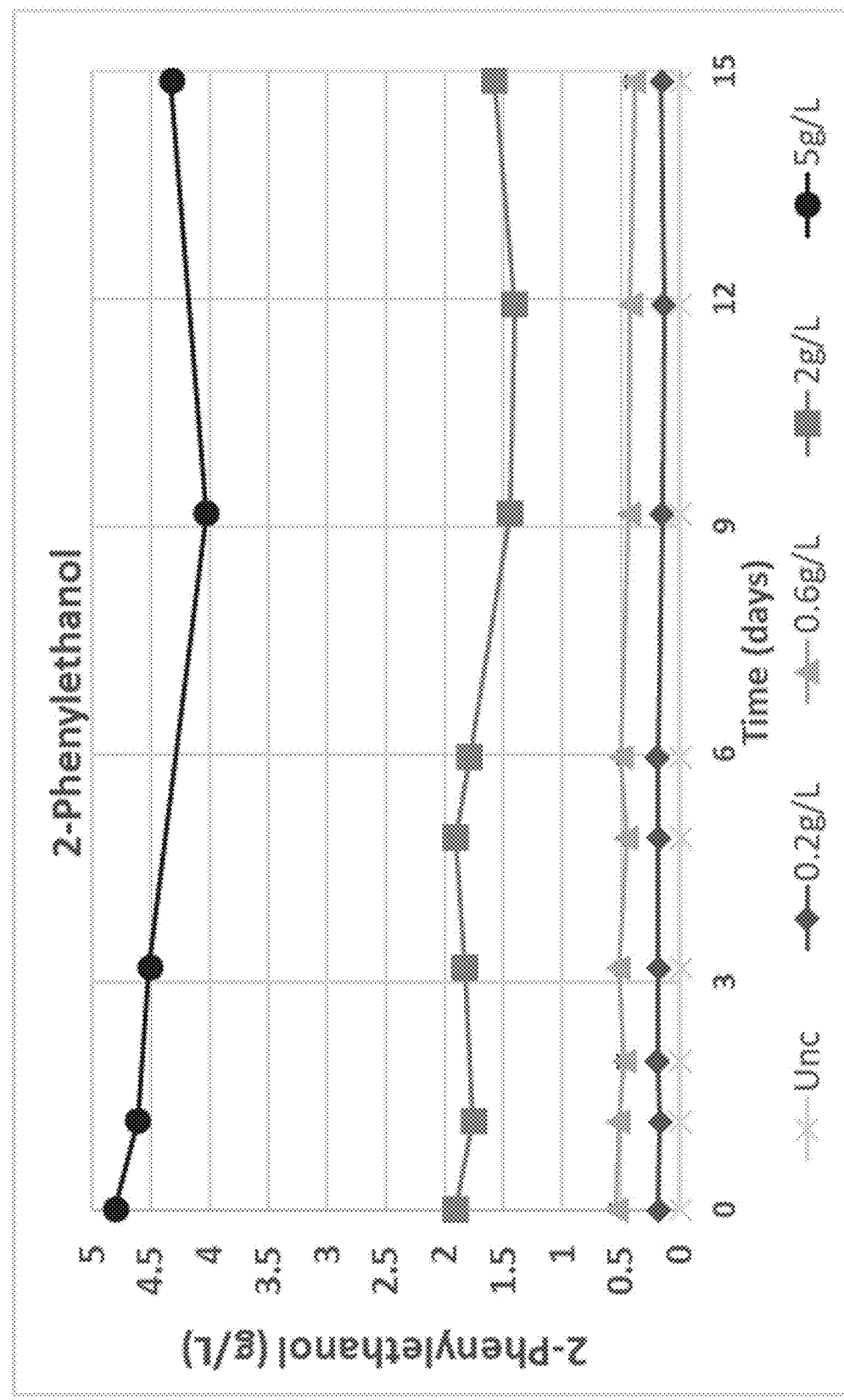

*aureus* and *Enterococcus faecium* at 26-43 mM (3.2-5.3 g/L) levels (Cone et al., Res Microbiol. 1990; 141(4):483-97). To study the toxicity of 2-PE on autotrophic growth of *C. autoethanogenum*, a 2-PE challenge experiment (at 0, 0.2, 0.6, 2 and 5 g/L) was conducted in Schott bottles with synthetic gas blend (50% CO, 10% $H_2$, 30% $CO_2$ and 10% $N_2$). In comparison to the unchallenged culture, 2 g/L of 2-PE resulted in an increase in growth lag phase and lower biomass concentrations (FIGS. 2A-B). At 5 g/L challenge level, no growth was detected (FIGS. 2A-B). 2-PE challenge at 0.2 g/L and 0.6 g/L had little impact on autotrophic growth of *C. autoethanogenum*.

Figure 3A:
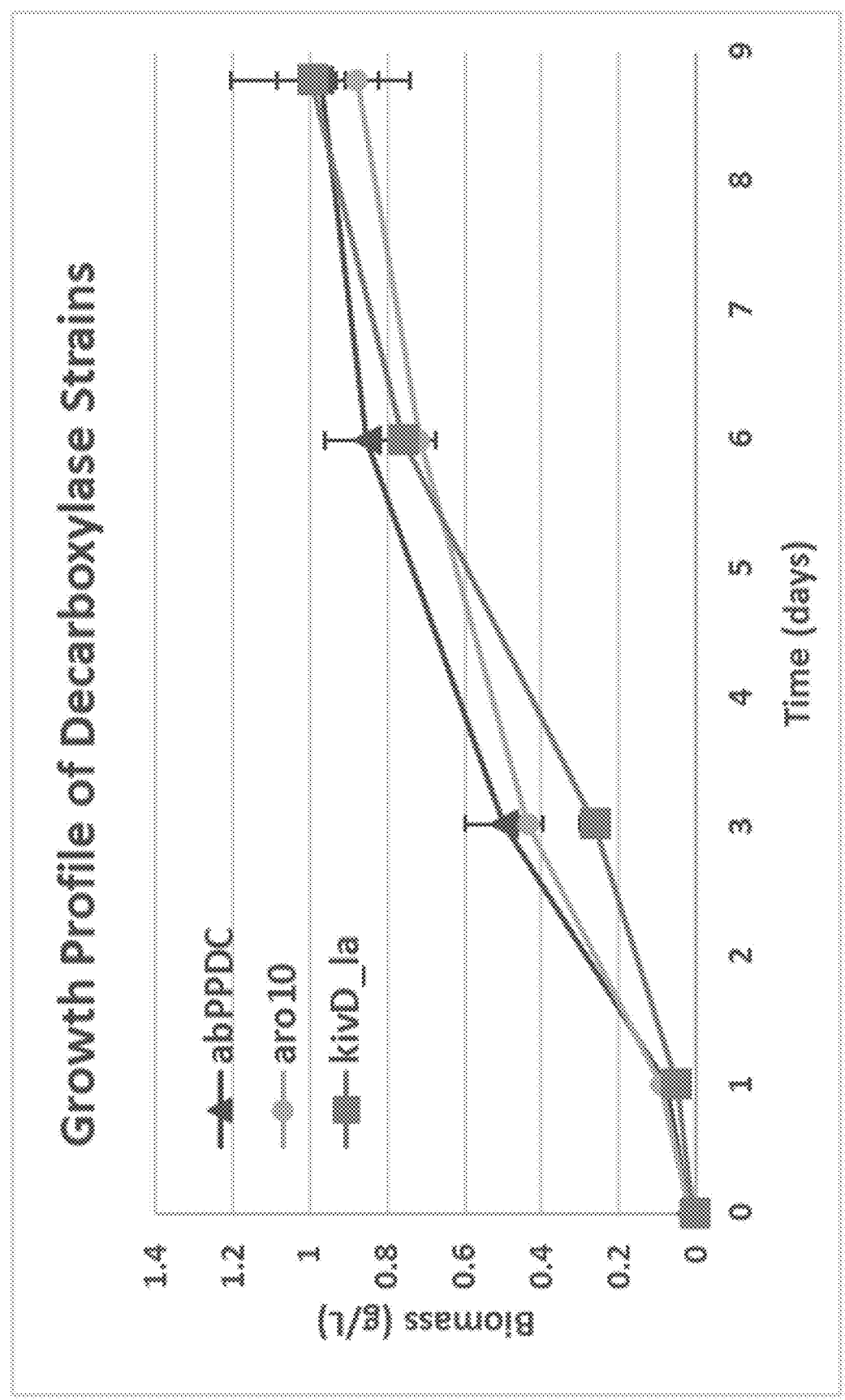
Figure 3B:
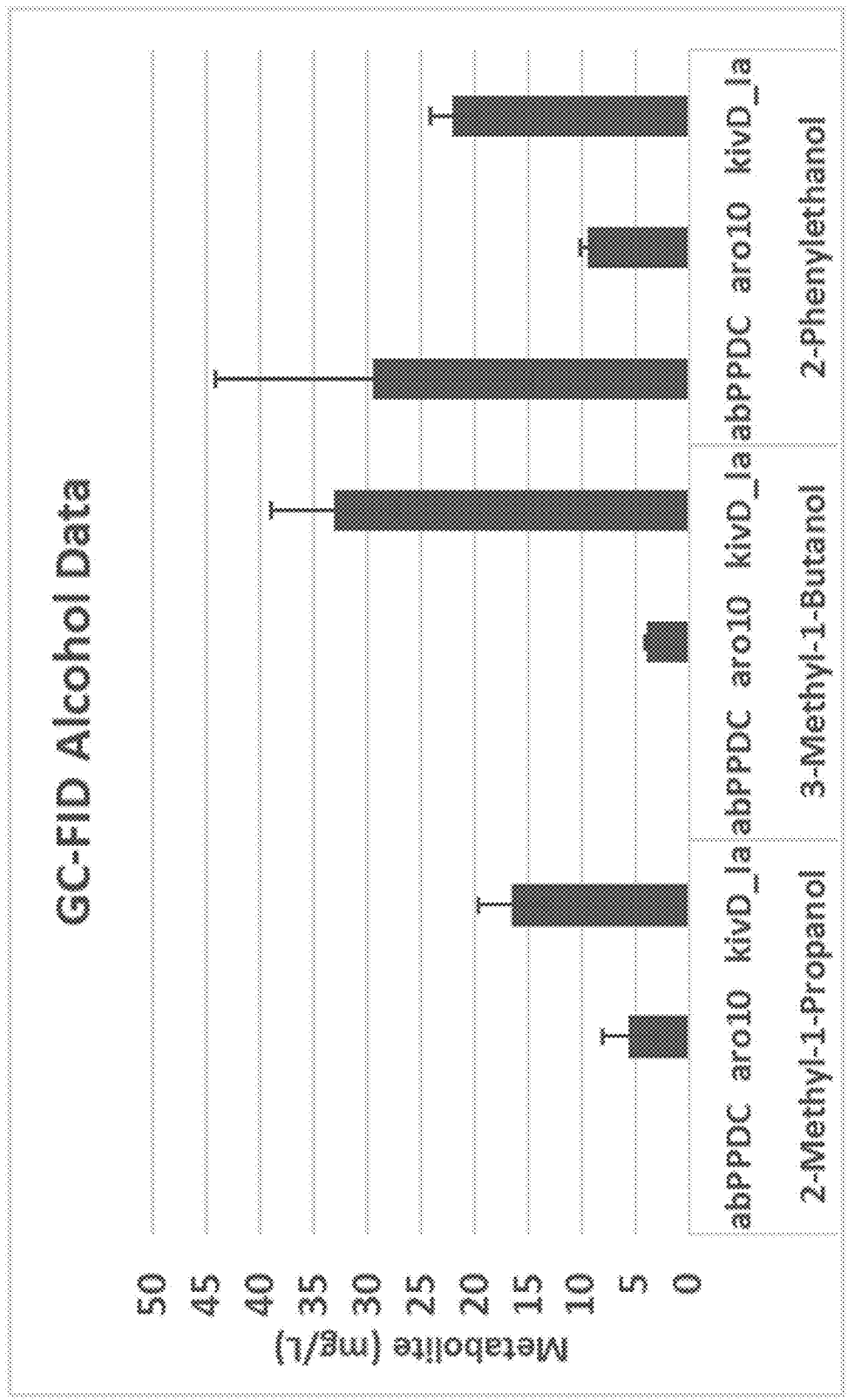

Example 2. Testing of Decarboxylase Variants for Improved 2-PE Selectivity and Production For 2-PE strain optimization, two plasmids with phenylpyruvate-specific decarboxylases (aro10 from *Saccharomyces cerevisiae* (Kneen et al., FEBS J. 2011; 278:1842-53) (SEQ ID NO: 4) and abPPDC from *Azospirillum brasilense* (Spaepen et al., J Bacteriol. 2007; 189:7626 LP-7633) (SEQ ID NO: 2)) were transformed into *C. autoethanogenum*, resulting in strains sFA212 and sFA213, respectively. These two decarboxylase strains, together with a control strain (sFA200) that expresses decarboxylase kivd_la (from *Lactococcus lactis*) (SEQ ID NO: 1), were subjected to autotrophic growth under synthetic gas mix (50% CO, 10% $H_2$, 30% $CO_2$, and 10% $N_2$) in Schott bottles (FIGS. 3 A-B). The three decarboxylase strains displayed similar growth profiles but different alcohol profiles (FIGS. 3 A-B). End-point gas chromatography with flame ionization detection (GC-FID) results showed that the aro10 strain produced 57% less 2-PE than the control kivd_la strain, while producing 5.6 mg/L 2-methyl-1-propanol and 4.0 mg/L 3-methyl-1-butanol. In contrast, the abPPDC strain produced similar amounts of 2-PE as the control strain, but none of the branch-chain alcohols. In some embodiments, the increased selectivity towards 2-PE by the abPPDC strain could simplify downstream product separation and improve strain stability as branch-chain alcohols could exert an additive effect on cell toxicity.

For this and the other examples disclosed herein, GC-FID was performed for linear and branched-chain alcohols as follows. Alcohol concentrations were measured by gas chromatography analysis using an Agilent 7890B GC equipped with an autosampler, flame ionization detection (FID) and a Phenomenex ZB-WAXplus column (30 m×0.32 mm×1 µm) linked in series to a ZB-1 column (30 m×0.32 mm×0.3 µm). Samples were prepared by transferring 1.400 mL of sample to a clean 2-mL microcentrifuge tube followed by the addition of 20 µL of an internal standard solution (phenyl acetate in ethanol). To this, 400 µL of chloroform was added and the mass recorded. Samples were shaken horizontally for 60 seconds, centrifuged at 14,000×g for 5 minutes, then 200 µL of the bottom layer was transferred to a glass vial containing a low-volume insert. Analysis of a 1-µL injection was performed using a split ratio of 10 to 1 and an inlet temperature of 250° C. Separation was achieved with a starting oven temperature of 70° C. (no hold), an initial ramp to 120° C. at 3° C./min (no hold), and a final ramp to 230° C. at 7° C./min (14 minute hold). Column flow rate was set to 35 cm/sec with helium as the carrier gas. The FID was set to 280° C. with air at 400 mL/min, hydrogen gas at 40 mL/min, and helium (makeup gas) at 15 mL/min. Results were calculated using an internal standard calibration using a linear fit.

Figure 4B:
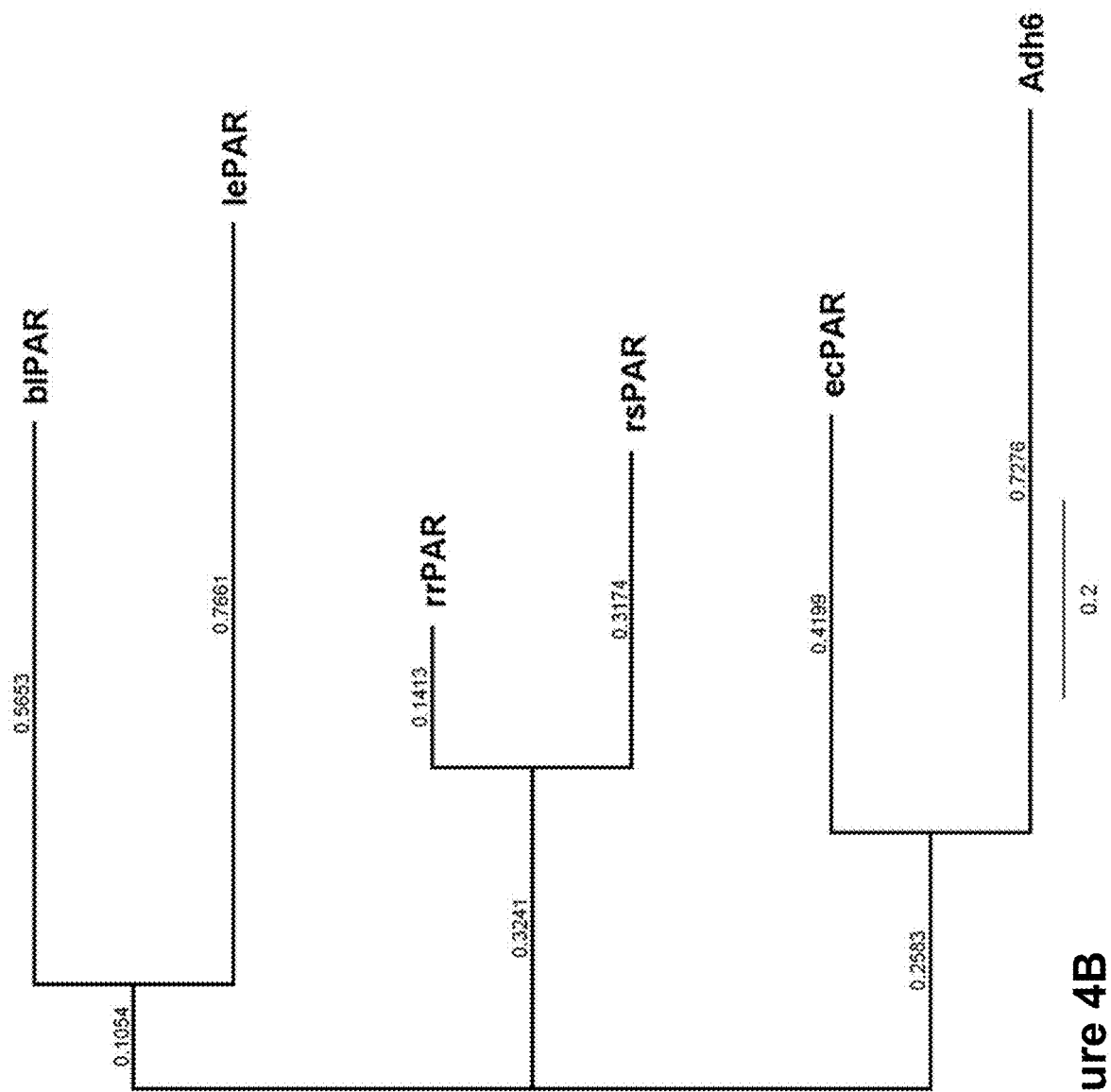
Figure 4C:
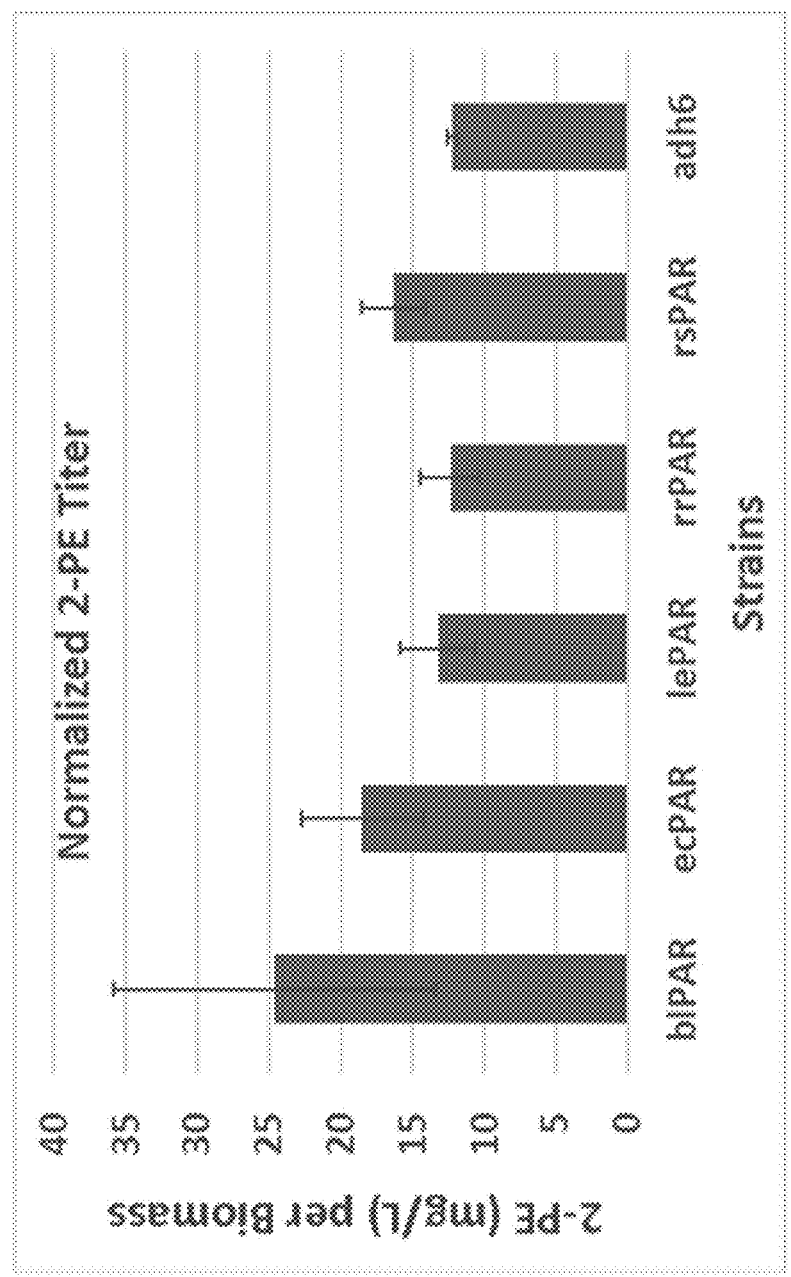

Example 3. Testing of Phenylacetaldehyde Reductase (PAR) Variants for Improved 2-PE Production Five gene variants (1ePAR (SEQ ID NO: 9), ecPAR (SEQ ID NO: 6), b/PAR (SEQ ID NO: 5), rrPAR (SEQ ID NO: 7), and rsPAR (SEQ ID NO: 8); FIGS. 4A-B) of phenylacetaldehyde reductase (PAR), which catalyzes the last step of the 2-PE pathway (FIG. 1), were individually cloned into expression vectors with decarboxylase abPPDC (SEQ ID NO: 2) and shikimate dehydrogenase ecAroE (SEQ ID NO: 11). Following transformation into *C. autoethanogenum*, the resulting recombinant strains were tested for 2-PE production in 12-well plates with 200 kPa synthetic gas mix (50% CO, 10% $H_2$, 30% $CO_2$, and 10% $N_2$). Inducer was added on day 1, and samples were collected for GC-FID analysis on day 7. Three of the new PAR strains (b/PAR, ecPAR, and rsPAR) produced more 2-PE (normalized by biomass) than the adh6 (SEQ ID NO: 3) control strain (FIG. 4C).

Example 4. Combinatorial Analysis of 2-PE Pathway

Figure 5:
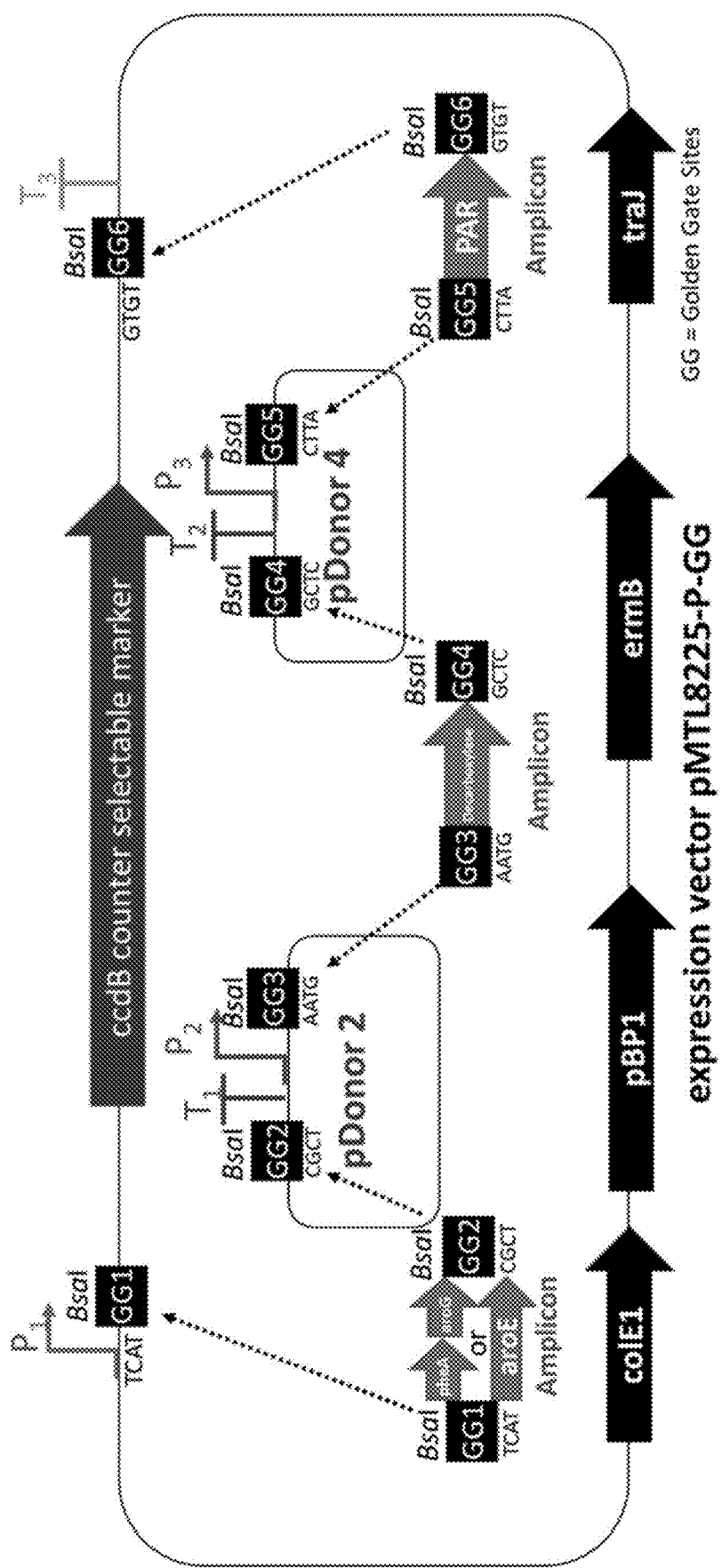
FIG. 5 shows combinatorial assembly of 2-PE pathway genes using the Golden Gate method.
Figure 6:
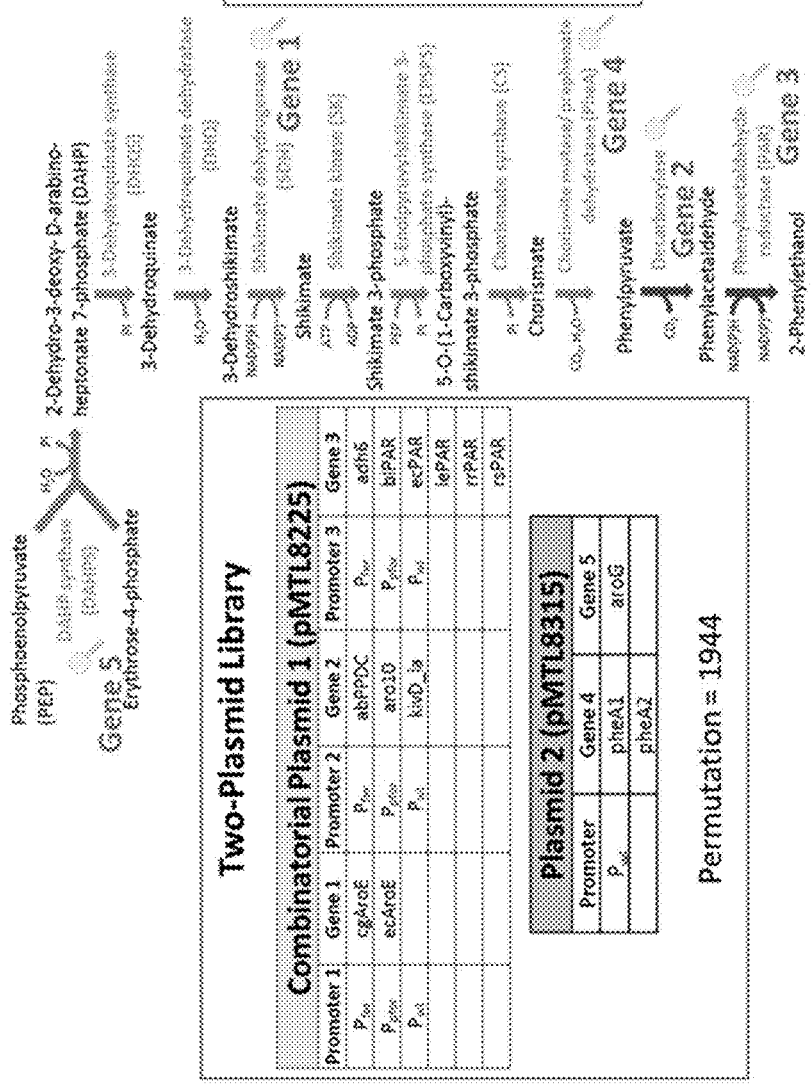
FIG. 6 shows gene and promoter variants that were employed for the two 2-PE combinatorial libraries described in Example 4.

In order to determine the optimum flux and gene variants for the biosynthesis of 2-PE, a combinatorial assembly of the 2-PE pathway genes and promoters using the Golden Gate (GG) method was first performed in *Escherichia coli* (FIG. 5) before transformation into C1-utilizing microorganisms. To facilitate the screening of assembly, a ccdB toxin-antitoxin counter-selectable marker flanked by Golden Gate site GG1 and GG6 was first cloned into Clostridium-E. coli shuttle vector pMTL8225 (Heap, J Microbiol Methods, 78: 79-85, 2009). These shuttle vectors have a pre-cloned clostridial promoter (shown as $P_1$ in FIG. 5) and terminator (shown as T3 in FIG. 5). The genes that encode shikimate dehydrogenase (encoded by aroE), DAHP synthase (encoded by aroG), bi-functional chorismate mutase/prephenate dehydratase (pheA), decarboxylase, and phenyl-acetaldehyde (PAR), together with two donor vectors (pDonor 2 and pDonor 4, which provide the terminators and promoters), were added to the shuttle vectors for GG assembly. The promoter sequences. Golden Gate sites, and assembly workflow are described in Synthetic Biology (2020) vol 5(1): ysaa019. The resulting combinatorial plasmids with ermB antibiotic selectable marker (collectively called plasmid 1 in Table 3) have a promoter and terminator to express each of aroE (or pheA+aroG), decarboxylase and PAR in an insulated manner.

For this work, two 2-PE combinatorial libraries were constructed and tested: one-plasmid and two-plasmid libraries (Table 3). The gene variants (2× aroE (SEQ ID NOs: 11, 12), 3× decarboxylase (SEQ ID NOs: 1, 2, 4), 6×PAR (SEQ ID NOs: 3, 5, 6, 7, 8, 9), 2× bi-functional chorismate mutase/prephenate dehydratase (pheA) (SEQ ID NOs: 13, 14), and 1×DAHP synthase (aroG) (SEQ ID NO: 10)) that were included in the combinatorial analysis are shown in Table 2. (FIG. 12) shows gene and promoter variants that were employed for the two 2-PE combinatorial libraries described in Example 4.

TABLE 2

2-PE pathway gene variants employed for combinatorial analysis.

| Enzyme | Gene [SEQ ID NO] | Description | Reference |
|---|---|---|---|
| DAHP synthase (EC 2.5.1.54) | aroG [10] | E. coli; L175D to alleviate phenylalanine feedback regulation | Hu et al., J Basic Microbiol. 2003;43(5):399-406. |
| Shikimate dehydrogenase (EC 1.1.1.25) | cgAroE [12] | Corynebacterium glutamicum | Kubota et al., Appl Microbiol Biotechnol. 2013;97:8139-49. |
| | ecAroE [11] | E. coli | Sun et al., Appl Environ Microbiol. 2013; 79(13):4024-30. |
| Chorismate mutase/prephenate dehydratase (EC 4.2.1.51) | pheA1 [13] | E. coli; Deletion of 49 residues at 3' end to alleviate phenylalanine feedback regulation | U.S. Pat. No. 4,753,883 |
| | pheA2 [14] | E. coli; W338R to alleviate phenylalanine feedback regulation | U.S. Pat. No. 4,753,883 |
| Decarboxylase (EC 4.1.1.74) | abPPDC [2] | Azospirillum brasilense | Spaepen et al., J Bacteriol. 2007;189:7626 LP-7633. |
| | aro10 [4] | Saccharomyces cerevisiae | Kneen et al., FEBS J. 2011;278:1842-53. |
| | kivD_la [1] | Lactococcus lactis | De La Plaza et al., FEMS Microbiol Lett. 2004; 238(2):367-74. |
| Phenylacetaldehyde reductase (EC 1.1.1.1) | blPAR [5] | Brevibacterium linens | Hirano et al., Appl Microbiol Biotechnol. 2007;76(2):357-63. |
| | ecPAR [6] | E. coli | Guo et al., Microbiologyopen. 2017 Aug;6(4). |
| | lePAR [9] | Solanum lycopersicum (tomato) | Tieman et al., Phytochemistry. 2007;68(21):2660-9. |
| | rrPAR [7] | Rhodococcus ruber | Giersberg et al., J Ind Microbiol Biotechnol. 2012 Sep;39(9):1385-96. |
| | rsPAR [8] | Rhodococcus sp. ST-10 | Itoh et al., Appl Environ Microbiol. 1997 Oct;63(10):3783-8. |
| | adh6 [3] | S. cerevisiae | Larroy et al., Chem Biol Interact. 2003 Feb 1;143-144:229-38. |

In the case of the two-plasmid library, three promoters of different strengths ($P_{fer-lacO-US}$, $P_{WL}$ and $P_{pfor}$) were used to express each of aroE, decarboxylase, and PAR in plasmid 1. Plasmid 2 (catP antibiotic selectable marker), which had only one promoter ($P_{WL}$) that drove the expression of pheA1+aroG or pheA2+aroG, was individually transformed into C. autoethanogenum. The resulting transformants subsequently became the host into which the combinatorial plasmid 1 was transferred, resulting in recombinant strains that carried two expression vectors conferring different antibiotic resistance with compatible Gram-positive replicons. The total permutation for the two-plasmid combinatorial library was 1944 (3×2×3×3×3×6×1×2×1).

In the case of the one-plasmid library, the aroE in plasmid 1 was replaced by (pheA1/pheA2)+aroG. This resulted in only 1 plasmid (with aroE omitted) and a permutation of 972 (3×2×3×3×3×6). During this process, the spacer distance between the ribosomal binding site and START codon of aroG was extended from 5 to 8 nucleotides to enhance the translation of aroG.

To determine the assembly efficiency of combinatorial plasmids in E. coli, and to investigate the promoter and gene variant combinations, 400 plasmids were extracted from transformed E. coli strain NEB10-beta and subjected to sequencing. Analysis of the sequencing results showed an assembly rate of 51.3%, with good diversity of each promoter and gene variants. Following transformation of these sequence-verified combinatorial plasmids into C. autoethanogenum, a total of 162 combinatorial strains (42 one-plasmid strains and 120 two-plasmid strains) were subjected to autotrophic growth in 12-well plates.

Growth experiments were conducted with technical duplicates in 12-well plates with 2 mL minimal media and 200 kPa of synthetic gas mix (50% CO, 10% $H_2$, 30% $CO_2$, and 10% $N_2$) at 37° C. for 8-10 days (FIGS. 7A-C). Broth samples were then taken for biomass measurement and GC-FID analysis to determine 2-PE titer. Three biological clones of strain sFA212, which harbors a plasmid (of the same backbone as plasmid 1) that expresses adh6 with abPPDC under the inducible promoter $P_{ipl12}$, were chosen as a control strain because this strain consistently produced high amounts of 2-PE in 12-well plates, Schott bottles, and continuously stirred tank reactors (CSTRs). One media blank control well per 12-well plate was included as negative control and GC-FID analysis showed <1.7 mg/L 2-PE, which indicates little-to-no cross-well contamination.

Following 8-10 days of incubation, the 2-PE combinatorial strains reached biomass concentration of 0.6-1.0 gDCW/L (FIG. 7C). Out of these 162 combinatorial strains, 80 strains (49% of the screened library) produced >1.5-fold more 2-PE than the control strain (FIG. 7A). 48 strains (30% of the screened library) produced less than half of the 2-PE produced by the control strain (FIG. 7A).

Detailed analysis of the 2-PE combinatorial library was conducted to discern the effects of gene variants and number of plasmids on 2-PE production (FIGS. 8A-E). No significant difference in 2-PE titer was observed between the one-plasmid and two-plasmid libraries, decarboxylases, and shikimate dehydrogenases (FIGS. 8A, 8C, and 8D). Strains with pheA2 showed slightly higher 2-PE titers than strains with pheA1 (FIG. 8B). Some of the PAR variants (e.g., blPAR) produced more 2-PE than the adh6 variant (FIG. 8E). The large 2-PE titer variations observed in each gene variant or plasmid number could be attributed to the collective effect of other pathway gene variants and promoter combinations, which diluted the effect of single parameters in the combinatorial design.

By ranking the 2-PE titer relative to the control strain sFA212, a list of top 30 2-PE producing combinatorial strains with their genotype was produced (Table 3). Although 74% of the screened combinatorial library were two-plasmid strains with either aroE, 90% of the top 30 2-PE producing strains carried two plasmids. All top 10 2-PE producing strains consisted of either decarboxylase variant kivD_la or abPPDC, whereas strains with decarboxylase aro10 appeared 8 times between the top 11 and top 30 2-PE producers. Strains with PAR variant 1ePAR and ecPAR accounted for 70% of the top 30 2-PE producers, disproportionately high relative to their overall representation of 57% in the screened library. Strains with PAR variant adh6 were significantly under-represented in the top 30 2-PE producers: only 6.7% in the top 30 vs. 13.6% in the screened library overall.

Example 5. 2-PE Production from Syngas Fermentation in CSTRs

A total of 12 combinatorial strains were characterized in CSTR under continuous fermentation mode to compare their 2-PE production to reference strain sFA212. Actively growing (early exponential) culture from Schott bottles was used as inoculum for 2-L CSTRs with a synthetic gas blend (40% CO, 20% $H_2$, 20% $CO_2$, and 20% $N_2$) at atmospheric pressure. Once the biomass concentration reached ~0.5 gDCW/L, a media dilution rate of 1/day and a bacterial dilution rate of ~0.5/day were maintained.

Under these continuous CSTR conditions, the reference strain sFA212 achieved a 2-PE titer of 70 mg/L. Five combinatorial strains (1C29, 2C54, 2C03, 2C53 and 2C31) produced more 2-PE than the reference strain (FIG. 9A). In particular, strain 1C29 produced 200 mg/L of 2-PE, 2.9-fold higher than the reference strain. Based on their 2-PE yield, 10 of the 12 combinatorial strains displayed superior 2-PE performance relative to the reference strain (FIG. 9B).

The performance of combinatorial strain 1C29 in two replicate CSTR runs is shown in FIGS. 10A-B. To enhance 2-PE production, nitrogen supply in the form of $NH_4OH$ was limited to 15 mM on day 7 for replicate 1 (FIG. 10A), and day 9 for replicate 2 (FIG. 10B). As a result, 2-PE production increased in both runs and peaked at 350 and 300 mg/L, respectively. The 2-PE productivity momentarily peaked at 16 mg/L/h for run 1.

TABLE 3

Genotype of top 30 2-PE producing combinatorial strains in the 12-well plate growth assay.

| Strain Name | Average 2PE titer relative to sFA212 | Plasmid 1 | | | | | | Plasmid 2 | | |
|---|---|---|---|---|---|---|---|---|---|---|
| | | P1 | Gene 1 | P2 | Gene 2 | P3 | Gene 3 | P4 | Gene 4 | Gene 5 |
| 2C03 | 3.01 | Ppfor | ecAroE | Pwl | kivD | Pwl | lePAR | Pwl | pheA2 | aroG |
| 1C10 | 2.99 | Ppfor | ecAroE | Pwl | abPPDC | Pfer | ecPAR | Pwl | pheA1 | aroG |
| 2C54 | 2.94 | Ppfor | cgAroE | Ppfor | abPPDC | Pwl | lePAR | Pwl | pheA2 | aroG |
| 2C09 | 2.92 | Ppfor | cgAroE | Ppfor | abPPDC | Pfer | lePAR | Pwl | pheA2 | aroG |
| 2C47 | 2.91 | Ppfor | ecAroE | Ppfor | abPPDC | Pwl | lePAR | Pwl | pheA2 | aroG |
| 2C55 | 2.85 | Ppfor | cgAroE | Pwl | kivD | Pwl | rrPAR | Pwl | pheA2 | aroG |
| 2C53 | 2.75 | Ppfor | ecAroE | Ppfor | abPPDC | Pwl | lePAR | Pwl | pheA2 | aroG |
| H57 | 2.72 | Pwl | pheA1 + aroG | Ppfor | abPPDC | Pfer | ecPAR | | None | |
| 1C47 | 2.71 | Ppfor | ecAroE | Ppfor | abPPDC | Pwl | lePAR | Pwl | pheA1 | aroG |
| 2C10 | 2.70 | Ppfor | ecAroE | Pwl | abPPDC | Pfer | ecPAR | Pwl | pheA2 | aroG |
| 2A18 | 2.69 | Pfer | cgAroE | Pwl | aro10 | Ppfor | ecPAR | Pwl | pheA2 | aroG |
| 1C54 | 2.66 | Ppfor | cgAroE | Ppfor | abPPDC | Pwl | lePAR | Pwl | pheA1 | aroG |
| 2C01 | 2.63 | Ppfor | cgAroE | Pfer | aro10 | Pfer | lePAR | Pwl | pheA2 | aroG |
| 1C31 | 2.62 | Ppfor | ecAroE | Pfer | abPPDC | Pwl | lePAR | Pwl | pheA1 | aroG |
| 2B17 | 2.54 | Pwl | ecAroE | Ppfor | aro10 | Ppfor | ecPAR | Pwl | pheA2 | aroG |
| 2C52 | 2.52 | Ppfor | ecAroE | Pfer | aro10 | Ppfor | lePAR | Pwl | pheA2 | aroG |
| 1C09 | 2.48 | Ppfor | cgAroE | Ppfor | abPPDC | Pfer | lePAR | Pwl | pheA1 | aroG |
| H18 | 2.48 | Pwl | pheA1 + aroG | Pfer | abPPDC | Ppfor | ecPAR | | None | |
| H58 | 2.43 | Ppfor | pheA1 + aroG | Ppfor | abPPDC | Pwl | ecPAR | | None | |
| 2C27 | 2.39 | Ppfor | cgAroE | Pwl | aro10 | Ppfor | rsPAR | Pwl | pheA2 | aroG |
| 2D22 | 2.35 | Pfer | cgAroE | Pfer | abPPDC | Pfer | blPAR | Pwl | pheA2 | aroG |
| 2D07 | 2.33 | Pfer | ecAroE | Pwl | kivD | Pfer | blPAR | Pwl | pheA2 | aroG |
| 2D24 | 2.33 | Ppfor | cgAroE | Pwl | aro10 | Ppfor | blPAR | Pwl | pheA2 | aroG |
| 2D03 | 2.32 | Pfer | ecAroE | Pfer | abPPDC | Pfer | blPAR | Pwl | pheA2 | aroG |
| 1C29 | 2.29 | Ppfor | ecAroE | Pfer | abPPDC | Pfer | lePAR | Pwl | pheA1 | aroG |
| 2B26 | 2.28 | Pwl | cgAroE | Ppfor | abPPDC | Pfer | adh6 | Pwl | pheA2 | aroG |
| 2C38 | 2.27 | Ppfor | cgAroE | Ppfor | abPPDC | Pfer | ecPAR | Pwl | pheA2 | aroG |
| 2A27 | 2.26 | Pfer | ecAroE | Pwl | aro10 | Ppfor | rsPAR | Pwl | pheA2 | aroG |
| 2C12 | 2.26 | Ppfor | ecAroE | Pwl | aro10 | Pfer | Adh6 | Pwl | pheA2 | aroG |
| 2B27 | 2.24 | Pwl | ecAroE | Ppfor | abPPDC | Pwl | ecPAR | Pwl | pheA2 | aroG |

Syngas derived from gasification of waste materials such as biomass, forestry residues, and municipal solid waste often contains toxic contaminants. For example, methane, ethane, ethylene, and acetylene are among the detected contaminants and they are known to be toxic to microbes at ppm levels. To assess the robustness of the de novo 2-PE biosynthesis in engineered *C. autoethanogenum*, strain sFA212 was subjected to continuous CSTR run using syngas derived from corn-stover. This "real" syngas was pre-treated using a gas treatment system, resulting in a post-treatment gas composition of 23.3% $H_2$, 38.7% CO, 19.6% $CO_2$, and 18.4% $N_2$. Due to the limited availability of the real syngas, synthetic blended gas (with similar gas composition) was used initially to establish a steady state fermentation culture before the gas supply was switched to real syngas on day 6.9.

The results of real syngas fermentation are shown in (FIGS. 11A-C), with real syngas being used between day 6.9 and 10.9 (total of 4 days). In order to enable longer continuous CSTR run, several real syngas bottles were used with slightly different gas compositions, which resulted in the observed gas uptake fluctuations (FIG. 11B). Following the switch to real syngas, the 2-PE production continued to increase and reached a steady state on day 10. The average titer and productivity of 2-PE between day 8.0 and day 13.7 is 208 mg/L and 11.95 mg/L/h, respectively.

Sequences

TABLE 4

Sequences for the nucleic acids described in the Examples and summarized in Table 2.

| SEQ ID NO | Description | Sequence |
|---|---|---|
| 1 | LZ1561 codon adapted nucleotide sequence of kivD_la | ATGTATACAGTTGGAGATTATTTATTAGATAGATTACATGAATTAGG AATAGAAGAAATATTTGGTGTACCAGGAGATTACAATTTACAATTTT TAGATCAAATAATAAGTAGAAAAGATATGAAATGGGTGGGGAATGCA AATGAGTTAAATGCAAGTTACATGGCTGATGGATATGCAAGAACTAA AAAGGCAGCTGCATTCCTTACAACCTTTGGAGTAGGAGAACTAAGTG CAGTAAATGGGCTTGCAGGTTCATATGCTGAAAACTTACCTGTAGTT GAAATCGTAGGTAGTCCAACTTCAAAAGTCCAAAACGAAGGAAAATT TGTACACCATACTCTGGCTGACGGAGATTTTAAACATTTTATGAAAA TGCATGAACCTGTAACAGCTGCGAGAACCCTTTTAACTGCGGAAAAT GCTACAGTTGAAATAGATAGAGTTTTAAGTGCTCTTTTAAAGGAGAG AAAGCCTGTTTATATTAATCTTCCCGTAGATGTAGCTGCTGCTAAGG CAGAGAAACCTTCTTTACCTTTGAAAAAGGAAAACAGCACTTCTAAT ACTTCCGATCAAGAGATATTAAATAAAATTCAAGAATCCTTAAAAAA TGCTAAAAAACCTATAGTTATTACAGGACACGAAATAATATCTTTTG GCCTAGAAAAAACAGTAAGTCAGTTTATAAGTAAAACAAAATTACCT ATAACTACTTTAAATTTCGGTAAGAGTTCTGTTGACGAGGCACTTCC AAGTTTTTTAGGAATATATAATGGAAAATTGAGTGAACCAAATCTAA AAGAGTTTGTAGAGTCAGCAGACTTTATACTAATGCTTGGTGTGAAG TTAACTGATTCAAGTACTGGAGCCTTTACTCATCATTTAAATGAAAA CAAAATGATAAGTTTAAACATTGATGAGGGCAAAATTTTCAATGAGT CAATTCAAAATTTTGATTTTGAATCTTTAATTTCATCACTTCTGGAT TTATCAGAAATAGAGTATAAAGGCAAATATATTGATAAGAAACAAGA AGATTTTGTTCCAAGTAATGCACTATTAAGTCAAGATAGGTTATGGC AGGCAGTTGAAAATTTAACTCAAAGCAATGAGACTATAGTAGCAGAA CAGGGAACATCACTATTTGGAGCGTCTTCTATTTTTCTTAAGCCAAA AAGTCATTTTATAGGTCAGCCATTATGGGGTTCTATAGGATATACTT TTCCAGCTGCATTAGGATCACAGATAGCAGATAAAGAATCTAGACAT CTTTTGTTCATAGGCGATGGTTCCTTGCAGTTAACAGTCCAGGAATT AGGACTTGCAATAAGAGAAAAAATAAACCCTATTTGTTTCATAATAA ATAATGATGGATATACTGCTGAAAGAGAAATACATGGACCAAATCAG AGCTATAATGATATTCCAATGTGGAACTATTCTAAACTGCCTGAATC ATTTGGGGCTACAGAAGAAAGGGTAGTGTCAAAAATAGTTAGAACAG AAAATGAATTTGTAAGTGTCATGAAAGAAGCTCAGGCTGATCCAAAC AGAATGTATTGGATTGAACTCATACTTGCAAAAGAGGATGCTCCAAA AGTATTAAAGAAAATGGGGAAACTTTTTGCTGAACAAAACAAATCTT AA |
| 2 | LZ1561 codon adapted nucleotide sequence of abPPDC | ATGAAATTGGCAGAAGCATTACTCAGAGCATTGAAAGATAGAGGGGC ACAGGCAATGTTTGGTATACCTGGAGATTTTGCACTTCCTTTTTTCA AAGTTGCTGAAGAAACTCAAATACTTCCTTTGCACACACTCTTAGCCAT GAACCTGCTGTAGGTTTTGCAGCAGATGCAGCTGCAAGATATTCTTC TACATTAGGTGTAGCAGCAGTTACTTACGGAGCAGGAGCATTTAATA TGGTAAATGCAGTTGCTGGTGCCTATGCAGAAAAAAGCCCTGTAGTA GTTATATCTGGTGCTCCTGGTACAACAGAAGGAAATGCTGGTCTTTT ACTTCACCATCAGGGAAGAACTTTAGACACTCAATTCCAGGTATTTA AGGAGATAACAGTTGCCCAGGCTAGATTAGATGATCCTGCTAAGGCT CCTGCCGAAATAGCAAGAGTACTTGGTGCTGCTAGAGCGCTCTCAAG ACCAGTTTATTTAGAAATACCTAGAAATATGGTAAATGCTGAAGTAG AACCAGTAGGGGATGATCCAGCATGGCCAGTAGACAGAGATGCTTTA GCTGCCTGTGCTGATGAAGTACTTTGCAGCTATGAGATCTGCTACAAG TCCTGTTTTAATGGTTTGTGTAGAGGTTAGAAGATATGGACTTGAAG CAAAAGTTGCTGAATTAGCACAGAGACTTGGAGTACCTGTAGTAACA ACATTTATGGGACGCGGATTACTTGCAGATGCACCCACTCCTCCTTT AGGAACTTATATAGGAGTAGCAGGAGATGCAGAAATAACTAGATTAG |

TABLE 4-continued

Sequences for the nucleic acids described in the
Examples and summarized in Table 2.

| SEQ ID NO | Description | Sequence |
|---|---|---|
| | | TGGAAGAATCAGATGGATTATTTTTACTTGGAGCAATTCTTTCAGAT
ACAAATTTTGCAGTCTCTCAAAGAAAAATAGACTTAAGAAAAACCAT
TCATGCATTTGATCGTGCAGTTACCCTTGGATATCATACTTATGCTG
ACATTCCTTTAGCAGGACTAGTTGATGCCCTTCTAGAAAGACTTCCT
CCTTCAGACAGGACGACTAGAGGTAAAGAGCCACATGCCTATCCTAC
AGGTCTTCAGGCTGATGGAGAACCAATAGCTCCAATGGACATTGCCC
GTGCTGTGAACGACAGAGTACGTGCTGGTCAGGAACCTCTTTTAATA
GCAGCTGATATGGGTGACTGCTTATTTACAGCTATGGATATGATAGA
TGCTGGTCTTATGGCACCGGGCTATTATGCAGGCATGGGATTTGGAG
TTCCAGCTGGTATTGGTGCTCAATGTGTATCAGGCGGCAAAAGAATA
CTTACTGTTGTTGGTGACGGAGCATTCCAGATGACAGGCTGGGAACT
TGGAAATTGTAGAAGATTAGGTATTGACCCTATAGTAATACTTTTTA
ATAATGCTTCTTGGGAAATGTTAAGAACATTTCAGCCTGAAAGTGCT
TTTAATGATTTAGATGATTGGAGATTTGCAGATATGGCTGCTGGAAT
GGGCGGCGACGGTGTAAGAGTCAGGACAAGGGCTGAGTTGAAGGCTG
CATTAGATAAAGCATTTGCCACAAGGGGCAGATTCCAGCTTATAGAA
GCAATGATACCGAGAGGTGTGCTTTCCGATACCCTTGCTAGATTTGT
TCAAGGCCAAAAGAGGCTTCACGCAGCTCCTAGAGAATAA |
| 3 | LZ1561 codon adapted nucleotide sequence of adh6 | ATGTCGTATCCTGAAAAATTTGAAGGTATAGCTATTCAATCCCATGA
AGACTGGAAAAATCCCAAAAAAACAAAGTACGACCCAAAACCTTTCT
ATGACCATGATATAGATATAAAGATTGAAGCATGTGGAGTATGTGGA
AGTGATATTCATTGTGCGGCAGGCCATTGGGGAAATATGAAAATGCC
ATTAGTTGTGGGACATGAAATTGTTGGAAAAGTTGTAAAGTTAGGTC
CTAAATCAAATTCTGGACTAAAAGTTGGACAGAGAGTTGGAGTTGGT
GCTCAAGTATTTTCTTGTTTAGAGTGTGATAGATGTAAAAATGACAA
TGAACCTTACTGTACTAAATTTGTTACTACTTATTCACAACCTTATG
AAGATGGATATGTAAGTCAGGGAGGCTATGCAAACTATGTTAGAGTT
CACGAGCACTTTGTAGTACCTATTCCAGAAAATATTCCATCTCACTT
AGCAGCTCCTCTTTTATGCGGTGGACTTACTGTTTATAGTCCACTTG
TTAGAAATGGTTGTGGTCCTGGGAAAAAAGTCGGAATAGTTGGACTT
GGCGGAATTGGAAGTATGGGAACTTTAATAAGTAAAGCTATGGGAGC
TGAAACTTATGTAATTTCTAGATCATCAAGAAAGAGAGAAGATGCAA
TGAAGATGGGAGCAGATCACTATATTGCTACATTAGAAGAGGGGGAT
TGGGGGGAAAAGTACTTTGATACTTTTGATTTAATTGTCGTATGTGC
TTCAAGTCTTACAGATATAGATTTTAATATAATGCCAAAAGCAATGA
AAGTTGGTGGACGAATAGTATCTATAAGTATACCTGAACAGCACGAA
ATGTTATCTTTAAAACCTTATGGACTAAAGGCTGTATCTATTTCTTA
TTCTGCATTGGGGTCTATTAAAGAATTGAATCAATTATTAAAACTGG
TTAGTGAAAAAGATATAAAAATTTGGGTAGAAACACTTCCTGTAGGT
GAGGCAGGAGTCCATGAGGCTTTTGAGAGAATGGAAAAAGGTGATGT
AAGATATAGATTTACACTTGTTGGCTATGATAAAGAGTTTTCTGATT
AG |
| 4 | LZ1561 codon adapted nucleotide sequence aro10 | ATGGCACCAGTAACAATTGAAAAATTTGTAAATCAAGAGGAAAGACA
TTTGGTATCAAACCGTTCAGCTACAATTCCATTTGGGGAATATATAT
TCAAGAGACTTTTGAGTATAGATACAAAAAGTGTTTTTGGAGTTCCT
GGAGATTTTAATCTTTCCCTCTTAGAGTACTTATATTCACCATCAGT
TGAATCTGCAGGATTGAGATGGGTTGGTACTTGTAATGAACTAAATG
CTGCTTATGCAGCAGATGGTTATAGCAGATATTCAAATAAAATAGGG
TGTCTTATAACAACTTATGGAGTAGGCGAGTTATCTGCATTGAATGG
AATAGCAGGATCATTTGCAGAAAATGTTAAAGTGCTTCACATTGTAG
GCGTTGCTAAGAGCATAGATAGCCGATCTTCAAATTTCTCAGATAGA
AATCTACATCATCTTGTTCCACAACTACATGATTCAAACTTCAAAGG
ACCTAATCATAAAGTTTATCATGATATGGTAAAAGATAGGGTAGCAT
GCTCTGTTGCTTATCTTGAAGACATAGAAACTGCTTGTGATCAAGTT
GATAATGTAATAAGAGATATATACAAATACTCAAAACCAGGATATAT
ATTTGTTCCAGCAGATTTGCAGATATGTCAGTTACATGTGATAACT
TAGTTAATGTACCAAGAATAAGTCAACAGGATTGCATAGTTTATCCA
TCTGAAAATCAGTTAAGTGACATTATAAATAAAATAACTTCCTGGAT
TTACAGTTCTAAAACCCCAGCCATTTTAGGTGATGTATTAACTGATA
GATATGGTGTATCAAATTTTTTAAATAAACTTATATGTAAGACTGGA
ATCTGGAATTTTTCAACTGTTATGGGTAAATCAGTTATAGATGAAAG
TAATCCAACTTACATGGGTCAATATAATGGAAAAGAAGGTCTTAAAC
AAGTGTATGAACATTTTGAGCTTTGTGATTTAGTGCTTCACTTTGGT
GTGGACATAAACGAAATTAACAATGGACATTATACTTTTACTTATAA
ACCTAACGCAAAAATAATACAATTTCATCCAAACTATATAAGACTTG
TAGATACAAGACAAGGAAATGAGCAAATGTTCAAAGGCATAAACTTT
GCTCCTATACTAAAAGAGCTGTATAAAAGAATAGATGTATCAAAGTT
GTCACTTCAGTATGATTCAAATGTAACTCAATACACTAATGAGACAA
TGAGATTAGAAGATCCCACTAATGGACAATCTTCAATTATTACCCAG
GTACATCTTCAAAAAACGATGCCAAAATTCCTCAATCCAGGAGATGT
TGTTGTCTGTGAAACAGGTTCTTTTCAATTTTCTGTGAGGGATTTTG
CATTCCCTTCTCAATTAAAATATATATCTCAAGGATTTTTCCTTTCA |

TABLE 4-continued

Sequences for the nucleic acids described in the
Examples and summarized in Table 2.

| SEQ ID NO | Description | Sequence |
|---|---|---|
| | | ATCGGTATGGCATTACCAGCTGCATTGGGAGTTGGAATAGCAATGCA AGACCATTCAAATGCTCATATAAATGGCGGCAATGTTAAAGAGGATT ATAAACCAAGACTTATTTTATTTGAAGGAGATGGTGCTGCACAAATG ACAATTCAAGAACTATCTACAATATTAAAATGTAATATTCCTCTTGA AGTAATAATTTGGAACAACAATGGATATACTATTGAAAGAGCAATAA TGGGTCCAACAAGATCTTATAATGATGTAATGTCGTGGAAATGGACT AAATTATTTGAGGCATTTGGTGATTTCGATGGAAAGTATACAAATTC TACTTTGATACAGTGTCCTTCAAAGTTAGCTTTAAAACTTGAAGAAC TCAAGAACTCAAATAAAAGATCTGGAATAGAATTATTAGAAGTTAAA CTTGGAGAGTTAGACTTCCCTGAGCAACTAAAATGCATGGTAGAAGC AGCAGCACTTAAGAGAAACAAAAAATAA |
| 5 | LZ1561 codon adapted nucleotide sequence of phenylacetalyhde reductase (blPAR) from *Brevibacterium linens* | ATGAAAGCAAGTTTGGCAACGGCAATTGGCGGCGAATTCACAGTACA TGACGTAGTAATAGATGACCCACAAGGAAGAGAGGTCCTTGTGGATG TGAAAGCTTCAGGATTATGTCATTCTGATTTACACTTAATAGATCAT GATTTCGGTCTCCCTCTTCCAGCTGTAGGCGGCCATGAAATTTCAGG TGTAGTGAGAAGTGTAGGACCAGGCGTTACCAGTATGTCTGTTGGAG ACCATGTTGTAGCTTGTCTTATAACTTTTTGCGGTGCATGTGCAGAA TGCCTTTCAGGAAAAACTACTTTATGTTCAAATCCTACTGCTGTAGC AAGAAAAGAAGGAGAAAAGCCAAGAGTTTCATTCCCTGATGGTCAGG AAATTGCACAATCAGTTAATGTTGGCGGCTTTGCAGAACAAGTACTA GTTCATGAAATCAGCTTGCAGTAGTAAACAATCAGATACCTTTCCC TCAGGCAGCACTTTTAGGGTGCTCAGTTGTCACAGGAGCAGGAGCAG CTATAAATACAGCTCATGTAAGACCAGGGGATACAGTAGCGGTTATA GGAACAGGCGGCATAGGATTAAACGCAATAAGCGGAGCAAGATTAGC AGGGGCTAAGCACATTATAGCTATTGATATAGTTGATTCTAAATTAG AGGCTGCAAAAAAGTTTGGAGCTACAGATCTTATAAATTCATCAACT ACTGATCCAGTGGCAGCAGTTCAAGAATTAACTGGCGGCGTAGATCA TGCATTTGAAGTAATTGGATTAGAAGCTACGCAGAGGCAAGTTCAGC AATTAACAAAACCAGGCGGCACGGCATATTTAATAGGCATAGCACCA CCAGGAACAACTACTGAATTTACATCATCATTAGATAGTTTGTTTGC TCAAAGAAGACTGCAGGCTGTTTTGATGGGTAGTAGTAATGTTAAAA GAGATATAGCATTATATGCAGACTTGTATGTTCAGGGACGTTTTGAA TTAGATCATTTAGTATCAAGAGAAATATCCATAAATGAGATAAATGA TGGTTATGAAGCATTAAAAAAAGGTGAAGTTATACGTTCAGTTATAA CCAGTTTTTAA |
| 6 | LZ1561 codon adapted nucleotide sequence of phenylacetalyhde reductase (ecPAR) from *Escherichia coli* | ATGTCAATGATAAAATCATATGCAGCAAAAGAAGCAGGCGGCGAATT AGAAGTTTACGAATATGATCCAGGGGAATTAAGGCCTCAAGATGTAG AAGTTCAAGTTGATTACTGTGGAATATGCCATTCCGATTTATCTATG ATAGATAATGAATGGGGATTTAGTCAGTATCCTCTTGTAGCAGGACA TGAAGTTATTGGCAGAGTTGTAGCTCTTGGTTCAGCAGCTCAGGATA AGGGCTTACAGGTAGGTCAGAGAGTAGGGATAGGCTGGACTGCCCGT TCGTGTGGACACTGCGATGCATGTATCAGTGGAAATCAAATAAATTG TGAACAAGGTGCAGTTCCAACTATAATGAATAGGGGCGGCTTTGCAG AAAAAATTAAGAGCAGATTGGCAATGGGTAATTCCTCTTCCAGAAAAC ATAGATATAGAATCAGCAGGTCCTCTCCTTTGTGGCGGCATTACAGT ATTTAAACCTCTTCTTATGCATCATATTACTGCTACATCAAGAGTAG GAGTAATCGGTATAGGCGGCCTTGGACATATAGCAATTAAACTTCTT CATGCTATGGGTTGTGAAGTTACGGCATTTAGTTCAAATCCAGCTAA AGAGCAAGAAGTTCTTGCTATGGGTGCCGACAAGGTAGTTAACAGTA GGGATCCACAGGCACTGAAAGCACTGGCGGGACAATTTGATCTTATA ATAAATACAGTAAACGTTTCTCTAGATTGGCAACCATATTTTGAGGC ATTAACTTATGGCGGCAATTTCCATACAGTTGGAGCCGTTCTTACAC CACTATCTGTTCCAGCTTTTACACTTATAGCAGGAGATCGTAGTGTT TCCGGCTCTGCAACTGGTACTCCTTATGAACTTAGAAAACTTATGAG ATTTGCAGCAAGATCTAAAGTTGCACCTACCACAGAGCTTTTCCCTA TGAGCAAGATAAATGATGCAATTCAGCACGTTAGAGATGGAAAAGCA AGATATAGGGTTGTGTTAAAGGCTGATTATTAG |
| 7 | LZ1561 codon adapted nucleotide sequence of phenylacetalyhde reductase (rrPAR) from *Rhodococcus ruber* | ATGAAAGCTTTGCAATATACAGAAATAGGAAGTGAACCAGTAGTAGT AGATGTACCAACACCAGCGCCAGGACCAGGAGAGATCTTATTAAAGG TAACTGCAGCAGGACTTTGTCATTCAGATATATTTGTAATGGATATG CCTGCTGAACAGTATATTTATGGCCTTCCATTAACGCTTGGCCATGA GGGTGTTGGAACAGTTGCAGAATTAGGGGCAGGTGTAACAGGATTTG AAACAGGTGATGCTGTTGCTGTTTATGGACCTTGGGGATGCGGTGCC TGCCATGCTTGTGCCCGTGGAAGGGAAACTATTGTACTAGAGCTGC AGAGTTAGGAATAACACCCCCTGGACTGGGATCACCTGGAAGTATGG CAGAGTATATGATTGTAGATTCTGCAAGACATTTAGTTCCTATAGGT GATTTGGATCCTGTTGCAGCTGTTCCTCTTACAGATGCTGGATTGAC ACCTTATCATGCAATAAGTAGAGTGTTACCGCTTCTTGGACCAGGAT CTACAGCTGTAGTTATAGGAGTTGGCGGCTTAGGACATGTTGGCATC CAAATATTAAGAGCAGTGTCAGCAGCAAGAGTTATAGCAGTTGATTT AGATGATGACAGATTAGCTTTAGCAAGAGAAGTTGGTGCAGATGCAG |

TABLE 4-continued

Sequences for the nucleic acids described in the
Examples and summarized in Table 2.

| SEQ ID NO | Description | Sequence |
|---|---|---|
| | | CTGTTAAAAGTGGAGCAGGAGCAGCAGATGCTATTCGTGAACTTACA GGCGGCGAAGGAGCAACTGCTGTGTTTGATTTTGTAGGAGCTCAGAG TACAATTGATACTGCACAGCAGGTAGTAGCAATAGACGGCCATATAT CCGTAGTTGGTATTCATGCAGGTGCTCATGCAAAAGTAGGTTTTTTT ATGATACCTTTTGGAGCTTCTGTTGTAACTCCTTACTGGGGTACCCG TTCTGAACTTATGGATGTAGTAGATCTTGCAAGAGCAGGCAGACTTG ATATACATACTGAGACTTTTACTTTAGATGAAGGTCCGACTGCTAT AGAAGACTAAGAGAAGGTTCCATAAGAGGTAGGGGAGTAGTAGTGCC TGGATAA |
| 8 | LZ1561 codon adapted nucleotide sequence of phenylacetalyhde reductase (rsPAR) from Rhodococcus sp. ST-10 | ATGAAAGCAATTCAATACACAAGAATAGGAGCAGAACCAGAACTTAC AGAAATACCAAAACCAGAGCCAGGACCAGGGGAAGTTCTTCTTGAAG TAACTGCAGCTGGAGTATGTCACAGTGATGATTTTATAATGTCGCTG CCTGAAGAACAGTATACATATGGACTACCACTTACATTAGGTCATGA AGGTGCAGGAAAAGTAGCAGCTGTAGGTGAGGGAGTAGAAGGTTTAG ACATAGGAACTAATGTAGTAGTATATGGACCTTGGGGATGTGGAAAT TGCTGGCACTGCTCTCAAGGCTTGGAAAACTACTGTTCAAGAGCTCA GGAACTTGGAATAAATCCACCTGGACTTGGTGCACCAGGTGCATTAG CTGAATTTATGATTGTAGATTCACCACGTCATTTAGTGCCTATAGGA GATTTGGATCCTGTTAAAACTGTACCACTAACTGATGCAGGACTTAC ACCTTATCATGCTATAAAAGAAGTTTACCAAAGTTAAGAGGCGGCT CCTATGCCGTTGTAATAGGAACAGGCGGCCTTGGACATGTAGCTATC CAATTATTAAGACATTTGTCTGCAGCTACTGTTATAGCACTTGACGT TTCAGCAGATAAATTGGAACTTGCTACTAAGGTAGGTGCACATGAAG TTGTATTATCAGACAAGGATGCAGCTGAAAATGTAAGGAAAATTACA GGATCACAAGGAGCAGCCTTAGTTTTAGATTTTGTTGGATATCAACC TACAATTGACACTGCTGGCTGTAGCTGGTGTTGGAAGTGATGTTA CAATAGTAGGTATAGGTGATGGTCAAGCTCATGCAAAGGTAGGTTTC TTTCAAAGTCCTTATGAAGCTTCAGTAACTGTACCTTATTGGGGAGC TAGAAATGAGTTAATAGAACTCATAGATTTAGCTCATGCAGGTATAT TTGATATTTCAGTAGAAACTTTTTCACTTGACAATGGCGCAGAAGCA TATAGAAGATTAGCTGCTGGAACACTTTCAGGAAGAGCAGTAGTAGT TCCAGGATTATAA |
| 9 | LZ1561 codon adapted nucleotide sequence of phenylacetalyhde reductase (lePAR) from Solanum lycopersicum | ATGTCAGTTACAGCAAAAACAGTTTGTGTTACAGGTGCTTCAGGTTA CATTGCTTCATGGTTAGTTAAATTTTTACTTCATTCTGGATATAATG TTAAGGCATCTGTTAGGGATCCAAATGATCCTAAAAAGACCCAGCAT CTATTAAGTCTTGGCGGCGCTAAAGAAAGGCTTCACTTATTTAAGGC AAATCTACTTGAAGAAGGTAGCTTTGATGCTGTTGTAGATGGTTGTG AAGGAGTATTCCACACTGCGTCACCATTTTATTACTCTGTAACTGAC CCACAAGCTGAATTGCTTGATCCAGCTGTAAAAGGTACACTGAACTT GTTAGGAAGTTGTGCAAAGGCACCAAGCGTAAAGAGAGTTGTATTAA CTAGCAGTATTGCTGCTGTTGCATACTCTGGTCAGCCAAGAACCCCA GAAGTAGTTGTAGATGAATCATGGTGGACATCACCAGATTACTGTAA AGAAAAACAACTTTGGTATGTTTTAAGTAAAACTTTAGCTGAAGATG CTGCTTGGAAATTTGTTAAAGAAAAGGGAATAGATATGGTTGTAGTT AATCCAGCTATGGTTATTGGACCACTTTTGCAGCCAACATTAAATAC TAGCTCTGCAGCAGTACTTTCACTTGTAAATGGTGCTGAGACATACC CAAATTCAAGTTTTGGATGGGTAAATGTAAAGGACGTAGCAAATGCT CATATATTAGCATTTGAAAATCCATCCGCCAATGGAAGATATCTTAT GGTAGAAAGAGTAGCTCATTATTCTGATATATTGAAAATTTTAAGAG ATCTATATCCAACTATGCAGTTACCAGAAAAGTGTGCAGATGATAAT CCTCTTATGCAAAATTATCAGGTTTCAAAAGAAAAGGCCAAATCTTT AGGAATAGAATTTACGACTTTAGAAGAATCTATCAAAGAAACTGTTG AATCACTAAAGGAGAAAAAATTCTTTGGCGGCTCGTCCTCCATGTAA |
| 10 | LZ1561 codon adapted nucleotide sequence of AroG from Escherichia coli | ATGAATTATCAAAATGATGATTTAAGAATAAAAGAAATTAAAGAATT ATTACCTCCTGTAGCTTTATTAGAAAAATTTCCTGCAACTGAAAATG CAGCAAATACTGTAGCACATGCAAGAAAAGCAATACATAAAATACTT AAAGGTAATGATGATAGATTATTAGTAGTAATAGGACCTTGTAGTAT ACATGATCCTGTAGCAGCAAAAGAATATGCAACTAGACTTTTAGCAT TAAGAGAAGAATTAAAAGATGAATTAGAAATAGTAATGAGAGTATAT TTTGAAAAACCTAGAACTACTGTAGGATGGAAAGGACTTATAAATGA TCCTCATATGGATAATAGTTTTCAAATAAATGATGGACTTAGAATAG CAAGAAAATTACTTTTAGATATAAATGATAGTGGATTACCTGCAGCT GGTGAATTTTTAGATATGATAACTCCTCAATATTTAGCAGATTTAAT GAGTTGGGGAGCAATTGGAGCAAGAACTACTGAAAGTCAAGTACATA GAGAAGATGCAAGTGGACTTAGTTGTCCTGTAGGATTTAAAAATGGA ACTGATGGAACTATAAAAGTAGCAATAGATGCAATAAATGCAGCTGG TGCACCTCATTGTTTTCTTAGTGTAACAAAATGGGGACATAGTGCAA TAGTAAATACTAGTGGAAATGGTGATTGTCATATAATACTTAGAGGT GGAAAAGAACCTAATTATTCTGCAAAACATGTAGCAGAAGTAAAAGA AGGACTTAATAAAGCTGGACTTCCTCACAGGTAATGATAGATTTTT CTCATGCAAATAGTAGTAAACAATTTAAGAAACAAATGGATGTATGT |

TABLE 4-continued

Sequences for the nucleic acids described in the
Examples and summarized in Table 2.

| SEQ ID NO | Description | Sequence |
|---|---|---|
| | | GCAGATGTATGTCAGCAAATAGCTGGAGGTGAAAAAGCAATAATTGG AGTAATGGTAGAAAGTCATTTAGTAGAAGGTAATCAAAGTTTAGAAA GTGGTGAACCTTTAGCTTATGGAAAAAGTATAACTGATGCATGTATA GGATGGGAAGATACTGATGCACTTCTTAGACAACTTGCAAATGCAGT AAAAGCAAGAAGAGGATAA |
| 11 | LZ1561 codon adapted nucleotide sequence of ecAroE from *Escherichia coli* | ATGGAAACTTATGCAGTATTTGGCAATCCTATAGCACATTCAAATC ACCATTTATACATCAACAATTTGCTCAGCAATTAAATATTGAACATC CTTATGGAAGAGTTTTAGCTCCAATAAATGATTTTATAAATACTTTA AATGCTTTTTTTTCAGCAGGCGGCAAAGGAGCAAATGTAACTGTACC TTTTAAAGAGGAAGCTTTTGCCAGAGCAGATGAGTTAACTGAAAGAG CAGCATTAGCTGGTGCGGTTAATACATTGATGAGACTAGAAGATGGT AGGCTTTTAGGAGATAATACTGATGGGGTAGGTCTTTTGTCTGATCT TGAAAGACTTTCTTTTATAAGACCTGGCCTCCGGATCCTTTTAATAG GTGCAGGCGGCGCATCCAGGGGAGTATTACTTCCATTACTATCACTG GATTGTGCAGTTACTATCACTAACAGAACAGTTTCAAGAGCTGAAGA GCTTGCTAAATTATTTGCACATACAGGATCAATCCAGGCACTTTCCA TGGATGAACTAGAGGGACATGAATTTGACTTAATTATAAATGCGACT AGCAGTGGTATAAGTGGGGATATACCAGCTATTCCCAGCTCTTTAAT ACATCCTGGAATATACTGCTATGATATGTTTTATCAAAAAGGTAAGA CACCGTTCTTAGCTTGGTGTGAACAAGAGGAAGCAAGAGAAATGCA GATGGTCTTGGCATGCTGGTTGCACAAGCAGCTCATGCATTTTTACT ATGGCATGGAGTTTTACCTGATGTTGAACCTGTTATAAAACAGCTGC AAGAAGAATTGTCAGCATAA |
| 12 | LZ1561 codon adapted nucleotide sequence of cgAroE from *Corynebacterium glutamicum* | ATGGGATCACATATAACTCACAGAGCAGCAGTTTTAGGCTCACCAAT TGAACATTCAAAATCACCAGTGCTTCATAATACAGGATATAAAGCTT TAGGACTTGATCAATGGGAATATGCAGGTTTGAATGCACAGGAGAT ATGTTACCGGGCATAGTTTCAGGAGCAGATGAAACTTATCGAGGATT TTCTGTTACAATGCCTTCTAAATTTGCTGCTTTAGAATTTGCAGATG AAGTAACTGAAAGAGCAAGAGCTATTGGATCAGCAAATACATTACTT AGAACTGAAACAGGATGGAGAGCGGATAATACTGATGTGGATGGAAT AAGAGGTGCATTAGGTGAATTGTTAGGAAGTGCATCTCTTGCAGGAA AACATGCTATTGTAATAGGATCAGGCGGCACTGCAAGACCTGCAATT TGGGCACTTATAGAAGCAGGAGTAGCAAGAATAACTGTACTTAATAG ATCAGATAGAACTGCTGAACTTCAAACTTTATTTGATGAAACACCAA CTACGTTAGCATATGCTCCACTTGAGCACTTGGATATTGAAGCTGAC GTTAGTTTCTACTGTTCCTTCAGCTGCTATAGCTGGTCTTGAAGA TACACTGGCTATAGCACCAGTGTTGGATGTTATATATGATCCATGGC CAACTCCTTTAGTAGAAGTTGCAAGAGCTAAAGGACTTAAGGCTGTA GGCGGCCACGTAATGTTGGCCCATCAATCATATGGTCAATTTGAACA GTTTACAGGAATGGATGCTCCAAGGGATGCAATGAGAGAAGCTTTAG AAGAATCACTTGGAATAAGTGAGGAACATTAG |
| 13 | LZ1561 codon adapted nucleotide sequence of pheA1 from *Escherichia coli* | ATGACTAGTGAAAATCCATTACTTGCTTTAAGAGAAAAAATATCTGC CCTTGATGAAAAATTACTTGCTTTATTAGCAGAAAGAAGAGAGCTTG CAGTTGAGGTAGGTAAGGCAAAGTTGCTTTCGCACAGGCCTGTTAGA GATATTGATAGGGAAAGAGATCTTTTGGAAAGATTAATAACTCTTGG TAAGGCTCATCATTTGGATGCTCATTATATAACAAGATTATTTCAGC TCATAATAGAAGACTCAGTTCTTACTCAACAGGCATTGCTTCAACAA CATTTGAATAAGATCAATCCTCACTCAGCCAGAATAGCTTTTTTAGG CCCAAAAGGTTCCTATTCACATCTGGCTGCTAGACAATATGCAGCAA GGCATTTTGAACAGTTCATTGAATCAGGGTGTGCTAAATTTGCAGAT ATATTTAACCAGGTAGAAACAGGTCAAGCCGATTATGCTGTAGTACC TATAGAAAATACGTCGAGTGGTGCTATTAATGATGTATATGATCTTT TACAGCACACTAGCCTATCCATAGTAGGAGAAATGACTTTAACTATA GATCACTGCCTTTTAGTATCAGGTACTACAGATCTTTCAACTATAAA TACAGTATATTCTCATCCACAGCCATTTCAACAATGTAGTAAATTCC TAAACAGATATCCTCACTGGAAGATTGAATATACTGAAAGTACCAGT GCAGCAATGGAAAAAGTTGCACAGGCTAAATCACCACATGTAGCTGC ATTAGGTTCTGAGGCTGGCGGCACGTTGTATGGATTACAAGTACTAG AAAGAATAGAAGCCAATCAAAGGCAAAATTTTACAAGATTTGTGGTT TTGGCAAGAAAAGCAATAAATGTTTCAGATCAAGTCCCAGCAAAAAC TACATTACTAATGGCTACAGGACAACAGGCTGGGGCTTTAGTTGAGG CTTTATTAGTGTTGAGAAATCACAATTTAATAATGACTAGGCTTGAA TCAAGACCTATTCATGGAAATCCTTAA |
| 14 | LZ1561 codon adapted nucleotide sequence of pheA2 from *Escherichia coli* | ATGACATCAGAAATCCATTATTGGCACTTAGAGAAAAGATATCAGC ACTTGACGAAAAATTACTTGCATTATTGGCAGAGAGAAGAGAGCTTG CTGTTGAAGTTGGAAAGGCTAAGCTGTTGTCCCACCGTCCAGTTAGA GATATTGACAGAGAACGGGACTTATTAGAAAGACTCATTACATTAGG AAAGGCTCATCATTTGGATGCACATTATATTACAAGATTATTTCAGC TCATAATAGAAGATTCAGTATTAACTCAACAGGCTTTACTTCAACAG CACTTAAATAAAATAAATCCACATTCAGCTAGGATTGCATTCTTAGG |

TABLE 4-continued

Sequences for the nucleic acids described in the
Examples and summarized in Table 2.

| SEQ ID NO | Description | Sequence |
|---|---|---|
| | | ACCAAAAGGAAGTTATAGTCATCTTGCTGCAAGACAATATGCAGCAA
GACACTTTGAACAATTTATTGAATCAGGATGTGCTAAATTTGCAGAT
ATCTTCAATCAAGTAGAAACAGGTCAGGCTGATTATGCAGTAGTTCC
AATAGAAAATACGTCAAGCGGTGCTATAAATGATGTATATGATTTAC
TTCAGCATACAAGCTTATCTATAGTTGGTGAGATGACATTGACTATA
GATCACTGCTTACTTGTAAGTGGAACTACAGATTTGTCCACTATAAA
TACTGTTTACAGCCATCCACAGCCATTTCAACAGTGTAGTAAATTTT
TAAATAGATATCCACACTGGAAAATAGAATACACAGAAAGTACTTCC
GCAGCAATGGAAAAGGTTGCACAGGCAAAGTCTCCTCACGTTGCAGC
ATTAGGTAGTGAAGCAGGCGGCACACTTTATGGACTTCAAGTACTCG
AAAGGATTGAAGCAAACCAAAGGCAAAATTTTACTAGATTTGTTGTA
CTTGCCAGAAAGGCTATAAATGTAAGTGATCAGGTACCAGCTAAAAC
TACTTTACTTATGGCAACAGGACAACAGGCAGGAGCACTAGTAGAAG
CACTTTTAGTATTGAGAAATCATAATCTCATAATGACGAGGTTAGAG
TCAAGACCAATTCATGGTAATCCAAGAGAGGAAATGTTTTACCTTGA
TATCCAAGCAAATCTTGAATCAGCAGAAATGCAGAAAGCATTAAAGG
AACTGGGTGAAATAACAAGATCAATGAAAGTGCTTGGATGTTATCCT
TCTGAAAATGTGGTACCTGTAGATCCAACTTAA |

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgement that that prior art forms part of the common general knowledge in the field of endeavor in any country.

The use of the terms "a" and "an" and "the" and similar referents in the context of describing the methods and compositions of the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. The term "consisting essentially of" limits the scope of a composition, process, or method to the specified materials or steps, or to those that do not materially affect the basic and novel characteristics of the composition, process, or method. The use of the alternative (e.g., "or") should be understood to mean either one, both, or any combination thereof of the alternatives. As used herein, the term "about" means ±20% of the indicated range, value, or structure, unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. For example, any concentration range, percentage range, ratio range, integer range, size range, or thickness range is to be understood to include the value of any integer within the recited range and, when appropriate, fractions thereof (such as one tenth and one hundredth of an integer), unless otherwise indicated.

All methods described herein can be performed in any suitable order unless otherwise indicated herein or otherwise clearly contradicted by context. The use of any and all examples, or exemplary language (e.g., "such as") provided herein, is intended merely to better illuminate the methods and compositions of the disclosure and does not pose a limitation on the scope of the disclosed methods and compositions unless otherwise claimed. No language in the specification should be construed as indicating any non-claimed element as essential to the practice of the disclosed methods and compositions.

Preferred embodiments of the disclosure are described herein. Variations of those preferred embodiments may become apparent to those of ordinary skill in the art upon reading the foregoing description. The inventors expect skilled artisans to employ such variations as appropriate, and the inventors intend for the disclosed methods and compositions to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosed methods and compositions unless otherwise indicated herein or otherwise clearly contradicted by context.

The invention claimed is:

1. A C1-fixing microorganism that produces 2-phenylethanol, wherein the microorganism comprises:

(a) a heterologous enzyme that converts phenylpyruvate to phenylacetaldehyde, wherein the enzyme is a decarboxylase; and (b) a heterologous enzyme that converts phenylacetaldehyde to 2-phenylethanol, wherein the enzyme is a phenylacetaldehyde; wherein the heterologous enzyme in (a) is encoded by a nucleic acid with at least 90% identity to SEQ ID NO: 1, 2, or 4; and the heterologous enzyme in (b) is encoded by a nucleic acid with at least 90% identity to SEQ ID NO: 3, 5, 6, 7, 8, or 9; and wherein the microorganism is a Wood-Ljungdahl microorganism.

2. The microorganism of claim 1, wherein the microorganism produces natively phenylpyruvate.

3. The microorganism of claim 1, wherein the microorganism comprises one or more of:
(c) a native enzyme that converts acetyl-CoA to pyruvate;
(d) a native enzyme that converts pyruvate to phosphoenolpyruvate;
(e) a native enzyme that converts phosphoenolpyruvate and erythrose-4-phosphate to 2-dehydro-3-deoxy-D-arabino-heptonate 7-phosphate;
(f) a native enzyme that converts 2-dehydro-3-deoxy-D-arabino-heptonate 7-phosphate to 3-dehydroquinate;
(g) a native enzyme that converts 3-dehydroquinate to 3-dehydroshikimate;
(h) a native enzyme that converts 3-dehydroshikimate to shikimate;
(i) a native enzyme that converts shikimate to shikimate 3-phosphate;
(j) a native enzyme that converts shikimate 3-phosphate to 5-O-(1-carboxyvinyl)-shikimate 3-phosphate;
(k) a native enzyme that converts 5-O-(1-carboxyvinyl)-shikimate 3-phosphate to chorismate; or
(l) a native enzyme that converts chorismate to phenylpyruvate.

4. The microorganism of claim 3, wherein:
(c) the native enzyme that converts acetyl-CoA to pyruvate is pyruvate: ferredoxin oxidoreductase;
(d) the native enzyme that converts pyruvate to phosphoenolpyruvate is pyruvate phosphate dikinase;
(e) the native enzyme that converts phosphoenolpyruvate and erythrose-4-phosphate to 2-dehydro-3-deoxy-D-arabino-heptonate 7-phosphate is 2-dehydro-3-deoxy-D-arabino-heptonate 7-phosphate synthase;
(f) the native enzyme that converts 2-dehydro-3-deoxy-D-arabino-heptonate 7-phosphate to 3-dehydroquinate is 3-dehydroquinate synthase;
(g) the native enzyme that converts 3-dehydroquinate to 3-dehydroshikimate is 3-dehydroquinate dehydratase;
(h) the native enzyme that converts 3-dehydroshikimate to shikimate is shikimate dehydrogenase;
(i) the native enzyme that converts shikimate to shikimate 3-phosphate is shikimate kinase;
(j) the native enzyme that converts shikimate 3-phosphate to 5-O-(1-carboxyvinyl)-shikimate 3-phosphate is 5-enolpyruvylshikimate 3-phosphate synthase;
(k) the native enzyme that converts 5-O-(1-carboxyvinyl)-shikimate 3-phosphate to chorismate is chorismate synthase; or
(l) the native enzyme that converts chorismate to phenylpyruvate is bi-functional chorismate mutase/prephenate dehydratase.

5. The microorganism of claim 1, wherein the microorganism further comprises one or more of:
(e) a heterologous enzyme that converts phosphoenolpyruvate and erythrose-4-phosphate to 2-dehydro-3-deoxy-D-arabino-heptonate 7-phosphate;
(h) a heterologous enzyme that converts 3-dehydroshikimate to shikimate; or
(l) a heterologous enzyme that converts chorismate to phenylpyruvate.

6. The microorganism of claim 5, wherein:
(e) the heterologous enzyme that converts phosphoenolpyruvate and erythrose-4-phosphate to 2-dehydro-3-deoxy-D-arabino-heptonate 7-phosphate is 2-dehydro-3-deoxy-D-arabino-heptonate 7-phosphate synthase;
(h) the heterologous enzyme that converts 3-dehydroshikimate to shikimate is shikimate dehydrogenase; or
(l) the heterologous enzyme that converts chorismate to phenylpyruvate is bi-functional chorismate mutase/prephenate dehydratase.

7. The microorganism of claim 1, wherein the microorganism comprises: ecAroE, abPPDC, lePAR, pheA1, and aroG.

8. The microorganism of claim 1, wherein the nucleic acid encoding the enzymes of (a) and (b) are heterologous genes and promoters of combinatorial strains.

9. The microorganism of claim 1, wherein the microorganism ferments a gaseous substrate comprising CO, $CO_2$, and/or $H_2$ to produce 2-phenylethanol.

10. The microorganism of claim 9, wherein the gaseous substrate comprises syngas or industrial waste gas.

11. The microorganism of claim 9, wherein the microorganism does not produce any other C3+ alcohols.

12. The microorganism of claim 11, wherein the microorganism does not produce any other C3, C4, C5, C6, C7, C8, C9, or C10 alcohols.

13. A method of producing 2-phenylethanol comprising culturing the microorganism of claim 1 in the presence of a gaseous substrate, wherein the gaseous substrate comprises a C1-carbon source comprising CO, $CO_2$, and/or $H_2$.

* * * * *

SEQUENCE LISTING

<160> NUMBER OF SEQ ID NOS: 14

<210> SEQ ID NO 1
<211> LENGTH: 1647
<212> TYPE: DNA
<213> ORGANISM: Artificial Sequence
<220> FEATURE:
<223> OTHER INFORMATION: LZ1561 codon adapted nucleotide sequence of kivD_la

<400> SEQUENCE: 1

```
atgtatacag ttggagatta tttattagat agattacatg aattaggaat agaagaaata      60
tttggtgtac caggagatta caatttacaa ttttttagatc aaataataag tagaaaagat    120
atgaaatggg tggggaatgc aaatgagtta aatgcaagtt acatggctga tggatatgca    180
agaactaaaa aggcagctgc attccttaca acctttggag taggagaact aagtgcagta    240
aatgggcttg caggttcata tgctgaaaac ttacctgtag ttgaaatcgt aggtagtcca    300
acttcaaaag tccaaaacga aggaaaattt gtacaccata ctctggctga cggagatttt    360
aaacatttta tgaaaatgca tgaacctgta acagctgcga aacccttttt aactgcggaa    420
aatgctacag ttgaaataga tagagtttta agtgctcttt taaggagag aaagcctgtt     480
tatattaatc ttcccgtaga tgtagctgct gctaaggcag agaaaccttc tttacctttg    540
aaaaaggaaa acagcacttc taatacttcc gatcaagaga tattaaataa aattcaagaa    600
tccttaaaaa atgctaaaaa acctatagtt attacaggac acgaaataat atctttggc    660
ctagaaaaaa cagtaagtca gtttataagt aaaacaaaat tacctataac tactttaaat    720
ttcggtaaga gttctgttga cgaggcactt ccaagttttt taggaatata taatggaaaa    780
ttgagtgaac caaatctaaa agagtttgta gagtcagcag actttatact aatgcttggt    840
gtgaagttaa ctgattcaag tactggagcc tttactcatc atttaaatga aaacaaaatg    900
ataagtttaa acattgatga gggcaaaatt ttcaatgagt caattcaaaa ttttgatttt    960
gaatctttaa tttcatcact tctggattta tcagaaatag agtataaagg caaatatatt   1020
gataagaaac aagaagattt tgttccaagt aatgcactat taagtcaaga taggttatgg   1080
caggcagttg aaaatttaac tcaaagcaat gagactatag tagcagaaca gggaacatca   1140
ctatttggag cgtcttctat ttttcttaag ccaaaaagtc attttatagg tcagccatta   1200
tggggttcta taggatatac ttttccagct gcattaggat cacagatagc agataaagaa   1260
tctagacatc ttttgttcat aggcgatggt tccttgcagt taacagtcca ggaattagga   1320
cttgcaataa gagaaaaaat aaaccctatt tgtttcataa taaataatga tggatatact   1380
gctgaaagag aaatacatgg accaaatcag agctataatg atattccaat gtggaactat   1440
tctaaactgc ctgaatcatt tggggctaca gaagaaaggg tagtgtcaaa aatagttaga   1500
acagaaaatg aatttgtaag tgtcatgaaa gaagctcagg ctgatccaaa cagaatgtat   1560
tggattgaac tcatacttgc aaaagaggat gctccaaaag tattaaagaa atggggaaa    1620
ctttttgctg aacaaaacaa atcttaa                                        1647
```

<210> SEQ ID NO 2
<211> LENGTH: 1638
<212> TYPE: DNA
<213> ORGANISM: Artificial Sequence
<220> FEATURE:
<223> OTHER INFORMATION: LZ1561 codon adapted nucleotide sequence of abPPDC

<400> SEQUENCE: 2

```
atgaaattgg cagaagcatt actcagagca ttgaaagata gaggggcaca ggcaatgttt      60
ggtatacctg gagattttgc acttcctttt ttcaaagttg ctgaagaaac tcaaatactt    120
cctttgcaca ctcttagcca tgaacctgct gtaggttttg cagcagatgc agctgcaaga    180
tattcttcta cattaggtgt agcagcagtt acttacggag caggagcatt taatatggta    240
aatgcagttg ctggtgccta tgcagaaaaa agccctgtag tagttatatc tggtgctcct    300
```

```
ggtacaacag aaggaaatgc tggtcttta cttcaccatc agggaagaac tttagacact    360
caattccagg tatttaagga gataacagtt gcccaggcta gattagatga tcctgctaag    420
gctcctgccg aaatagcaag agtacttggt gctgctagag cgctctcaag accagtttat    480
ttagaaatac ctagaaatat ggtaaatgct gaagtagaac cagtagggga tgatccagca    540
tggccagtag acagagatgc tttagctgcc tgtgctgatg aagtacttgc agctatgaga    600
tctgctacaa gtcctgtttt aatggtttgt gtagaggtta aagatatgg acttgaagca    660 aaagttgctg aattagcaca gagacttgga gtacctgtag taacaacatt tatgggacgc    720
ggattacttg cagatgcacc cactcctcct ttaggaactt atataggagt agcaggagat    780
gcagaaataa ctagattagt ggaagaatca gatggattat ttttacttgg agcaattctt    840
tcagatacaa attttgcagt ctctcaaaga aaaatagact aagaaaaac cattcatgca    900 tttgatcgtg cagttaccct tggatatcat acttatgctg acattccttt agcaggacta    960
gttgatgccc ttctagaaag acttcctcct tcagacagga cgactagagg taaagagcca   1020
catgcctatc ctacaggtct tcaggctgat ggagaaccaa tagctccaat ggacattgcc   1080
cgtgctgtga acgacagagt acgtgctggt caggaacctc ttttaatagc agctgatatg   1140
ggtgactgct tatttacagc tatggatatg atagatgctg gtcttatggc accgggctat   1200
tatgcaggca tgggatttgg agttccagct ggtattggtg ctcaatgtgt atcaggcggc   1260
aaaagaatac ttactgttgt tggtgacgga gcattccaga tgacaggctg ggaacttgga   1320
aattgtagaa gattaggtat tgaccctata gtaatacttt taataatgc ttcttgggaa   1380 atgttaagaa catttcagcc tgaaagtgct tttaatgatt tagatgattg gagatttgca   1440
gatatggctg ctggaatggg cggcgacggt gtaagagtca ggacaagggc tgagttgaag   1500
gctgcattag ataaagcatt tgccacaagg ggcagattcc agcttataga agcaatgata   1560
ccgagaggtg tgcttttccga taccttgct agatttgttc aaggccaaaa gaggcttcac   1620
gcagctccta gagaataa                                                 1638
```

<210> SEQ ID NO 3
<211> LENGTH: 1083
<212> TYPE: DNA
<213> ORGANISM: Artificial Sequence
<220> FEATURE:
<223> OTHER INFORMATION: LZ1561 codon adapted nucleotide sequence of adh6

<400> SEQUENCE: 3

```
atgtcgtatc ctgaaaaatt tgaaggtata gctattcaat cccatgaaga ctggaaaaat     60
cccaaaaaaa caaagtacga cccaaaaacct ttctatgacc atgatataga tataaagatt    120
gaagcatgtg gagtatgtgg aagtgatatt cattgtgcgg caggccattg gggaaatatg    180
aaaatgccat tagttgtggg acatgaaatt gttggaaaag ttgtaaagtt aggtcctaaa    240
tcaaattctg gactaaaagt tggacagaga gttggagttg gtgctcaagt attttcttgt    300
ttagagtgtg atagatgtaa aaatgacaat gaaccttact gtactaaatt tgttactact    360
tattcacaac cttatgaaga tggatatgta agtcagggag gctatgcaaa ctatgttaga    420
gttcacgagc actttgtagt acctattcca gaaaatattc catctcactt agcagctcct    480 ctttatatgcg gtggacttac tgtttatagt ccacttgtta gaaatggttg tggtcctggg    540
aaaaaagtcg gaatagttgg acttggcgga attggaagta tgggaacttt aataagtaaa    600
gctatgggag ctgaaactta tgtaatttct agatcatcaa gaaagagaga agatgcaatg    660
```

```
aagatgggag cagatcacta tattgctaca ttagaagagg gggattgggg ggaaaagtac    720
tttgatactt ttgatttaat tgtcgtatgt gcttcaagtc ttacagatat agattttaat    780
ataatgccaa aagcaatgaa agttggtgga cgaatagtat ctataagtat acctgaacag    840
cacgaaatgt tatctttaaa accttatgga ctaaaggctg tatctatttc ttattctgca    900
ttggggtcta ttaaagaatt gaatcaatta ttaaaactgg ttagtgaaaa agatataaaa    960
atttgggtag aaacacttcc tgtaggtgag gcaggagtcc atgaggcttt tgagagaatg   1020 gaaaaggtg atgtaagata tagatttaca cttgttggct atgataaaga gttttctgat   1080
tag                                                                 1083

<210> SEQ ID NO 4
<211> LENGTH: 1908
<212> TYPE: DNA
<213> ORGANISM: Artificial Sequence
<220> FEATURE:
<223> OTHER INFORMATION: LZ1561 codon adapted nucleotide sequence aro10

<400> SEQUENCE: 4
atggcaccag taacaattga aaaatttgta aatcaagagg aaagacattt ggtatcaaac     60
cgttcagcta caattccatt tggggaatat atattcaaga acttttgag tatagataca    120 aaaagtgttt ttggagttcc tggagatttt aatctttccc tcttagagta cttatattca    180
ccatcagttg aatctgcagg attgagatgg gttggtactt gtaatgaact aaatgctgct    240
tatgcagcag atggttatag cagatattca aataaaatag ggtgtcttat aacaacttat    300
ggagtaggcg agttatctgc attgaatgga atagcaggat catttgcaga aatgttaaaa    360
gtgcttcaca ttgtaggcgt tgctaagagc atagatagcc gatcttcaaa tttctcagat    420
agaaatctac atcatcttgt tccacaacta catgattcaa acttcaaagg acctaatcat    480
aaagtttatc atgatatggt aaaagatagg gtagcatgct ctgttgctta tcttgaagac    540
atagaaactg cttgtgatca agttgataat gtaataagag atatatacaa atactcaaaa    600
ccaggatata tatttgttcc agcagacttt gcagatatgt cagttacatg tgataactta    660
gttaatgtac caagaataag tcaacaggat tgcatagttt atccatctga aaatcagtta    720
agtgacatta taaataaaat aacttcctgg atttacagtt ctaaaacccc agccatttta    780
ggtgatgtat taactgatag atatggtgta tcaaattttt taaataaact tatatgtaag    840
actggaatct ggaatttttc aactgttatg ggtaaatcag ttatagatga agtaatccca    900
acttacatgg tcaatataa tggaaaagaa ggtcttaaac aagtgtatga acattttgag    960
ctttgtgatt tagtgcttca ctttggtgtg gacataaacg aaattaacaa tggacattat   1020
acttttactt ataaacctaa cgcaaaaata atacaatttc atccaaacta tataagactt   1080
gtagatacaa gacaaggaaa tgagcaaatg ttcaaaggca taaactttgc tcctatacta   1140
aaagagctgt ataaaagaat agatgtatca aagttgtcac ttcagtatga ttcaaatgta   1200
actcaataca ctaatgagac aatgagatta gaagatccca ctaatggaca atcttcaatt   1260
attacccagg tacatcttca aaaaacgatg ccaaaattcc tcaatccagg agatgttgtt   1320
gtctgtgaaa caggttcttt tcaatttttct gtgagggatt ttgcattccc ttctcaatta   1380
aaatatatat ctcaaggatt tttcctttca atcggtatgg cattaccagc tgcattggga   1440
gttggaatag caatgcaaga ccattcaaat gctcatataa atggcggcaa tgttaaagag   1500
gattataaac caagacttat tttatttgaa ggagatggtg ctgcacaaat gacaattcaa   1560
```

-continued

| gaactatcta caatattaaa atgtaatatt cctcttgaag taataatttg gaacaacaat | 1620 |
| gatatacta ttgaaagagc aataatgggt ccaacaagat cttataatga tgtaatgtcg | 1680 |
| tggaaatgga ctaaattatt tgaggcattt ggtgatttcg atggaaagta tacaaattct | 1740 |
| actttgatac agtgtccttc aaagttagct ttaaaacttg aagaactcaa gaactcaaat | 1800 |
| aaaagatctg gaatagaatt attagaagtt aaacttggag agttagactt ccctgagcaa | 1860 |
| ctaaaatgca tggtagaagc agcagcactt aagagaaaca aaaaataa | 1908 |

<210> SEQ ID NO 5
<211> LENGTH: 1092
<212> TYPE: DNA
<213> ORGANISM: Artificial Sequence
<220> FEATURE:
<223> OTHER INFORMATION: LZ1561 codon adapted nucleotide sequence of
      phenylacetalyhde reductase (blPAR) from Brevibacterium linens

<400> SEQUENCE: 5

| atgaaagcaa gtttggcaac ggcaattggc ggcgaattca cagtacatga cgtagtaata | 60 |
| gatgacccac aaggaagaga ggtccttgtg gatgtgaaag cttcaggatt atgtcattct | 120 |
| gatttacact aatagatca tgatttcggt ctccctcttc cagctgtagg cggccatgaa | 180 |
| atttcaggtg tagtgagaag tgtaggacca ggcgttacca gtatgtctgt tggagaccat | 240 |
| gttgtagctt gtcttataac ttttgcggt gcatgtgcag aatgccttc aggaaaaact | 300 |
| actttatgtt caaatcctac tgctgtagca agaaaagaag gagaaaagcc aagagtttca | 360 |
| ttccctgatg gtcaggaaat tgcacaatca gttaatgttg gcggctttgc agaacaagta | 420 |
| ctagttcatg aaaatcagct tgcagtagta acaatcaga tacctttccc tcaggcagca | 480 |
| cttttagggt gctcagttgt cacaggagca ggagcagcta taaatacagc tcatgtaaga | 540 |
| ccaggggata cagtagcggt tataggaaca ggcggcatag gattaaacgc aataagcgga | 600 |
| gcaagattag caggggctaa gcacattata gctattgata tagttgattc taaattagag | 660 |
| gctgcaaaaa agttgggagc tacagatctt ataaattcat caactactga tccagtggca | 720 |
| gcagttcaag aattaactgg cggcgtagat catgcatttg aagtaattgg attagaagct | 780 |
| acgcagaggc aagttcagca attaacaaaa ccaggcggca cggcatattt aataggcata | 840 |
| gcaccaccag gaacaactac tgaatttaca tcatcattag atagtttgtt tgctcaaaga | 900 |
| agactgcagg ctgttttgat gggtagtagt aatgttaaaa gagatatagc attatatgca | 960 |
| gacttgtatg ttcagggacg ttttgaatta gatcatttag tatcaagaga aatatccata | 1020 |
| aatgagataa atgatggtta tgaagcatta aaaaaaggtg aagttatacg ttcagttata | 1080 |
| accagttttt aa | 1092 |

<210> SEQ ID NO 6
<211> LENGTH: 1020
<212> TYPE: DNA
<213> ORGANISM: Artificial Sequence
<220> FEATURE:
<223> OTHER INFORMATION: LZ1561 codon adapted nucleotide sequence of
      phenylacetalyhde reductase (ecPAR) from Escherichia coli

<400> SEQUENCE: 6

| atgtcaatga taaaatcata tgcagcaaaa gaagcaggcg gcgaattaga agtttacgaa | 60 |
| tatgatccag ggaattaag gcctcaagat gtagaagttc aagttgatta ctgtggaata | 120 |
| tgccattccg atttatctat gatagataat gaatgggggat ttagtcagta tcctcttgta | 180 |
| gcaggacatg aagttattgg cagagttgta gctcttggtt cagcagctca ggataagggc | 240 |

```
ttacaggtag gtcagagagt agggataggc tggactgccc gttcgtgtgg acactgcgat    300
gcatgtatca gtggaaatca aataaattgt gaacaaggtg cagttccaac tataatgaat    360
aggggcggct ttgcagaaaa attaagagca gattggcaat gggtaattcc tcttccagaa    420
aacatagata tagaatcagc aggtcctctc ctttgtggcg gcattacagt atttaaacct    480
cttcttatgc atcatattac tgctacatca agagtaggag taatcggtat aggcggcctt    540
ggacatatag caattaaact tcttcatgct atgggttgtg aagttacggc atttagttca    600
aatccagcta aagagcaaga agttcttgct atgggtgccg acaaggtagt taacagtagg    660
gatccacagg cactgaaagc actggcggga caatttgatc ttataataaa tacagtaaac    720
gtttctctag attggcaacc atattttgag gcattaactt atggcggcaa tttccataca    780
gttggagccg ttcttacacc actatctgtt ccagctttta cacttatagc aggagatcgt    840
agtgtttccg gctctgcaac tggtactcct tatgaactta aaaacttat gagatttgca     900 gcaagatcta aagttgcacc taccacagag cttttcccta tgagcaagat aaatgatgca    960
attcagcacg ttagagatgg aaaagcaaga tatagggttg tgttaaaggc tgattattag   1020
```

<210> SEQ ID NO 7
<211> LENGTH: 1041
<212> TYPE: DNA
<213> ORGANISM: Artificial Sequence
<220> FEATURE:
<223> OTHER INFORMATION: LZ1561 codon adapted nucleotide sequence of
      phenylacetalyhde reductase (rrPAR) from Rhodococcus ruber

<400> SEQUENCE: 7

```
atgaaagctt tgcaatatac agaaatagga agtgaaccag tagtagtaga tgtaccaaca     60
ccagcgccag gaccaggaga gatcttatta aaggtaactg cagcaggact tgtcattca    120 gatatatttg taatggatat gcctgctgaa cagtatattt atggccttcc attaacgctt    180
ggccatgagg gtgttggaac agttgcagaa ttaggggcag gtgtaacagg atttgaaaca    240
ggtgatgctg ttgctgttta tggaccttgg ggatgcggtg cctgccatgc ttgtgcccgt    300
ggaagggaaa actattgtac tagagctgca gagttaggaa taacaccccc tggactggga    360
tcacctggaa gtatggcaga gtatatgatt gtagattctg caagacattt agttcctata    420
ggtgatttgg atcctgttgc agctgttcct cttacagatg ctggattgac acctatcat     480 gcaataagta gagtgttacc gcttcttgga ccaggatcta cagctgtagt tataggagtt    540
ggcggcttag acatgttgg catccaaata ttaagagcag tgtcagcagc aagagttata    600
gcagttgatt tagatgatga cagattagct ttagcaagag aagttggtgc agatgcagct    660
gttaaaagtg gagcaggagc agcagatgct attcgtgaac ttacaggcgg cgaaggagca    720
actgctgtgt ttgattttgt aggagctcag agtacaattg atactgcaca gcaggtagta    780
gcaatagacg gccatatatc cgtagttggt attcatgcag gtgctcatgc aaaagtaggt    840 tttttttatga tacctttgg agcttctgtt gtaactcctt actggggtac ccgttctgaa    900
cttatggatg tagtagatct tgcaagagca ggcagacttg atatacatac tgagactttt    960
actttagatg aaggtccgac tgcatataga agactaagag aaggttccat aagaggtagg   1020
ggagtagtag tgcctggata a                                              1041
```

<210> SEQ ID NO 8
<211> LENGTH: 1047
<212> TYPE: DNA
<213> ORGANISM: Artificial Sequence
<220> FEATURE:
<223> OTHER INFORMATION: LZ1561 codon adapted nucleotide sequence of phenylacetalyhde reductase (rsPAR) from Rhodococcus sp. ST-10

<400> SEQUENCE: 8

```
atgaaagcaa ttcaatacac aagaatagga gcagaaccag aacttacaga ataccaaaa      60
ccagagccag gaccagggga agttcttctt gaagtaactg cagctggagt atgtcacagt    120
gatgattta taatgtcgct gcctgaagaa cagtatacat atggactacc acttacatta    180
ggtcatgaag gtgcaggaaa agtagcagct gtaggtgagg gagtagaagg tttagacata    240
ggaactaatg tagtagtata tggaccttgg ggatgtggaa attgctggca ctgctctcaa    300
ggcttggaaa actactgttc aagagctcag gaacttggaa taaatccacc tggacttggt    360
gcaccaggtg cattagctga atttatgatt gtagattcac cacgtcattt agtgcctata    420
ggagatttgg atcctgttaa aactgtacca ctaactgatg caggacttac accttatcat    480
gctataaaaa gaagtttacc aaagttaaga ggcggctcct atgccgttgt aataggaaca    540
ggcggccttg gacatgtagc tatccaatta ttaagacatt tgtctgcagc tactgttata    600
gcacttgacg tttcagcaga taaattggaa cttgctacta aggtaggtgc acatgaagtt    660
gtattatcag acaaggatgc agctgaaaat gtaaggaaaa ttacaggatc acaaggagca    720
gccttagttt tagattttgt tggatatcaa cctacaattg acactgctat ggctgtagct    780
ggtgttggaa gtgatgttac aatagtaggt ataggtgatg tcaagctca tgcaaaggta    840
ggtttctttc aaagtcctta tgaagcttca gtaactgtac cttattgggg agctagaaat    900
gagttaatag aactcataga tttagctcat gcaggtatat ttgatatttc agtagaaact    960
ttttcacttg acaatggcgc agaagcatat agaagattag ctgctggaac actttcagga    1020
agagcagtag tagttccagg attataa                                        1047
```

<210> SEQ ID NO 9
<211> LENGTH: 987
<212> TYPE: DNA
<213> ORGANISM: Artificial Sequence
<220> FEATURE:
<223> OTHER INFORMATION: LZ1561 codon adapted nucleotide sequence of phenylacetalyhde reductase (lePAR) from Solanum lycopersicum

<400> SEQUENCE: 9

```
atgtcagtta cagcaaaaac agtttgtgtt acaggtgctt caggttacat tgcttcatgg      60
ttagttaaat ttttacttca ttctggatat aatgttaagg catctgttag ggatccaaat    120
gatcctaaaa agacccagca tctattaagt cttggcggcg ctaaagaaag gcttcactta    180
tttaaggcaa atctacttga agaaggtagc tttgatgctg ttgtagatgg ttgtgaagga    240
gtattccaca ctgcgtcacc atttattac tctgtaactg acccacaagc tgaattgctt    300
gatccagctg taaaaggtac actgaacttg ttaggaagtt gtgcaaaggc accaagcgta    360
aagagagttg tattaactag cagtattgct gctgttgcat actctggtca gccaagaacc    420
ccagaagtag ttgtagatga atcatggtgg acatcaccag attactgtaa agaaaaacaa    480
ctttggtatg ttttaagtaa aactttagct gaagatgctg cttggaaatt tgttaaagaa    540
aagggaatag atatggttgt agttaatcca gctatggtta ttggaccact tttgcagcca    600
acattaaata ctagctctgc agcagtactt tcacttgtaa atggtgctga gacatacca    660
aattcaagtt ttggatgggt aaatgtaaag gactagcaa atgctcatat attagcattt    720
gaaaatccat ccgccaatgg aagatatctt atggtagaaa gagtagctca ttattctgat    780
```

| atattgaaaa ttttaagaga tctatatcca actatgcagt taccagaaaa gtgtgcagat | 840 |
| gataatcctc ttatgcaaaa ttatcaggtt tcaaaagaaa aggccaaatc tttaggaata | 900 |
| gaatttacga ctttagaaga atctatcaaa gaaactgttg aatcactaaa ggagaaaaaa | 960 |
| ttctttggcg gctcgtcctc catgtaa | 987 |

```
<210> SEQ ID NO 10
<211> LENGTH: 1053
<212> TYPE: DNA
<213> ORGANISM: Artificial Sequence
<220> FEATURE:
<223> OTHER INFORMATION: LZ1561 codon adapted nucleotide sequence of
      AroG from Escherichia coli

<400> SEQUENCE: 10
```

| atgaattatc aaaatgatga tttaagaata aagaaatta aagaattatt acctcctgta | 60 |
| gctttattag aaaaatttcc tgcaactgaa atgcagcaa atactgtagc acatgcaaga | 120 |
| aaagcaatac ataaaatact aaaggtaat gatgatagat tattagtagt aataggacct | 180 |
| tgtagtatac atgatcctgt agcagcaaaa gaatatgcaa ctagactttt agcattaaga | 240 |
| gaagaattaa aagatgaatt agaaatagta atgagagtat atttgaaaa acctagaact | 300 |
| actgtaggat ggaaaggact tataaatgat cctcatatgg ataatagttt tcaaataaat | 360 |
| gatggactta aatagcaag aaaattactt ttagatataa atgatagtgg attacctgca | 420 |
| gctggtgaat ttttagatat gataactcct caatatttag cagatttaat gagttgggga | 480 |
| gcaattggag caagaactac tgaaagtcaa gtacatagag aagatgcaag tggacttagt | 540 |
| tgtcctgtag gatttaaaaa tggaactgat ggaactataa agtagcaat agatgcaata | 600 |
| aatgcagctg gtgcacctca ttgttttctt agtgtaacaa atgggggaca tagtgcaata | 660 |
| gtaaatacta gtggaaatgg tgattgtcat ataatactta gaggtggaaa agaacctaat | 720 |
| tattctgcaa aacatgtagc agaagtaaaa gaaggactta ataaagctgg acttcctgca | 780 |
| caggtaatga tagattttc tcatgcaaat agtagtaaac aatttaagaa acaaatggat | 840 |
| gtatgtgcag atgtatgtca gcaaatagct ggaggtgaaa aagcaataat tggagtaatg | 900 |
| gtagaaagtc atttagtaga aggtaatcaa agtttagaaa gtggtgaacc tttagcttat | 960 |
| ggaaaagta taactgatgc atgtatagga tgggaagata ctgatgcact tcttagacaa | 1020 |
| cttgcaaatg cagtaaaagc aagaagagga taa | 1053 |

```
<210> SEQ ID NO 11
<211> LENGTH: 819
<212> TYPE: DNA
<213> ORGANISM: Artificial Sequence
<220> FEATURE:
<223> OTHER INFORMATION: LZ1561 codon adapted nucleotide sequence of
      ecAroE from Escherichia coli

<400> SEQUENCE: 11
```

| atggaaactt tatgcagtat tggcaatcct atagcacatt caaaatcacc atttatacat | 60 |
| caacaatttg ctcagcaatt aaatattgaa catccttatg aagagttttt agctccaata | 120 |
| aatgattta aaatactttt aaatgctttt ttttcagcag gcggcaaagg agcaaatgta | 180 |
| actgtaccct ttaaagagga agcttttgcc agagcagatg agttaactga aagagcagca | 240 |
| ttagctggtg cggttaatac attgatgaga ctagaagatg gtaggctttt aggagataat | 300 |
| actgatgggg taggtctttt gtctgatctt gaaagacttt cttttataag acctggcctc | 360 |
| cggatccttt taataggtgc aggcggcgca tccaggggag tattacttcc attactatca | 420 |

```
ctggattgtg cagttactat cactaacaga acagtttcaa gagctgaaga gcttgctaaa    480
ttatttgcac atacaggatc aatccaggca ctttccatgg atgaactaga gggacatgaa    540
tttgacttaa ttataaatgc gactagcagt ggtataagtg gggatatacc agctattccc    600
agctctttaa tacatcctgg aatatactgc tatgatatgt tttatcaaaa aggtaagaca    660
ccgttcttag cttggtgtga acaaagagga agcaagagaa atgcagatgg tcttggcatg    720
ctggttgcac aagcagctca tgcatttttta ctatggcatg gagttttacc tgatgttgaa    780
cctgttataa aacagctgca agaagaattg tcagcataa                           819
```

```
<210> SEQ ID NO 12
<211> LENGTH: 831
<212> TYPE: DNA
<213> ORGANISM: Artificial Sequence
<220> FEATURE:
<223> OTHER INFORMATION: LZ1561 codon adapted nucleotide sequence of
      cgAroE from Corynebacterium glutamicum

<400> SEQUENCE: 12
```

```
atgggatcac atataactca cagagcagca gttttaggct caccaattga acattcaaaa    60
tcaccagtgc ttcataatac aggatataaa gctttaggac ttgatcaatg ggaatatgac   120
aggtttgaat gcacaggaga tatgttaccg ggcatagttt caggagcaga tgaaacttat   180
cgaggatttt ctgttacaat gccttctaaa tttgctgctt tagaatttgc agatgaagta   240
actgaaagag caagagctat tggatcagca aatacattac ttagaactga aacaggatgg   300
agagcggata atactgatgt ggatggaata agaggtgcat taggtgaatt gttaggaagt   360
gcatctcttg caggaaaaca tgctattgta ataggatcag gcggcactgc aagacctgca   420
atttgggcac ttatagaagc aggagtagca agaataactg tacttaatag atcagataga   480
actgctgaac ttcaaacttt atttgatgaa acaccaacta cgttagcata tgctccactt   540
gagcacttgg atattgaagc tgacgttgta gtttctactg ttccttcagc tgctatagct   600
ggtcttgaag atacactggc tatagcacca gtgttggatg ttatatatga tccatggcca   660
actcctttag tagaagttgc aagagctaaa ggacttaagg ctgtaggcgg ccacgtaatg   720
ttggcccatc aatcatatgg tcaatttgaa cagtttacag gaatggatgc tccaagggat   780
gcaatgagag aagctttaga agaatcactt ggaataagtg aggaacatta g            831
```

```
<210> SEQ ID NO 13
<211> LENGTH: 1014
<212> TYPE: DNA
<213> ORGANISM: Artificial Sequence
<220> FEATURE:
<223> OTHER INFORMATION: LZ1561 codon adapted nucleotide sequence of
      pheA1 from Escherichia coli

<400> SEQUENCE: 13
```

```
atgactagtg aaaatccatt acttgcttta agagaaaaaa tatctgccct tgatgaaaaa    60
ttacttgctt tattagcaga aagaagagag cttgcagttg aggtaggtaa ggcaaagttg   120
ctttcgcaca ggcctgttag agatattgat agggaaagag atcttttgga aagattaata   180
actcttggta aggctcatca tttgatgctc attatataa caagattatt tcagctcata   240
atagaagact cagttcttac tcaacaggca ttgcttcaac aacatttgaa taagatcaat   300
cctcactcag ccagaatagc ttttttaggc ccaaaaggtt cctattcaca tctggctgct   360 agacaaatatg cagcaaggca ttttgaacag ttcattgaat cagggtgtgc taaatttgca   420
```

```
gatatattta accaggtaga aacaggtcaa gccgattatg ctgtagtacc tatagaaaat        480
acgtcgagtg gtgctattaa tgatgtatat gatcttttac agcacactag cctatccata        540
gtaggagaaa tgactttaac tatagatcac tgccttttag tatcaggtac tacagatctt        600
tcaactataa atacagtata ttctcatcca cagccatttc aacaatgtag taaattccta        660
aacagatatc ctcactggaa gattgaatat actgaaagta ccagtgcagc aatggaaaaa        720
gttgcacagg ctaaatcacc acatgtagct gcattaggtt ctgaggctgg cggcacgttg        780
tatggattac aagtactaga aagaatagaa gccaatcaaa ggcaaaattt tacaagattt        840
gtggttttgg caagaaaagc aataaatgtt tcagatcaag tcccagcaaa aactacatta        900
ctaatggcta caggacaaca ggctggggct ttagttgagg ctttattagt gttgagaaat        960
cacaatttaa taatgactag gcttgaatca agacctattc atggaaatcc ttaa            1014

<210> SEQ ID NO 14
<211> LENGTH: 1161
<212> TYPE: DNA
<213> ORGANISM: Artificial Sequence
<220> FEATURE:
<223> OTHER INFORMATION: LZ1561 codon adapted nucleotide sequence of
      pheA2 from Escherichia coli

<400> SEQUENCE: 14
atgacatcag aaaatccatt attggcactt agagaaaaga tatcagcact tgacgaaaaa         60
ttacttgcat tattggcaga gagaagagag cttgctgttg aagttggaaa ggctaagctg        120
ttgtcccacc gtccagttag agatattgac agagaacggg acttattaga aagactcatt        180
acattaggaa aggctcatca tttggatgca cattatatta caagattatt tcagctcata        240
atagaagatt cagtattaac tcaacaggct ttacttcaac agcacttaaa taaaataaat        300
ccacattcag ctaggattgc attcttagga ccaaaaggaa gttatagtca tcttgctgca        360
agacaatatg cagcaagaca ctttgaacaa tttattgaat caggatgtgc taaatttgca        420
gatatcttca atcaagtaga aacaggtcag gctgattatg cagtagttcc aatagaaaat        480
acgtcaagcg gtgctataaa tgatgtatat gatttacttc agcatacaag cttatctata        540
gttggtgaga tgacattgac tatagatcac tgcttacttg taagtggaac tacagatttg        600
tccactataa atactgttta cagccatcca cagccatttc aacagtgtag taaattttta        660
aatagatatc cacactggaa aatagaatac acagaaagta cttccgcagc aatggaaaag        720
gttgcacagg caaagtctcc tcacgttgca gcattaggta gtgaagcagg cggcacactt        780
tatggacttc aagtactcga aaggattgaa gcaaaccaaa ggcaaaattt tactagattt        840
gttgtacttg ccagaaaggc tataaatgta agtgatcagg taccagctaa aactacttta        900
cttatggcaa caggacaaca ggcaggagca ctagtagaag cacttttagt attgagaaat        960
cataatctca taatgacgag gttagagtca agaccaattc atggtaatcc aagagaggaa       1020
atgttttacc ttgatatcca agcaaatctt gaatcagcag aaatgcagaa agcattaaag       1080
gaactgggtg aaaataacaag atcaatgaaa gtgcttggat gttatccttc tgaaaatgtg       1140
gtacctgtag atccaactta a                                                 1161
```